US011956414B2

(12) United States Patent
Freeman et al.

(10) Patent No.: US 11,956,414 B2
(45) Date of Patent: Apr. 9, 2024

(54) WEARABLE IMAGE MANIPULATION AND CONTROL SYSTEM WITH CORRECTION FOR VISION DEFECTS AND AUGMENTATION OF VISION AND SENSING

(71) Applicant: Raytrx, LLC, Tulsa, OK (US)

(72) Inventors: Michael Hayes Freeman, Tulsa, OK (US); Richard C. Freeman, Tulsa, OK (US); Mitchael C. Freeman, Sapulpa, OK (US); Chad Boss, Tulsa, OK (US); Jordan Boss, Tulsa, OK (US)

(73) Assignee: RAYTRX, LLC, Tulsa, OK (US)

( * ) Notice: Subject to any disclaimer, the term of this patent is extended or adjusted under 35 U.S.C. 154(b) by 306 days.

(21) Appl. No.: 15/962,661

(22) Filed: Apr. 25, 2018

(65) Prior Publication Data

US 2018/0249151 A1 Aug. 30, 2018

Related U.S. Application Data

(63) Continuation-in-part of application No. 15/073,144, filed on Mar. 17, 2016, now Pat. No. 9,955,862.
(Continued)

(51) Int. Cl.
*H04N 13/332* (2018.01)
*A61B 3/00* (2006.01)
(Continued)

(52) U.S. Cl.
CPC ......... *H04N 13/332* (2018.05); *A61B 3/0025* (2013.01); *A61B 3/005* (2013.01);
(Continued)

(58) Field of Classification Search
CPC ....... A61B 5/6803; A61B 5/0002; A61B 5/01; A61B 5/024; A61B 5/0476; A61B 5/0478;
(Continued)

(56) References Cited

U.S. PATENT DOCUMENTS 8,135,227 B2 3/2012 Lewis et al.
8,311,328 B2 11/2012 Spruck
(Continued)

FOREIGN PATENT DOCUMENTS

| CN | 105188516 A | 12/2015 |
|----|-------------|---------|
| EP | 4052647 | 9/2022 |
| JP | 09245195 | 9/1997 |

OTHER PUBLICATIONS

International Search Report and Written Opinion (PCT/US16/22944; O/R 068596.00004); dated Jun. 16, 2016.
(Continued)

*Primary Examiner* — Brandi N Thomas
(74) *Attorney, Agent, or Firm* — Howard & Howard Attorneys PLLC

(57) ABSTRACT

A wearable image manipulation system comprising a camera input system, an image projection system, where the image projection system is capable of being worn by a user, and a processor in communication with the camera input system and the image projection system such that the processor is capable of receiving an image from the camera input system, modifying the image to produce a modified image, and displaying the modified image on the image projection system. The camera input system may comprise a contact lens with a camera mounted thereon. Additionally or alternately, the system may be capable of tracking a user's eye movement to accurately capture where the user is looking with the camera input system.

44 Claims, 26 Drawing Sheets

Related U.S. Application Data

(60) Provisional application No. 62/489,801, filed on Apr. 25, 2017, provisional application No. 62/134,422, filed on Mar. 17, 2015.

(51) Int. Cl.

| | | |
|---|---|---|
| *A61B 5/00* | (2006.01) | |
| *A61B 5/11* | (2006.01) | |
| *A61F 9/00* | (2006.01) | |
| *A61F 9/08* | (2006.01) | |
| *G02B 27/01* | (2006.01) | |
| *G02C 11/00* | (2006.01) | |
| *G06F 1/16* | (2006.01) | |
| *G06F 3/01* | (2006.01) | |
| *G06V 20/20* | (2022.01) | |
| *G06V 40/18* | (2022.01) | |
| *G16H 20/30* | (2018.01) | |
| *G16H 30/40* | (2018.01) | |
| *G16H 40/63* | (2018.01) | |
| *G16H 50/20* | (2018.01) | |
| *H04N 13/189* | (2018.01) | |
| *H04N 13/366* | (2018.01) | |
| *A61B 3/024* | (2006.01) | |
| *A61B 3/113* | (2006.01) | |
| *A61B 3/14* | (2006.01) | |
| *A61B 90/00* | (2016.01) | |
| *A61B 90/50* | (2016.01) | |
| *G02C 5/14* | (2006.01) | |

(52) U.S. Cl.
CPC .......... *A61B 3/0058* (2013.01); *A61B 5/1123* (2013.01); *A61B 5/6803* (2013.01); *A61B 5/742* (2013.01); *A61F 9/00* (2013.01); *A61F 9/08* (2013.01); *G02B 27/017* (2013.01); *G02B 27/0172* (2013.01); *G02C 11/10* (2013.01); *G06F 1/163* (2013.01); *G06F 3/011* (2013.01); *G06F 3/013* (2013.01); *G06V 20/20* (2022.01); *G06V 40/193* (2022.01); *G16H 20/30* (2018.01); *G16H 30/40* (2018.01); *G16H 40/63* (2018.01); *G16H 50/20* (2018.01); *H04N 13/189* (2018.05); *H04N 13/366* (2018.05); *A61B 3/024* (2013.01); *A61B 3/113* (2013.01); *A61B 3/145* (2013.01); *A61B 5/0059* (2013.01); *A61B 5/1114* (2013.01); *A61B 5/746* (2013.01); *A61B 2090/365* (2016.02); *A61B 90/39* (2016.02); *A61B 2090/502* (2016.02); *A61B 2560/0242* (2013.01); *A61B 2562/0204* (2013.01); *A61B 2562/0219* (2013.01); *A61B 2562/0223* (2013.01); *G02B 2027/0138* (2013.01); *G02B 2027/014* (2013.01); *G02B 2027/0178* (2013.01); *G02C 5/14* (2013.01); *G06F 3/012* (2013.01); *G06F 3/014* (2013.01)

(58) Field of Classification Search
CPC ... A61B 5/11; A61B 5/14553; A61B 2503/10; A61B 5/4064; A61B 2562/0219; A61B 5/1112; A61B 5/1121; A61B 5/1128; A61B 5/7282; A61B 6/0457; A61B 6/4258; G02C 7/12; G02C 2202/16; G02C 7/02; G02C 7/086; G02C 1/00; G02C 1/06; G02C 7/10; G02C 7/102; G02C 7/108; G02C 7/16; G02C 7/061; G02C 11/10; G02C 13/001; G02C 7/101; G02C 7/104; G02B 1/041; G02B 5/3033; G02B 1/04; G02B 5/305; G02B 27/0081; G02B 27/0172; G02B 5/3083; G02B 1/043; G02B 27/0101; G02B 27/283; G02B 27/30; G02B 27/4211; G02B 2027/015; G02B 27/4261; G02B 17/0852; G02B 1/08; G02B 1/14; G02B 2027/0116; G02B 2027/0127; G02B 2027/0141; G02B 27/0056; G02B 27/0103; G02B 5/30; G02B 6/0096; G02B 27/0037; G02B 27/144; G02B 27/4238; G02B 30/34; G02B 3/00; G02B 5/23; G02B 19/0028; G02B 19/0052; G02B 2027/011; G02B 2027/0118; G02B 2027/0123; G02B 2027/0154; G02B 2027/0174; G02B 27/0031; G02B 27/0176; G02B 27/095; G02B 27/1073; G02B 27/126; G02B 27/285; G02B 27/4272; G02B 30/25; G02B 3/04; G02B 3/08; G02B 3/14; G02B 5/04; G02B 5/1814; G02B 5/3008; G02B 5/3041; G02B 6/0028; G02B 7/008; G02B 17/0884; G02B 1/10; G02B 1/115; G02B 2027/0125; G02B 2027/013; G02B 2027/0134; G02B 2027/0138; G02B 2027/014; G02B 2027/0178; G02B 21/00; G02B 21/0004; G02B 5/3016; G02B 5/3058; G02B 6/0026

See application file for complete search history.

(56) References Cited

U.S. PATENT DOCUMENTS

| | | | |
|---|---|---|---|
| 8,350,898 | B2 | 1/2013 | Chang et al. |
| 8,494,298 | B2 | 7/2013 | Lewis et al. |
| 8,771,805 | B2 | 7/2014 | Laude et al. |
| 8,798,756 | B2 | 8/2014 | McMlure et al. |
| 8,812,120 | B2 | 8/2014 | Greenberg et al. |
| 8,831,734 | B2 | 9/2014 | Nanduri et al. |
| 8,831,745 | B2 | 9/2014 | Hung et al. |
| 8,874,224 | B2 | 10/2014 | Greenberg et al. |
| 8,874,239 | B2 | 10/2014 | Greenberg et al. |
| 8,886,329 | B2 | 11/2014 | Greenberg et al. |
| 8,934,983 | B2 | 1/2015 | Greenber et al. |
| 8,954,157 | B2 | 2/2015 | Faraii et al. |
| 8,976,086 | B2 | 3/2015 | Hikes |
| 9,002,462 | B2 | 4/2015 | McClure et al. |
| 9,042,985 | B2 | 5/2015 | Marsll et al. |
| 9,044,590 | B2 | 6/2015 | Greenberg et al. |
| 9,044,591 | B2 | 6/2015 | Greenberg et al. |
| 9,050,468 | B2 | 6/2015 | Greenberg et al. |
| 9,061,150 | B2 | 6/2015 | Greenberg et al. |
| 9,072,888 | B2 | 7/2015 | Greenber et al. |
| 9,072,900 | B2 | 7/2015 | Caspi et al. |
| 9,078,739 | B2 | 7/2015 | Greenberg et al. |
| 9,084,895 | B2 | 7/2015 | Greenberg et al. |
| 9,089,690 | B2 | 7/2015 | Greenberg et al. |
| 9,089,701 | B2 | 7/2015 | Zhou et al. |
| 9,089,702 | B2 | 7/2015 | Dorn et al. |
| 9,095,709 | B2 | 8/2015 | McMiure et al. |
| 9,095,710 | B2 | 8/2015 | Horsager et al. |
| 9,095,722 | B2 | 8/2015 | Mech et al. |
| 2002/0063807 | A1 | 5/2002 | Margulis |
| 2005/0168569 | A1 | 8/2005 | Igarashi |
| 2005/0280603 | A1 | 12/2005 | Aughey et al. |
| 2006/0238710 | A1* | 10/2006 | Dick ...................... A61B 3/103 351/211 |
| 2007/0121070 | A1 | 5/2007 | Alster et al. |
| 2009/0123036 | A1 | 5/2009 | Huang et al. |
| 2009/0128834 | A1* | 5/2009 | Matsuhira .............. H04N 1/624 358/1.2 |
| 2010/0011959 | A1 | 1/2010 | Marra |
| 2010/0079356 | A1 | 4/2010 | Hoellwarth |
| 2011/0043644 | A1 | 2/2011 | Munger et al. |
| 2012/0281181 | A1 | 11/2012 | Chen et al. |

(56) References Cited

U.S. PATENT DOCUMENTS

| | | | |
|---|---|---|---|
| 2013/0155507 A1* | 6/2013 | Ryu | C09B 47/00 |
| | | | 359/487.02 |
| 2013/0172902 A1 | 7/2013 | Lightcap et al. | |
| 2013/0200595 A1 | 8/2013 | Mackay et al. | |
| 2013/0215147 A1 | 12/2013 | Hikes et al. | |
| 2013/0329184 A1* | 12/2013 | Barzak | G02C 7/12 |
| | | | 351/159.56 |
| 2013/0329190 A1 | 12/2013 | Lewis et al. | |
| 2013/0335543 A1 | 12/2013 | Hikes et al. | |
| 2014/0094655 A1 | 4/2014 | Newman | |
| 2014/0098226 A1 | 4/2014 | Pletcher | |
| 2014/0160264 A1 | 6/2014 | Taylor et al. | |
| 2014/0214122 A1 | 7/2014 | Nanduri et al. | |
| 2014/0243971 A1* | 8/2014 | Pugh | G02C 7/04 |
| | | | 623/6.22 |
| 2014/0275760 A1 | 9/2014 | Lee et al. | |
| 2014/0306866 A1* | 10/2014 | Miller | G06T 7/73 |
| | | | 345/8 |
| 2015/0084841 A1 | 3/2015 | Hikes | |
| 2015/1093984 | 7/2015 | Bar-Zeev et al. | |
| 2015/0355481 A1 | 12/2015 | Hilkes et al. | |
| 2015/0362733 A1 | 12/2015 | Spivack | |
| 2016/0037849 A1* | 2/2016 | Shearman | A42B 3/0426 |
| | | | 2/424 |
| 2016/0091968 A1 | 3/2016 | Angelo et al. | |
| 2016/0247418 A1 | 8/2016 | Folzenlogen et al. | |
| 2016/0270648 A1 | 9/2016 | Freeman et al. | |
| 2017/0007351 A1 | 1/2017 | Yu | |
| 2017/0011706 A1 | 1/2017 | Namkung et al. | |
| 2017/0068119 A1 | 3/2017 | Antaki et al. | |
| 2017/0094167 A1 | 3/2017 | Riedel | |
| 2017/0323615 A1 | 11/2017 | Hazra et al. | |
| 2018/0250085 A1 | 9/2018 | Simi et al. | |
| 2021/0149173 A1 | 5/2021 | Knoblich et al. | |

OTHER PUBLICATIONS

Loshin et al, David, "The Programmable Remapper: Clinical Applications for Patients with Field Defects," Optometry and Vision Science, pp. 389-395, vol. 66, No. 6, US.

Wrobleswki, et al., Dariusz, "Testing of Visual Field with Virtual Reality Goggles in Manual and Visual Grasp Modes," Biomed Research International, vol. 2014 (2014), Article ID 206082, pp. 1-7, http://www.hindawi.com/journals/bmri/2014/206082.

International Search Report and Written Opinion (PCT/US18/22944); dated Jul. 31, 2018.

European Search Report and Written Opinion (European Patent Application No. 18790963.5); dated Jan. 11, 2021.

Extended European Search Report in European Patent Application No. 19833423.7; dated Aug. 20, 2022.

Office Action received in Chinese Patent Application No. 2018800416969; dated Jan. 12, 2023.

Office Action Received in European Patent Application No. 18790963.5; dated Jun. 5, 2023.

* cited by examiner

WEARABLE IMAGE MANIPULATION AND CONTROL SYSTEM WITH CORRECTION FOR VISION DEFECTS AND AUGMENTATION OF VISION AND SENSING

CROSS REFERENCE

This application is based on and claims priority to U.S. Provisional Patent Application No. 62/489,801 filed Apr. 25, 2017. This application is also a continuation in part of U.S. patent application Ser. No. 15/073,144 filed Mar. 17, 2016, which will issue on May 1, 2018 as U.S. Pat. No. 9,955,862 and which claims the benefit of U.S. Provisional Patent Application No. 62/134,422 filed Mar. 17, 2015. All are incorporated herein by reference.

BACKGROUND OF THE INVENTION

Field of the Invention

The present invention relates generally to improvements in Augmented Reality (AR) glasses including using such glasses for medical purposes for the correction of vision defects, and more particularly to a system and methods for compensating for visual defects, for detecting the vision defects, capturing an image, modifying the image for correcting the visual defect, and displaying a modified image for that correction, and also for the correction of what prescription glasses would otherwise do. This present invention also incorporates novel hardware and software applications related to the invention, including the application of smart contact lenses.

Description of the Related Art

Macular degeneration (AMD), macular hole, and other FOV (Field of Vision) related blindness or vision defect conditions, such as central macular scar, histoplasmosis, end-stage glaucoma, Stargardt's disease, central serous retinopathy, myopic macular degeneration, diabetic macular edema, cystoid macular edema, macular holes, macular atrophy, central macular scar, histoplasmosis, macular hole, anterior ischemic optic neuropathy, and retinitas pigmentosa, are often irreversible. The impact to a patient's life due to the loss of a portion of their vision is enormous, including degraded and loss of the ability to read, watch TV, and see computer screens. Some of the conditions can be halted, and fortunately leaves some of the vision intact, and in the case of macular hole or macular degeneration, the peripheral vision remains intact; while in the case of retinitas pigmentosa the peripheral vision is lost and only "tunnel vision" remains. In each of these cases, augmentation of a projected image with pixel manipulation together with real world visual information, "mixed reality" can aid the patient in recovering some or all of their sight.

There have been previous attempts to augment the sight of a patient whose other sight is defective or otherwise impaired, or otherwise compensate for the patient's damaged or impaired sight. For instance, previous efforts have focused on devices that increase the intensity or contrast of the patient's sight and/or increase the magnification of the image seen by the patient while wearing Virtual Reality goggles, which block all other external sight. These attempts have not been very effective, are bulky and expensive, and are presented only in an immersive, occluded, ensconced virtual reality (VR) type of viewing environment, meaning that the patient's existing real-world sight is restricted and the patient can only see what is projected onto that display, while everything else is blocked out. Thus, the patent using these VR type goggles loses the ability to see what is actual around him or her with any remaining sight. This is a disadvantage because a person wearing VR type googles and some AR glasses, which use wave guides that mechanically necessarily restrict the peripheral view, cannot completely see how to move in their environment, walk, or navigate steps or the immediate environment around him or her, so that the display is only potentially useful when sitting or remaining stationary. This causes any user to have to remove the goggles from their eyes to be able to receive actual visual clues from the real-world environment; a serious limitation of this type of application. Another limitation with these type VR goggles or AR glasses is that they do not bear an accurate relation to the real world a person might see, as the field of view is too small, and a patient wearing these type of VR goggles may experience motion sickness versus real world vision, due to blur, whirr, and latency.

Since the peripheral receptors in the retina are usually still functioning, it is the purpose of this invention, in one embodiment for the medical application of AR glasses, then, to stretch, skew, and manipulate the image being projected on the eye to avoid the macula, and be directed to the retina's peripheral receptors. In this way, the entire image is projected on the functioning retinal receptors, and any involvement of the macula is avoided. The method taught in this invention is how to create a matrix distortion of the entire image and project it onto the periphery of the eye, while avoiding the macula.

However, by combination of hardware, software, and firmware, as taught herein, the patient, by using "see through" glasses or lenses that provide a wide field of vision, upon which an augmented image can also be displayed, can have both real world and augmented visual information which corrects for the vision defect suffered delivered to the eyes. This is an improvement to the existing art and a new "Mixed Reality" wearable invention.

Under the teaching herein, the visually impaired patent can be introduced to both real world visual information and augmented information, at the same time, such that together the two separate inputs provide a "mixed reality" vision. This can be accomplished, as taught herein, with virtually no latency, such that the augmented enhances the user/patient's remaining real-world experience eyesight. Under this patent, the patient can still see some real world visual information with their peripheral eyesight so that the patient can move, walk, and navigate his or her immediate surroundings with as much surety and safety as the patent would otherwise have, and at the same time rely on the augmented reality of an augmented pixel/image moved video feed.

The present invention is aimed at one or more of the problems identified above.

SUMMARY OF THE INVENTION

In general, in a first aspect, the invention relates to a vision corrective wearable device which, in its preferred embodiment, uses Mixed Reality type of glasses/lenses together with new software and hardware to achieve the desired effect. This patent teaches to manipulate an image or video to avoid unsighted areas, such as the damaged areas that result with macular degeneration or macular hole, and project the image on the glasses lenses where it can be viewed by the next nearest sighted areas of the eye. It also teaches to merge such augmented video back into real world images which can be viewed alongside the real-world images received without video by, typically, the periphery of the naked eye. It also teaches to correct for nearsightedness and farsightedness at the same time as the correction of the central vision.

It must be remembered that the entire retina is the light and color sensitive tissue that lines the inside of the eye. As such, the retina functions in a manner similar to film in a camera, hence this invention supplements the retina's camera effect by providing an augmented, Mixed Reality duality of vision to the patient using both external camera(s) and display, as well as the eye's natural vision. Because it is important to make the augmented video or image hit as many cones as possible, the higher the rate of resolution, the better. In addition, the preferred embodiment of the invention the display would cover at least 50 degrees of the Field of Vision (FOV) or greater. Although, the invention will work with a lesser FOV also.

Thus, in one aspect of the invention the image to be displayed covers over the entire 120 degrees of normal eye vision, while in another aspect of the invention, the image is displayed on 90 degrees, 80 degrees, or 50 degrees FOV. The greater the FOV of the manipulated video display, the better reintegration of the real world in the exterior periphery of the eye's vision.

The image to be displayed is intended to be displayed on all or a portion of the lenses of Mixed Reality glasses, goggles, or other display techniques, where is extant both video and normal vision.

Part of the duality of the vision is the real-world vision that the patient sees where there is no augmented modified video, typically on the periphery of the lenses of the glasses and beyond that, simply the user's own unrestricted vision. The other portion of the duality of vision is the augmented, modified video or picture which is typically, in the case of macular degeneration, focused on the portion of the eye closest to the central vision, concentrating manipulated pixels and images onto areas that are still sighted, and avoiding areas that are unsighted. Together, these make up a Mixed Reality augmented reality vision which helps correct for the defect of eye diseases like macular degeneration (all of which eye diseases are referred herein sometimes as "defects" or "deficits").

In its natural state, the optical elements in the eye focus an image onto the retina of the eye, using the lens, initiating a series of chemical and electrical events within the retina. Nerve fibers within the retina receive these signals and send electrical signals to the brain, which then interprets these signals as visual images. In fact, all of us "see" an image upside down, since the eye bends the image through the lens, and the brain has the unique ability to "upright" the image in brain implemented natural simulation. This invention uses this natural "simulation" created by the brain to "see" a whole picture or video, without any part missing, when in actuality there is a portion of the lens, which does not display an image.

Thus, this invention also employs the "brain-stitching" theory behind the natural blind spot, scotoma, or punctum caecum, which naturally exist in every human's eye. This naturally occurring "hole" is the place in the visual field that corresponds to the lack of light-detecting photoreceptor cells on the optic disc of the retina where the optic nerve passes through the optic disc. Because there are no cells to detect light on the optic disc, this part of the eye's Field of Vision (FOV) is naturally occurring as unsighted and invisible to the human eye, as no visual information can be captured there. However, it has been recognized for a long time that some process in our brains interpolates the blind spot based on surrounding detail and information from the same eye or the other eye, and "fills-in" the blind spot with visual information so similar that we do not normally perceive the blind spot.

This invention teaches that by removing and displacing pixels or images of pictures or video from a non-sighted portion of a defective macula to the area just surrounding the damaged portion of the macula, the brain will interpret the image as a whole, and dismiss the actual hole that is cut into the picture or video. Computing software and chips create a modified camera generated display image which corrects for the missing macular portion of the retina by not projecting any video or picture on the unsighted areas, and instead displaying the entire image or video on all remaining sighted areas.

This invention has discovered a new concept for the correction of defects like macular degeneration which supposes and enables the brain-stitching/natural brain simulation theory. It has been proven on one notable patient, Brig. Gen. Richard C. "Dick" Freeman (U.S.A.F. Ret.) who is one of the inventors here and one of the inventors who first invented streaming mobile video. General Freeman had macular degeneration, and upon wearing a device using the invention and its augmentations, could instantly "see" a nose on a face, which, due to the macular degeneration, has not been visible for years. The brain-stitching was, in his case, instant, and did not need to be "learned" by the brain.

Thus, in one embodiment of this invention, there are up to four distinct "phases" of visual images a user would experience. These Four Phases are called the Image Manipulation Techniques (IMT) herein. In actuality, the invention works with less than the four, but the most suitable involves all these four. For instance, with Virtual Reality googles, only the First and Second Phases would be necessary. Just these two steps could be applied to Mixed Reality and Augmented Reality hardware. However, looking at the preferred embodiment, the example of the Four Phases is explained.

The First Phase of the Image Manipulation Techniques is the "hole" of diverse shapes and sizes, resembling as closely as possible the user/patient's own defect which is virtually "cut" into the picture or video through software techniques, to be displayed to the lenses for the eyes to view. Here, in this First Phase, there is no video or image display, except what the user might see with the naked eye and with the existing defect.

The Second Phase IMT is the augmented reality video display which contains the Pixel Mapping, Interpolation, and Synthesis. This is the area where the pixels which have been "cut out" of the video or image are repositioned to the nearest adjacent area of the eye. These pixels and subpixels are repositioned on the area directly around the defective area of the eye, and the brain, like the case of the punctum caecum fills in the "hole" with the visual information added to the surrounding area. In another embodiment of the invention, the image is displayed directly onto the eyes through techniques like retinal projection. And again, in another embodiment of the invention, the display is directly on the eye by virtue of Smart Contact Lenses, which can create a display on a contact lens covering the eye.

This manipulation of pixels or image, whether of a picture or video, of course, presents itself with more than 100% of the visual information which must be displayed onto the immediate adjoining areas of the eye. One method to have more than 100% of the image or video displayed on 100% screen is to interleave the video, rather than have it display progressively, where on one scan the original image is shown, and on the alternative scan the repositioned pixels are shown. In another embodiment, a simple reduction of the image occurs. This is necessary because a part of the image or video has been "cut out" in software and repositioned on the next adjacent space to the deficit in the eye. In another embodiment, the method to displace and replace more than 100% of information is accomplished with pixel mapping and replacement. This pixel mapping and replacement occurs after the camera has acquired the image or video and the buffering begins. This manipulation typically takes place in the Central Processing Unit (CPU) of a micro circuit; and more specifically in the Graphics Processing Unit (GPU) occasionally called the Visual Processing Unit (VPU). These GPU "chips" are specialized electronic circuits designed to rapidly manipulate and compress/decompress video and alter memory to accelerate the creation of images in a frame buffer intended for output to a display device. Speed is key here, as any latency will be evident in the display to the eye. With proper software, most of the modern GPU's can be configured to have only a 1 millisecond delay, between acquisition of the image or video, manipulation of the pixels and the display of the video, which the eye can easily accommodate and absorb in the display with little or no affect. However, to accomplish the requisite video compression and manipulation both the CPU and the GPU may need to be used and functions separated and an ASIC, which is an Application Specific Integrated Circuit, may be used to help combine the necessary CPU and GPU functions. The CPU and the GPU work together, however, to accomplish the task and may need other parts on a circuit or circuit board to fully perform, such as capacitors, resistors, input/output connectors, circuitry, and the like.

It can be recognized that in many instances, since the area of defect is typically not expressed in a standard form, like an oval or circle, that there also must be algorithms which instantly measure how far away a pixel would have to be moved to go upwards, downwards, to the left side or to the right side, or transversely from the original area in which the pixel resides. Thus, a measurement may be taken from the area of defect (non-sighted) to determine which way to move the pixels, up, down, to the left or right sideways, or transversely such as up and left or down and right. The software and algorithms may be programmed to move the pixels to the closest original place where there is sight, whichever way the need to me moved. Thus, two pixels or parts of an image which were originally exactly adjacent to one another on any axis up/down, sideways, or transverse, may be moved together one way, or, if one pixel or part of an image is closer to one border than to the other, the pixels may be split with one pixel or image going to its closest border and the other pixel going to its closest border which is the essence of corrective subpixel mapping and modification.

The cutting of the "hole" and repositioning of the video or image may be accomplished primarily by stretching the pixels to a larger overall area than the original captured image (i.e. 100° stretches to 120° overall space, but the center 10° is cut out). In this method all the pixels are still there, in relatively the same size and shape, as originally captured and buffered by the camera(s), except either the far edge boundary has been extended or cropped. This method works well with Virtual Reality goggles, but not as well with Mixed Reality improvements in the technique. Thus, the preferred method in Mixed Reality Corrective Glasses (MRCG) is to use Pixel Mapping, Interpolation, and Synthesis (PMIS). Under this method the pixels in the area of the display to be avoided are mapped, in real or near real time, within or without a buffer, and software algorithms keep the same shape of the image, but reduce the size of the pixels to subpixels, such an image which was, for instance, shown on four pixels, is now shown on three, two, or just one. The resulting display has all the visual information, just displayed using a fewer number of pixels and subpixels. Under this method pixels have been reduced to subpixels, which have been moved in the video according to the software implementation and the shape of the defect. In this way the pixels and the image that are moved do not necessarily have to have a specific "boundary" like an oval or a circle, but the pixels can be removed from any defect area, no matter how irregular and repositioned to a sighted area just adjacent. Thus, the idea is not just one where boundaries are created, but where the image or video pixels are moved one by one out of the non-seeing, defect area to another location as close to that unsighted area as possible with the remaining image being likewise transposed to make room for the removed and replaced pixels and image. Thus, the area to be avoided may be very irregular and complex, which makes no difference, as once it is mapped, pixels are removed from the space where no sight is and placed as closely adjacent to the place on the pixel map as possible, which is described herein as subpixel mapping and placement.

Pixels as used herein are perceived spaces where subpixel mapping is a recently developed technology involving algorithms to obtain and map the spatial distribution information of area covered within mixed pixels and then reposition them on a smaller or different scale. See, FIG. 25. Algorithms can be applied to pixel mapped video or image content, and images moved from one location in the video to another wherein the shape may not be a homogenous shape like a circle or oval. In some instances, the pixels or subpixels must be "distorted" in order to have 100% of the image included into 100% of the display space. In this case the pixels or image take on a shape which is not a typical pixel square, but can be something besides a square, and often more like a tetrahedron or polyhedron, or shapes like triangles or parallelograms.

Under this method, the classification on a per pixel basis is established and then reconstituted in a pixel/subpixel format to achieve subpixel mapping for modification. By applying known pixel and subpixel mapping techniques, as well as the ones invented by the inventors here, an image or video can be displayed with augmented pixel/subpixel manipulation and stitching so that a whole image exists, just not in the original place as the camera input originally assigned.

Next is the Third Phase, where video is faded back into reality video through "stitching" or similar techniques which are used to merge combine the Second Phase with the Third Phase in steps where the Second Phase is "phased out" and the Third Phase of real world captured video dominates. In this Third Phase, direct camera input is a phased-in re-engagement of the real world projected image. In the Third Phase, the Second Phase Image Manipulation Technique merges with the Third Image Manipulation Technique to phase out the 100% pixel manipulation. This Third Phase works the other way to reintroduce the image or video back to 100% of what the camera actually acquires as an image. However, in this Phase, the video may still be manipulated so as to correct for line-of-sight (to correct for the what the eye sees versus the camera captured images) and to correct for the epipolar geometry effect of the eyes moving inward and outward/straight.

This Third Phase software/hardware stitching is akin to the techniques commonly utilized in 3D video stitching software. It is in Phase Three where the augmented video is then returned to an un-modified video of what the user would actually "see" if the cameras were projecting and displaying raw, unmodified video or images. This "raw" video is projected or displayed on the retina, contacts or lenses of glasses where only a portion of the Field of Vision is used for Phases One through Three and the rest of the display area is reserved for Phase Four video, where it can be merged by the eye and brain with the real-world vision which is external to Phase Four.

Further, Phase Four is where the user sees with his or her peripheral vision the real world and upon which either the sight through the lenses or beyond the lenses, no video is displayed. This Phase also includes any extra peripheral vision that is extant outside of the glasses, lenses, contacts, or retinal projection, and provides the user with additional real-world ques and images.

Thus, by using Phases One through Four, a user experiences four distinct image sets, all of which merge through the brain's natural simulations to create one Mixed Reality view of the world, which is corrected for the defect. Thus, on a display of see through glasses there is projected an augmented video, which could be as large as 30-50 degrees Field of Vision or more. This could be greater or smaller depending on the type of defect and the amount of correction. Outside that augmented video display on the lens is displayed a video of what the eyes would ordinarily see, but augmented in a phase-in/phase-out of the augmented video.

In another embodiment of the invention, an implanted lens, or lenses, akin to an implanted intraocular lens, performs some or all of the pixel manipulation by diverting pixels away from the damaged areas of the macula. This could be done with dual lenses like those used in Intraocular Lens for Visually Impaired Patients (IOLVIP or IOL-VIP) which is an intraocular lens system aiming to treat patients with poor central vision due to age related macular degeneration. The IOLVIP procedure involves the surgical implantation of a pair of lenses that magnify and divert the image using the principals of the Galilean telescope. By arranging the lenses, it is possible to direct the image to a different part of the eye than the fovea. In this way the glasses, frame and headgear (GFH) and external display would be calculated to coordinate with the implanted lenses to cut out the image ordinarily displayed where the defect exists and project the full image on the display, which is then diverted by the implanted lenses and becomes a full image. This is unlike the IOLVIP lenses are used now, which only carry a portion of the actual image information.

In addition, in one embodiment, this invention comprises a system having a database, a CPU, a model controller, a camera intake, a display controller, and a display unit. The model controller, which may be hardware, firmware, software, memory, microcontroller, state machine, or a combination of any of the forgoing, is coupled to the database and is configured to establish a reference to a visual model associated with a patient's visual defect; then the camera(s), one or more, take a picture or video of the actual image and the software makes corrections for the patient's visual defect and then the corrected/modified image is displayed which has been corrected for the patient's visual defect.

In summary of the invention, one or more cameras and lenses are enabled to assist the patient in identifying one or more of his or her visual impairment boundaries, and then transferring this information into the Visual Modification Program which augments the displayed video to displace video and picture images to displace the part of the image within the vision impaired boundaries and replace it to the nearest sighted area. In one embodiment of the invention, the Visual Modification Program also re-introduces real world images captured by a Camera Input System (CIS) so that an augmented video segment is displayed on the lenses, wherein the augmented video segment is phased back to a real-world, un-modified video, so that the "edges" of the displayed system are in sync or near sync with the real-world vision seen by the eyes. The invention also includes a method to store the modified visual model in the database and to project it on a display. The invention also includes a Diagnostic Impairment Mapping (DIM) System and method to capture information about the area and location of the eye defect. An example of this would be mapping an area where macular degeneration has occurred and little or no sight or vision remains. The corrected visual model includes data related to the quality of the patient's vision and the manipulation of images and/or pixels or other visual portions of a video or recorded image or images which correct for that patient's visual defect. In one embodiment, the corrected image is not a manipulation of pixels, but a mapping of pixels in software/firmware including a step of correction for the patient's visual defect through repositioning of the image onto other pixels or subset of pixels which are then projected onto the sighted areas of the eye, such that a whole picture or video is shown, but the portion of the eye that is defective is left with no image/video projection. As used herein when the word or term picture, image, or video is used it shall mean all or any one of the same.

BRIEF DESCRIPTION OF THE DRAWINGS

Non-limiting and non-exhaustive embodiments of the present invention are described with reference to the following figures, wherein like reference numerals refer to like parts throughout the various views, unless otherwise specified.

Figure 1:
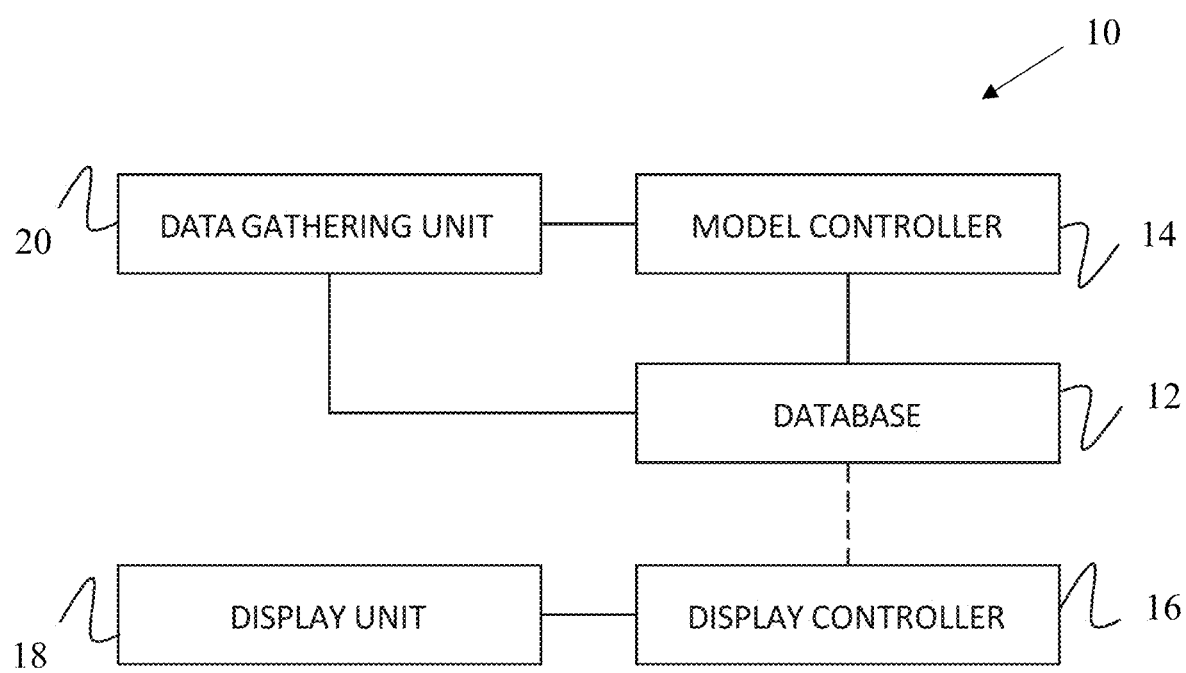
FIG. 1 is a block diagram of a system to augment a patient's vision, according to an embodiment of the present invention.

Other advantages and features will be apparent from the following description and from the claims.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification. It will be apparent to one having ordinary skill in the art that the specific detail need not be employed to practice the present invention. In other instances, well-known materials or methods have not been described in detail in order to avoid obscuring the present invention.

Reference throughout this specification to "one embodiment", "an embodiment", "one example", or "an example" means that a particular feature, structure or characteristic described in connection with the embodiment or example is included in at least one embodiment of the present invention. Thus, appearances of the phrases "in one embodiment", "in an embodiment", "one example", or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art, and that the drawings are not necessarily drawn to scale.

Embodiments in accordance with the present invention may be embodied as an apparatus, method, or computer program product. All of the Systems and Subsystems may exist or portions of the Systems and Subsystems may exist to form the invention. Accordingly, the present invention may take the form of an entirely hardware embodiment, an entirely software embodiment (including firmware, resident software, micro-code, etc.), or an embodiment combining software and hardware aspects that may all generally be referred to herein as a "unit", "module" or "system." Furthermore, the present invention may take the form of a computer program product embodied in any tangible media of expression having computer-usable program code embodied in the media.

Any combination of one or more computer-usable or computer-readable media (or medium) may be utilized. For example, a random-access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present invention may be written in any combination of one or more programming languages. Further, the intelligence in the main circuitry may be software, firmware or hardware, and can be a microcontroller based or included in a state machine. The invention may be a combination of the above intelligence and memory and this can exist in a Central Processing Unit or a multiple of chips including a central graphics chip. The computer portion of the invention typically also includes a Model View Controller.

The flowchart and block diagrams in the flow diagrams illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable media that can direct a computer or other programmable data processing apparatus to function in a particular manner, such that the instructions stored in the computer-readable media produce an article of manufacture, including instruction means which implement the function/act specified in the flowchart and/or block diagram block or blocks.

Several (or different) elements discussed herein and/or claimed, are described as being "coupled", "in communication with", "integrated" or "configured to be in communication with" or a "System" or "Subsystem" thereof. This terminology is intended to be non-limiting, and where appropriate, be interpreted to include without limitation, wired and wireless communication using any one or a plurality of a suitable protocols, as well as communication methods that are constantly maintained, are made on a periodic basis, and/or made or initiated on an as needed basis.

The disclosure particularly describes a system, a method and computer program instructions stored in media, that augment the sight of an individual or patient whose sight has been damaged or is otherwise defective. In general, the present invention provides techniques that may be implemented in systems, methods, and/or computer-executable instructions that (1) map the defective areas of the patient's sight, (2) establish one or more boundaries that delineate between the effective and defective areas of the patient's eye(s), (3) capture an image (or series of images) using a camera associated with the patient, (4) map the capture image (or series of images) and generate a corrected image (or series of images), and (5) present the correct image(s) to the patient's eye(s).

With reference to FIG. 1, an exemplary system 10, according to one embodiment of the present invention, is illustrated. The system 10 includes a database 12, a model controller 14, a display controller 16, and a display unit 18. As will be discussed in more detail below, a data gathering unit 20 is used to gather data that may be used to develop a visual model of the patient's eyesight. The data used to establish the visual model, the visual model and other data is stored in the database 12. Since the peripheral receptors, in the macular degeneration case, in the retina are usually still functioning, the present invention stretches, skews and/or otherwise manipulates the image(s) presented to the eye(s) of the patient to avoid the macula or the damaged portions of the macula. Thus, the entire image is presented to, or onto, the functioning retinal receptors. As explained in more detail below, the present invention creates a distortion map of the image and displays it, or projects it onto the periphery of the eye(s), while avoiding the (damaged portion of the) macula. The distorted image is presented to, projected onto, the eye using (high definition) goggles, glasses, a "smart" contact lens, or a photon projection (using a virtual retina display) of the image directly onto the periphery of the eye.

In general, the model controller 14 is coupled to the database 12 and is configured to establish the visual model associated with a patient and to store the visual model in the database. The visual model includes data related to a quality of the patient's vision. The model controller 14 is further configured to establish a boundary as a function of data associated with the visual model. This process is discussed in further detail below. The boundary is indicative of an area to be corrected within the patient's vision. The model controller is further configured to establish a retinal map as a function of the boundary and to store the retinal map in the database.

The display controller 16 is configured to receive and to store the retinal map. The display controller 16 is further configured to receive an image (or series of images) from a camera, such as a video camera, (see below) associated with the patient and to apply corrections to the image(s) based on the retinal map and responsively generate corrected image(s).

In one aspect of the present invention, one or more macular or retinal maps may be generated. These maps may be associated with predefined settings, for examples, day time, night time, reading, or watching television. The correct retinal map may be automatically selected for specific conditions and/or may be user selectable to fit changing conditions.

The display unit 18 is coupled to the display controller 16 and is configured to receive the corrected image(s) and to present the corrected image(s) to the eye of the patient. It should be noted that the present invention may be configured to present corrected video, as a series of images, to the eye of the patient.

In general, the model controller 14 and database 12 may be an embodiment, in a computer, specific or specifically designed hardware or apparatus, and application specific integrated circuit (ASIC) server, or servers operating independently, or in a networked environment. The data gathering unit 20 (described in further detail below) may be linked, at least temporarily, or may be data transferred over a network, electronically, or through a physical media.

In one aspect of the present invention, the retinal map may be established automatically and adjusted (with or without the patient's specific update permission) at or by the model controller and then transferred electronically to the display controller.

In another aspect of the present invention, the model controller 14 may establish a plurality of retinal maps that vary in either the parameters used to generate the retinal map and/or the method used to generate the retinal map. The plurality of retinal maps may be stored at the display controller 16. The patient may then cycle through the retinal maps and select, for use, one of the retinal maps that works best. For instance, a particular retinal map may work best for the instant conditions. Thus, the patient may select a retinal that works best for the conditions which currently exist.

As discussed more fully below, the display controller 16 and the display unit 18 may be embodied in a head mounted display, goggles, or glasses that are mounted to, or worn by the patient. Alternatively, the display controller 16 and display unit 18 may be embodied in a unit that is separated from, i.e., not worn by, the patient. One or more sensors (not shown) may be utilized to find the location and distance of the patient relative to the display unit 18 such that the image may be displayed properly.

Each eye of the patient is different and typically has a unique defect. For instance, one eye of the patient may have a specific defect (having a specific shape, size and location), while the other eye of the patient may not have a defect or may have a defect having a different shape and size. Thus, each eye of the patient will generally be mapped and a respective visual model of each eye established. A border of the defect of each eye will be generated and an associated retinal map generated. In one embodiment, separate cameras will generate a separate set of images for each eye and the display controller 16 will generate a respective series of images to be presented to each eye. Cameras should be of very high quality and 4K or 8K cameras and projection will provide the best results.

Figure 2:
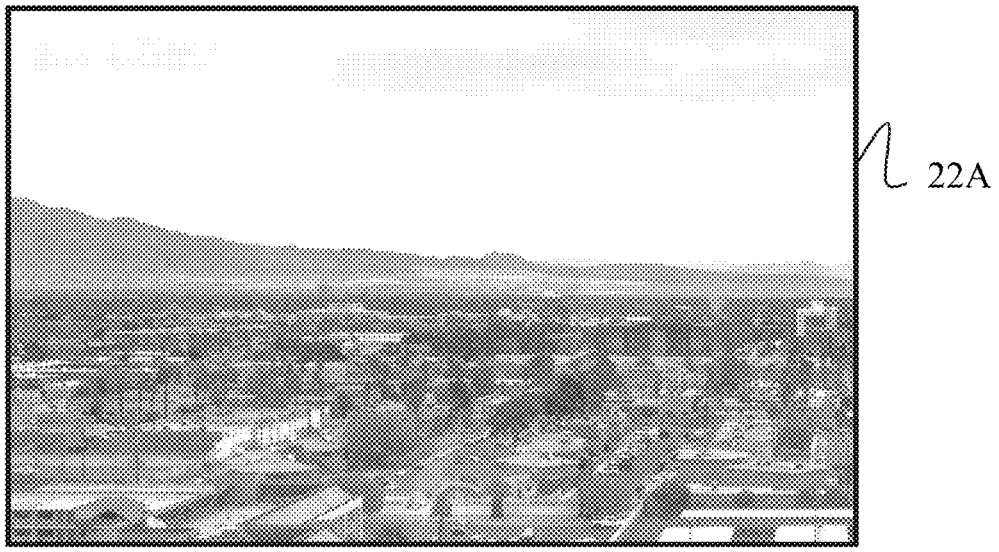
FIG. 2 is a diagrammatic illustration of a patient's vision without a defect.
Figure 3:
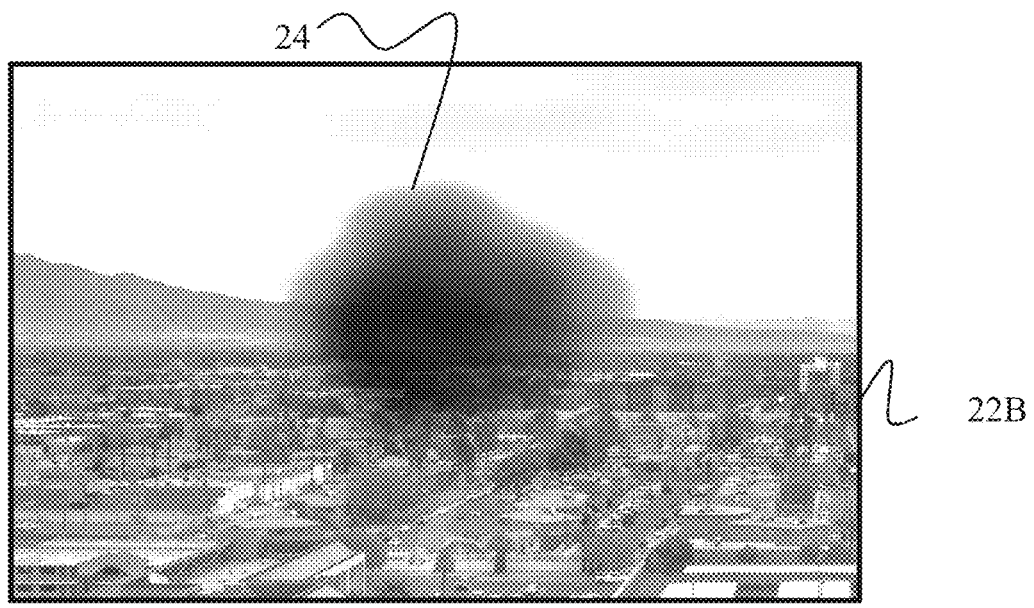
FIG. 3 is a diagrammatic illustration of a patient's vision with a defect.

With reference to FIG. 2, a graphic 22A representing the vision of a patient's eye without a defect is shown for purposes of comparison. With reference to FIG. 3, a graphic 22B representing the vision of a patient's eye with a defect is shown. The defect is represented by the dark shape 24 shown in the center of the graphic 22B.

In one aspect of the present invention, the visual model may be established using the data gathering unit 20. The data gathering unit 20 may include at least one of (1) a field of vision opthalmological instrument, (2) a portable mobile field of vision test apparatus, and (3) a computer-based system. The process of gathering data using the data gathering unit 20 is discussed in more detail below.

Figure 4A:
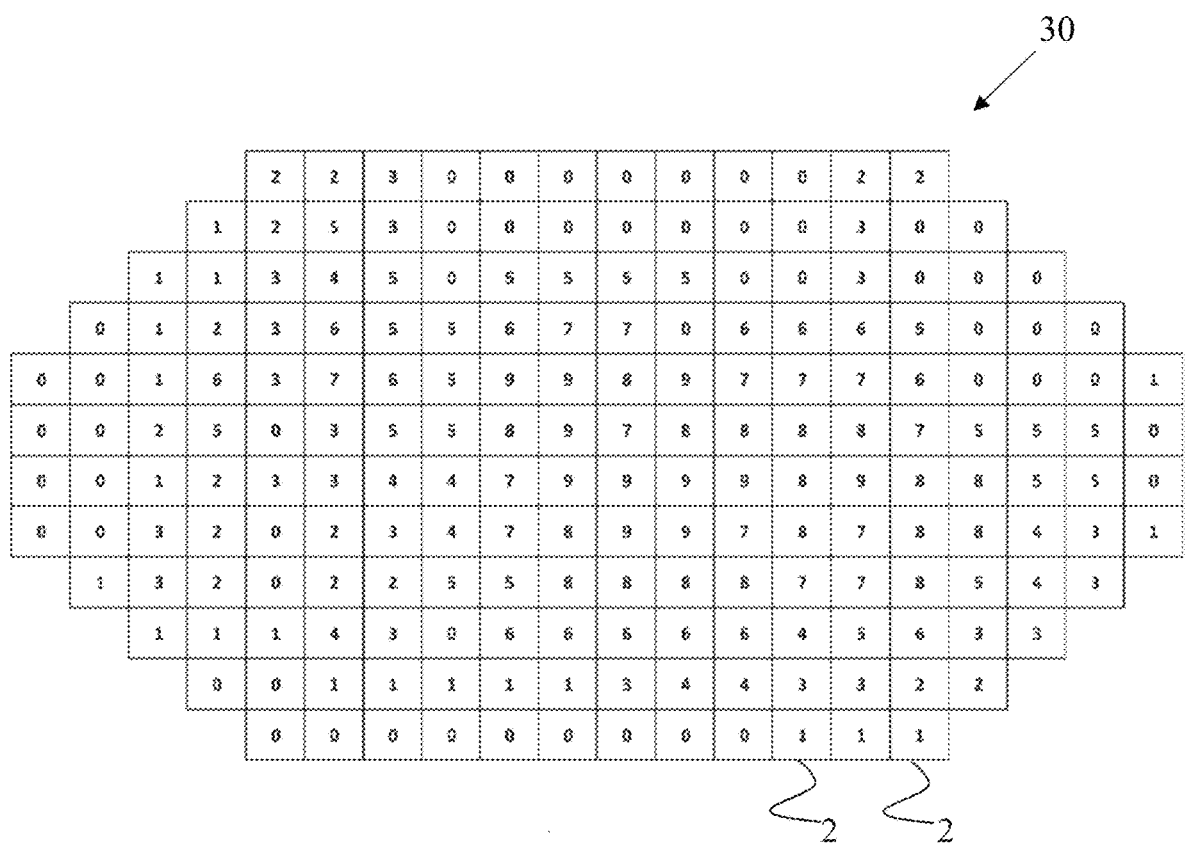
FIG. 4A is an illustration of a sample visual model, according to an embodiment of the present invention.

With reference to FIG. 4A, a simplified example of field of vision (FOV) data 26 is shown. The FOV data 26 is used to create the visual model. The FOV data 26 includes a plurality of cells 28 arranged in a grid 30. Each cell 28 has an associated value associated with the quality of the patient's vision. The values may be based on an absolute or representative scale that is indicative of the quality of vision. Alternatively, the values may be a deviation from a standard value, or a value of an associated cell. For purposes of explanation, in the exemplary FOV data 26 of FIG. 4A, the values in the grid utilize a scale of 0-9, where 0 represents no defect, 9 represents a defect and the values 1-8 represent a quality of vision between 0 and 9. It should be noted that a scale of 0-9 is for discussion purposes only. The scale utilized may be any suitable scale, for example, 0-99, 0-255, −30 to 30, or any suitable scale. Furthermore, the illustrated grid having 12 rows and 20 columns. The shape of the grid may be used to approximate the shape of an eye and may be different between the left and the right eye. However, the size and the shape of the grid may be based on a 12×20 grid, however, any size grid may be utilized. The size of the grid may be dependent upon the data gathering process, or data gathering unit 20 and/or the display unit 18. In another embodiment, the FOV data may be represented by a contour, polygon or morphological operator.

Figure 4B:
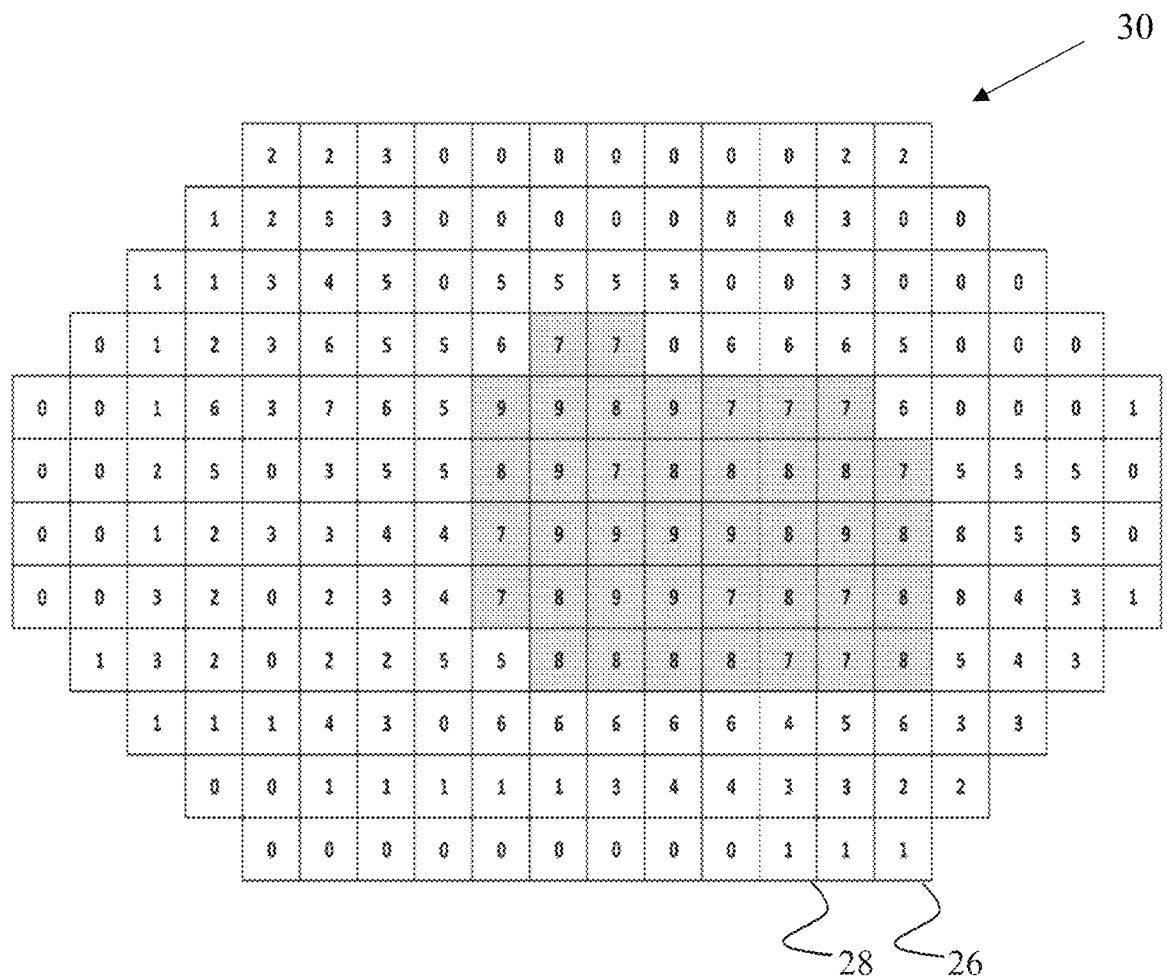
FIG. 4B is an alternative view of the sample visual model of FIG. 4B.

The boundary may be established as a function of the values associated with the cells in the grid. In one embodiment, the values in the grid values are compared with a threshold to establish the boundary. For example, in the above example, the threshold may be set to 7. Thus, any cell 28 having a value of 7 or greater is within the boundary and any cell 28 having a value of 0 is outside of the boundary. A modified view of the FOV data 26 is shown in FIG. 4B, in which the cells 28 meeting the above threshold are highlighted.

Alternatively, the FOV data 26 could be used to create a contour. The visual model emerges from interpreting the raw data and is not necessarily a point-by-point transformation of the raw data. The intent is to put the removed pixels as close to where they ordinarily would have been, thus, the algorithms in the software determine, based on (i) the whole of the defect, (ii) the distance of the specific pixel or ray from the border of the defect, (iii) whether a pixel is a new image or a part of an existing image (meaning whether the pixel is a part of an image or on the border of an image change), (iv) the other options for the pixel to move another way, and (v) where the adjacent pixels to be adjusted are being moved, exactly where to move such pixels/rays.

In another embodiment of the invention, vector images are used. For the purpose of this patent, vector images and pixels are used interchangeably. However, in practice unlike digital images which are made up of (usually) millions of tiny squares or other shapes known as pixels, while vector images are made from mathematical points connected together by lines and curves to create different shapes. Since they are based on math and algorithms, not merely pre-placed pixels, vector shapes are extremely flexible and do not suffer from the same limitations as pixels.

There are five (5) major Systems, and a number of Subsystems which are a part of the complete invention. One or more of the Systems or Subsystems may be combined, omitted, or integrated.

The first major system is the glasses, frame and headgear ("GFH"), which typically is worn on the head of a user and positioned over the eyes and nose like typical glasses. The GFH houses the cameras, the microcontrollers, the connectors, and Subsystems which are comprised of sensors, such as motion sensors, six or nine Degrees of Freedom sensors (up/down; back/forward; left/right; pitch/roll/yaw), gesture recognition sensors, fiducial marker sensors, accelerometer sensor, infrared sensors, motion sensors, alert sensors (which would alert a user to a danger), gyroscope technology and related sensors, positional tracking sensors (including Wi-Fi location systems, mobile locations systems, and RFID location based systems), sound sensors, and optical sensor technologies. The sensor array also can include mechanical linkages, magnetic sensors, optical sensors, acoustic sensors, and inertial sensors. This list is not exhaustive, but illustrative of the type of sensors located on the GFH. The GFH also houses virtual environment (VE) Subsystems such as: (1) head and eye tracking for augmenting visual displays; (2) hand and arm tracking for haptic interfaces to control virtual objects and aid in the diagnostic tools; (3) body tracking for locomotion and visual displays; (4) environment mapping interfaces to build a digitized geometrical model for interaction with sensors, diagnostics, and simulations. Other sensor technologies typically housed on the GFH are the digital buttons, which would include the power buttons and a D Pad or Control Pad for accessing and controlling functions by the user. The sensors listed above include their operating systems and output. The GFH also houses the connectors such as power connection for recharging a battery or for direct connection to and AC source, as well as other connectors for HDMI, sound, and other input/outputs, such as additional image overlay display, or for a diagnostics protocol for upgrading the system.

The GFH also houses the Microprocessor(s) Control Circuits (MCC) which are described below.

The GFH may also include a strap and counterweight or other headgear to balance the GFH and maintain its position on the head. In addition, the GFH may include a "dongle" whereby one or more of the Systems or Subsystems are connected via wire or wireless to another device, such as could be worn on a belt or carried in a pocket to reduce the overall weight of the GFH.

In one embodiment, the GFH is connected to another device which is providing power, while in an alternative embodiment, the GFH has its own power from the Mains or from wireless power transmission or from a battery. Further, in another embodiment, the GFH houses the cameras, the microcontrollers, the connectors, Central Processing Unit, Graphics Processing Unit, software, firmware, microphone, speakers, and subsystems.

In another embodiment, the GFH contains an RFID reader to read signals from RFID tags. In another embodiment, the GFH contains optical character recognition/reader sensors to read information from the real world.

Alternatively, some parts of the system mentioned herein are in a dongle attached to the GFH via wire or wireless connection. Alternatively, some portions of the system mentioned herein are contained in a connected device, like a laptop, smart phone, or WiFi router. Alternatively, some parts of the system mentioned herein are contained in a remote location and accessed by the GFH via Radio Frequency (i.e. cellular bands) or other wireless frequencies or via wireline. Thus, in one embodiment of the invention, multiple heads-up displays on the same headgear or on the headgear of multiple wearers are connected through a wire or wireless network in order to develop or control information which can be shared with the other users. This would be accomplished by having the GFH gather information from the cameras or sensors processing the information through preset filters and distributing the information to all the other GFH would have the ability to control the information or share the information with all the other GFH connected to the network. In another embodiment of the invention the information could be gathered from a remote location or library and shared with other HDC through an intermediate source like a smart phone or laptop.

The GFH also contains the battery and receipt charging DC Subsystem or alternatively, an AC input and converter to connect directly to an AC source; as well as the wire and wireless Subsystems to connect or pair the device to other systems, such as sound, alert systems, fall monitoring systems, heart monitoring, other vital sign monitoring, and various APPs programs, cloud computing and data storage. Other Subsystems in the GFH are a microphone/speaker and amplifier system, an integrated Inertial Measuring Unit (IMU) containing a Three Axis Accelerometer, a Three Axis Gyroscope and a Three Axis Magnetometer, or things like an Auxiliary port for custom sensors such as range finder, thermal camera, etc.

Other Subsystems like Bluetooth for near connectivity to cell phones, tablets, automobiles, and the like can be included as well as Global Positioning Systems or interior tracking systems like RFID, Wi-Fi, or Cellular tracking location based directional travel. Other communication systems can also be included based on either wire or wireless connectivity of the GFH. The GFH can also be connected wired or wirelessly to a main monitoring data system which would track the health, whereabouts, and condition of the user to be displayed to another person such as a caretaker or a health care provider.

In another aspect of this invention, there is no manipulation of the pixels for eye correction, rather, an AR headset which provides a computer mediated video shown on a display screen such that the wearer sees both the real world and the augmented video at the same time. In this aspect of the invention, such features as voice/speech recognition, gesture recognition, obstacle avoidance, an accelerometer, a magnetometer, gyroscope, GPS, special mapping (as used in simultaneous localization and mapping (SLAM), Cellular Radio Frequencies, WiFi frequencies, Bluetooth and Bluetooth light connections, infrared cameras, other light, sound, movement, and temperature sensors are employed, as well as infrared lighting, eye-tracking, and Dynamic Opacity are employed as set out following.

With what the inventors call Dynamic Opacity, one aspect of this invention solves the typical "heads-up" reflected display problem of visualization in bright light or sunlight conditions. In this instance, the GFH uses a bright display, typically for the highest resolution it could be a Quad HD AMOLED display, which is reflected onto the surface of a lens for the user to see the "virtual" portion of the display. In using a high-resolution AMOLED reflected display, the brightness can be adjusted up or down depending on ambient light. Alternatively, the adjustment can be in the system controller and automatically adjust depending on what the sensors say the brightness of the ambient light is, which would typically be brighter when in brighter exterior light. The AMOLED, OLED, or similar display can be one display or two displays, one for each eye as reflected on the lens.

In one aspect of the invention, a reflective coating is applied to the clear lens to enhance the reflectivity of the virtually displayed image. In another aspect of the invention, the reflective coating is not necessary because of the operation of the Dynamic Opacity subsystem.

Figure 30:
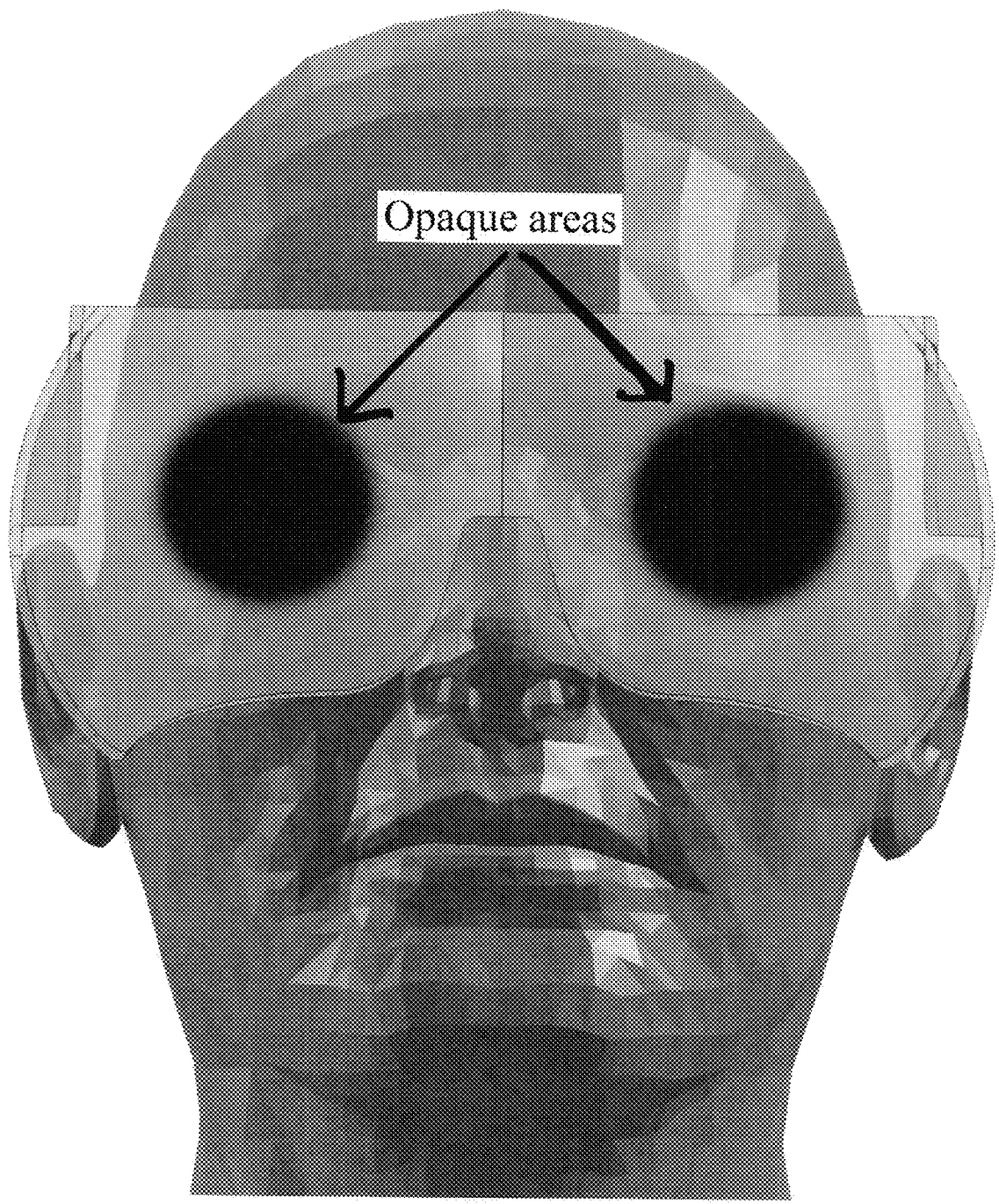
FIG. 30 is an illustration demonstrating dynamic opacity.
Figure 31:
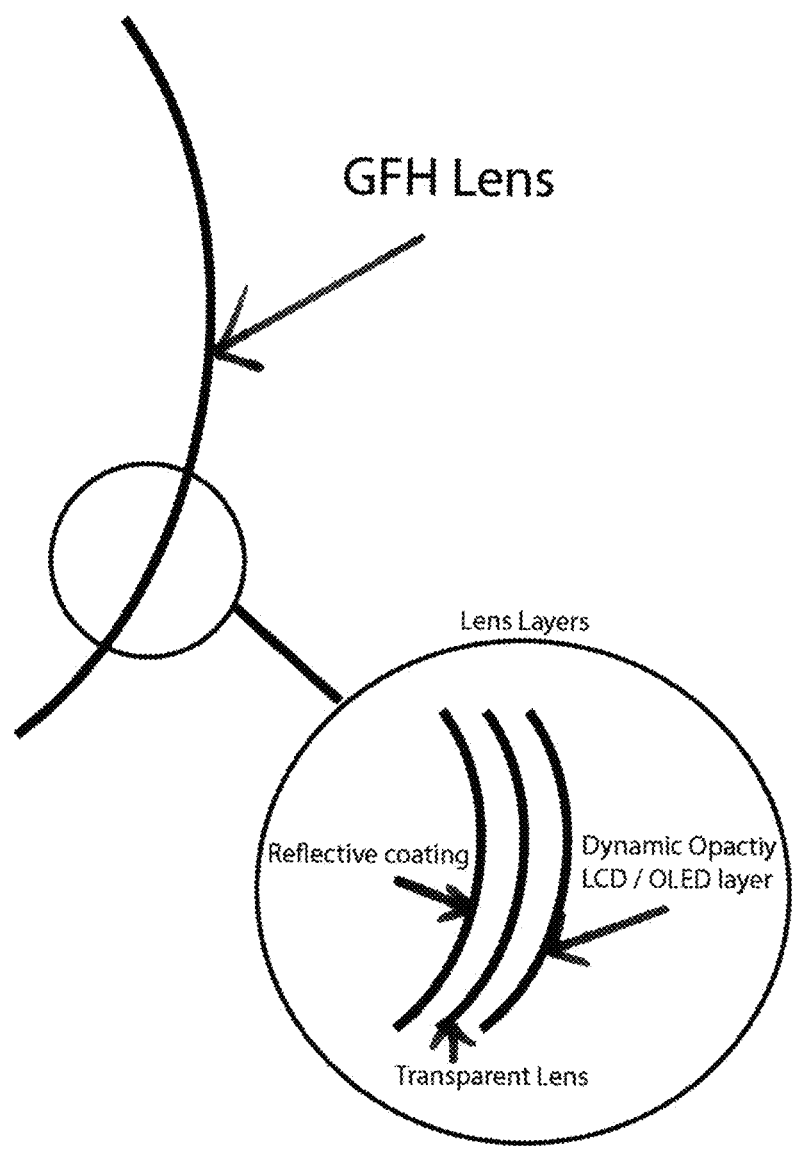
FIG. 31 is an illustration of lens layers.

The clear lens upon which the high-resolution display which may be a plastic like Lexan or other clear polycarbonate or glass or any other clear material, may or may not have a reflector integrated into the lens to improve visibility of the reflected display. In any case, the outside of the lens would also be bonded to a layer containing a Liquid Crystal Display (LCD) or Transparent OLED display which operates to obscure the outside light to provide greater acuity for the wearer viewing the virtual information displayed in high lighting conditions (Dynamic Opacity Display or DOD). An OLED transparent display can be quite clear, which makes reading fine details or text on objects behind the display possible until something is displayed on the screen in "virtual mode," meaning something from the streaming video reflected display is shown on the display/lens. Alternatively, a transparent/translucent LCD can be used as an outer layer or middle layer of the otherwise clear lenses, and either bonded together with the clear lens upon which the reflected display is to be projected, to create the Dynamic Opacity. Dynamic Opacity senses where the image is being projected on the interior of the lens and obscures from one percent or less to up to 100 percent of the otherwise clear lens. In this aspect, the clear lens may or may not be also coated with a reflective layer. See FIG. 30. The clear lenses can also have reflective material on the inside to increase reflectivity of the projected image, such that the base lens is not exactly clear, but is some percentage of obscured by the reflective film, paint, or other embedded reflectivity. See FIG. 31.

The Dynamic Opacity subsystem is controlled by the display controller and works in tandem with the information displayed. The display controller creates an image buffer for the projected virtual display, and this information is shared with the Dynamic Opacity controller, which then activates the pixels which correspond with the exact or near exact location where the display controller is projecting the virtual image, so as to make the portion of the reflective lens upon which the image display is being projected is likewise made opaque on the exterior of the reflective lens, so that the image displayed appears to be brighter due to the backlighting or light filtering provided by the Dynamic Opacity. The Dynamic Opacity subsystem works because the transparent LCD or translucent OLED contain some resolution of pixels, which in the instance of Dynamic Opacity can be a lower resolution than the projected display, and each pixel is controllable by the Dynamic Opacity controller, which gets its information of which pixels to activate from the display controller. In the OLED the activation of the pixels would be turning on the individual OLED RGB pixels in order to achieve the correct level of opacity to compensate for existing brightness for the condition experienced by the user. In this instance, the RGB pixels can be activated to create a "shadow" effect or depending on the type of light which is extant, an emphasis on either Red, Green, or Blue, or combinations of the three. In addition, the Dynamic Opacity subsystem can be pre-programmed to provide a user with various options from warm color to cold (amber to green) for a sunglass effect on the exterior of the reflective lens. In the case of the LCD the activation of the pixels is one or more phases and changing the polarization of the pixels to achieve opacity on the exterior of the glasses for the same effect. In this instance, typically, an LCD unit would be employed which does not include a RGB component, as just outside ray blocking is needed.

Alternatively, with Dynamic Opacity, any other transparent material which provides electronic control of pixels or areas inside the transparency to create an opaqueness can be used. In either case, the outer layer would typically be transparent to the user providing a "see through" lens to the real world, until some virtual information was displayed on the Head Mounted Display Unit reflective lens, such as a hologram, a 2D image like a movie, or other 3D image or information, including text.

In this embodiment of the invention, a controller, like Model View Controller (MVC), would control the Dynamic Opacity Display through corresponding data input information about where the reflective display is projecting information. In this instance the MVC would identify in the buffer or elsewhere, in digital format, where the images are going to be displayed on the reflective display, and the MVC would anticipate these locations and turn on pixels, including RGB pixels in the transparent LCD or OLED, and "cloud" or rather make more opaque the portions of the lens corresponding to the areas of the lens where the virtual image is being displayed on the inside or other layers of the reflective display. In this fashion, the Dynamic Opacity provides a "backdrop" or "background" display corresponding to the pixels where the virtual image is displayed making the contrast of the virtual display greater to the eye, so that brightness like natural sunlight can be minimized, which would otherwise compete with the reflected display and cause it to be hard to see. With the Dynamic Opacity, the reflected display has a buffer between it and exterior light, which gives the reflected display greater brightness to the eye.

The Dynamic Opacity could be in either a course or fine mode, meaning that the opacity from the Transparent OLED or LCD would either appear in the general area of the virtual display or for fine applications would appear in almost or the exact same pixels which correspond to the image pixels being displayed or reflected on the interior of the lens. In another aspect of the invention, the Dynamic Opacity can work with wave guide displays or prism type displays with equal effect. Likewise, the Dynamic Opacity described here can be used with a micro-mirror type display with equal effect.

There are many methods to identify exactly where the coarse or fine opaqueness should appear, but one embodiment would use the same eye-tracking as the primary display/lens and the MVC would know exactly where the eye gaze is and how far each way on a six way axis the virtual display is centered and extends, so that the opaqueness mimics the same space as the virtual display according to where the eyes are gazing as identified by the eye-tracking software. In this way, the reflected image display overcomes the issue of not being bright enough in daylight and other high light conditions. Likewise, the Dynamic Opacity includes transparent OLED or LCD overlay or layer of the lens can also act as "sun glasses" for the display and "tint" the entire display to compensate for bright lights, like on a sunny day. Or with similar effect, a light valve can be used with the same effect in a similar manner. A light valve (LV) is a known device for varying the quantity of light from a source, which reaches a target. Examples of targets are computer screen surfaces, or a wall screen or in this case the coarse or fine coverage of the virtual display on the glasses lens.

In the Dynamic Opacity technology, the MVC can be pre-programmed or programmed to automatically compensate for external brightness and act as instant "transition" lenses and can be either used on the AR glasses display or with computer intelligence can be used on typical corrective lenses. In this case, the entire exterior layer of Transparent OLED or LCD would tint much like a light valve to balance the bright external light, and still provide additional opaqueness on the portion of the lens where the virtual video or picture or image is being displayed.

In another aspect of the invention, the display can be a small display like OLED-on-Silicon micro-displays. Such a display device consists of two key elements: the silicon backplane that contains circuitry to drive the OLED pixels, and the OLED emissive frontplane layer. With a small micro-display which is only 1 inch by 1 inch but contains 2.5K by 2.5K resolution, with as bright a display as possible (1,000 NITS) one can use two displays, one for each eye, to be the projector on to a reflective or semi-reflective lens. In this case, the micro-displays can serve as the projector for a reflected display which the eyes of the wearer would see. The correction or fine tuning is offered by keystone corrections contained within or on the GFH and the correction for projection of the reflected display.

In another aspect of the invention, one or more small micro displays like the those offered by TSMC, which is a 1 inch by 1 inch, 2.5K by 2.5K resolution display(s) can be used to project an image onto a clear lens connected to the a head mounted display that contains computer intelligence through a CPU and can be known as a Smart Head Mounted Display (SmartHMD) or GFH. In another aspect of the invention, there would also be either or both a layer of reflective film on the lens or the outer layer of the lens contains the Dynamic Opacity technology as explained above. In this instance, a corrective lens or lenses can be affixed to very small micro-displays, which are bright enough to provide a reflected image onto the reflective lens. In this instance, the micro-displays in order to correct and fine tune the image for displaying on an ultra-short throw between the display and the inside of the reflective lens can utilize one or more image correcting lenses and can even be combined with a middle layer of a wave guide or polarization, which provides enhanced image resolution and guides the image's rays to exactly where it is to be displayed on the reflective lens.

Figure 32:
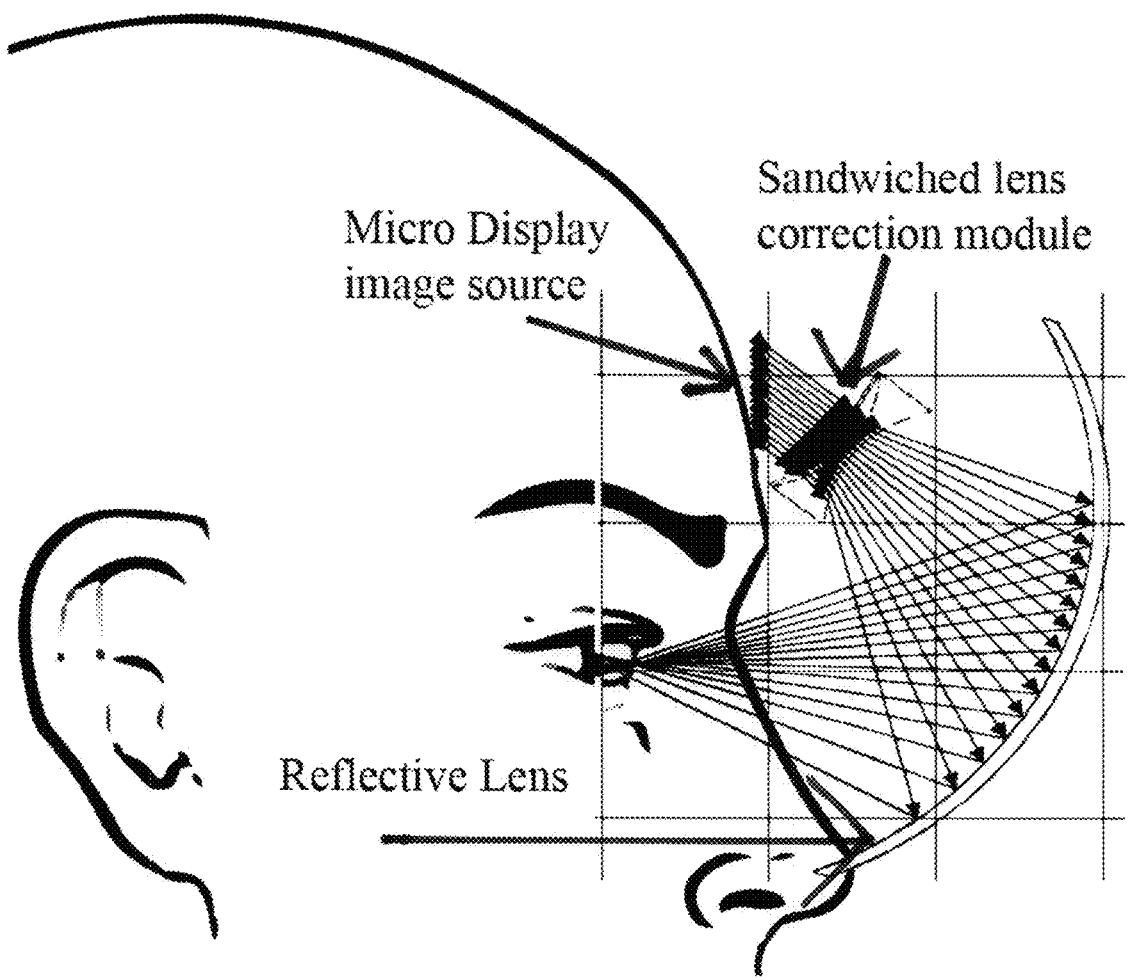
FIG. 32 is an illustration of a micro display configuration.

In one embodiment of the invention, two corrective lenses sandwich a wave guide or polarization layer. The image projection source is a small display, as shown in FIG. 32, that is rotated to achieve the greatest clarity and field of view. The image source (OLED) is then passed through a circular polarizer. The circular polarized image is then passed through a lens with a positive diopter to focus the light through a linear polarizer. This linearly polarized light is then passed through a negative diopter lens, and possibly multiple negative diopter lenses to achieve the necessary projection size required. The purpose of the polarizing films used either in combination with other correcting lenses or not, is to retard the light that may be reflected back onto the micro-display and to focus the light rays on the specific part of the reflective lens as is desired. After a passing through the lens curvatures which will provide the correct size of projection, the image is then reflected into the eye using a spherical lens, possibly coated with a semi-reflective or reflective surface. In this aspect of the invention, the angle of the display and lens combination to the angle of the spherical reflection surface will be adjustable to provide focus for eye location, which can be monitored using eye-tracking technologies combined with the control of the projected image. Further, an adjustment can be permitted on the corrective lens which is correlated to the micro-display, and thereby one can change the closeness of the lens to the micro-display, which would permit the user to adjust the reflected lens display closer or further from the user's face, to better allow room for the user's own corrective glasses or large facial features, like a large nose or other gear worn on the face like an oxygen mask or filter mask (i.e. like for a fighter pilot or in a HAZMAT situation).

The Eye-Tracking subsystem works through hardware and software. The software is connected to the system's GPU working in connection with the systems model controller. The eye-tracking is captured by infrared (IR) light being projected onto the eye, which creates a glint or reflection, which is then captured by an IR sensitive camera. Typically, an eye-tracking system captures the glint from the eye from 30 frames per second to 500 frames per second. This information is stored in real-time in the Model Controller, which can be a MVC, and them processes this information into a virtual space represented by XY or Cartesian coordinates. These coordinates provide the system with the information about where the user's gaze is in relation to the reflective lens. When used for medical applications like AMD, the eye-tracking information is correlated with the buffered information about the person's eye visual defect such that when the manipulated image is displayed, it is in sync with the user's gaze. This is necessary because the eye scanning and eye movement necessitates that the buffered and manipulated area of the video be moved to correspond to the user's eye gaze so that the buffered "hole" and the user's defect align and remain in sync. All this processing happens in real-time and keeps up with the movement of the user's eye. Latency is important and keeping the latency to less than 10 milliseconds will aid in preventing the user from feeling dizzy and preventing whirr.

In another embodiment of the invention, a computerized worm gear or drive is used, or non-computerized mechanical device such as a worm gear or gear can be used to move the micro-displays on the GFH such that the displays can be aligned with a person's own Inter Pupillary Distance or IPD. In the case of a computerized worm gear, this gear can get its information about how far to move in one to four directions from the eye-tracking subsystem, which can measure the distance from the gleam detected in each of the person's eyes and transmit measurement data into movement data so that the worm drive aligns the micro-display in the GFH to the perfect position for the persons own IPD and relative height vis-à-vis the way the GFH is worn, so that alignment side to side and up and down is accomplished. Alignment of the user's eyes on a four axis is necessary because this ensures the sharpest reflected image for each individual user in combination with how the user wears the GFH.

In another aspect of the invention, the GFH can be made where it is locked on a user so that in institutional environments it cannot be easily removed. In this aspect, people, such as inmates of some type would be required to wear such GFH headgear, so that if there is trouble or emergencies, a manager could either cut off the video feed leaving the user with only limited sight resources with which to navigate. This may reduce the desire to become aggressive or provide information for emergency exit. In this embodiment, the display screen is subject to the command of an outside operator, and could display, for instance, peaceful pictures, and soothing music to calm the user experiencing a fit. Or the display could become opaque and deny the user the ability to see. Or the display could be used to heighten awareness with magnification, color enhancements and sharper contrasts of images and sound. The GFH could also be used to dispense smells to either enhance a pleasurable experience, permit a focus on identification of a person, or thing, or for training purposes, like to give a user an artificial experience like would exist in a simulation or another not currently existent real-world situation.

In another aspect of the invention, the GFH is more like a helmet or the display more like a face shield than lenses.

In another aspect of the invention, the GFH is more like a band and the reflective display is like two partial spherical clear lenses, one partial sphere over each eye.

In another aspect of the invention the real world is not displayed, but videos, television shows, emails, or other online or prepackaged information is displayed, either with or without the macular degeneration type pixel manipulation, so that a user could experience other forms of entertainment, training, learning, or task accomplishment with the Mixed Reality Glasses than just a real-world projection onto the display. The GFH can also be fitted with night-vision, infrared, or other types of cameras so that the experience is hyper real world. Thus, any kind of camera can be used to make a display. In this embodiment of the invention, the GFH can be programmed to act as a host for other devices utilizing technologies like Apple Airplay, which permits the GFH to be "paired" with other devices, like a phone or smart watch. In this instance, one would refer to the GFH as a smart head mounted display or SmartHMD and all the applications (apps) on a person's cell phone or tablet can be transferred to the GFH seamlessly. So, in this instance, a user could begin a Hulu or Netflix movie on a cell phone or tablet, and then it could be directed or transferred to the GFH for continued viewing, which would free up the cell phone for other use. In this aspect of the invention the GFH is connected to the internet via cellular or WIFI or other radio frequencies or wireline or wireless frequencies and acts like a router with other devices which can attach themselves to the GFH, much like computers acquire and connect to a typical internet router. This provides the GFH with the ability to access the internet.

In another aspect of the invention, the GFH is loaded with Artificial Intelligence, like the Google virtual assistant, Siri, or Alexis. In this instance, the GFH can be programmed with a virtual assistant virtual image and be able to show a visual virtual assistant (VVA), not just a voice like Siri or Alexis. Technology like invented by a group from the University of Washington, where researchers have created a new tool that takes audio files, converts them into realistic mouth movements, and then grafts those movements onto existing video. In this instance the AI software neural nets are trained to change a video of a speaking mouth to other words can be used to create a VVA with a minimum of actual videos taken of the live subject which is to be the VVA.

Under this embodiment, the GFH can include either speakers which would be controllable or have incorporated into its sound system earbud type speakers, which are either attached via wire or via a wireless network in the GFH like Bluetooth light.

In another aspect of the invention the cameras can be used to not only display an image in real time to the user, but to record the image that a camera captures for replay later. Thus, a user, if sleepy, could activate a "record" button, causing the CPU and GPU to record the real-world images, for instance from a football game, and the user, when awakened, could then enable the recorded display to show on the lenses of the GFH. This feature could also be used to recall real world experiences, for instance to record a university lecture for playback and contemplation at another time. The playback can be in real time, slow motion, freeze framed, stopped, and fast forwarded or reversed. In this aspect of the invention the GFH has a Subsystem which permits storing data and replaying data and menus to identify the stored information, or to recall an instruction previously given. In this instance the user could activate the record when taking medication and the CPU would log such information and be able to respond to visual, text input or auditory requests, like, "did I take my medicine today" to which the GFH would respond yes or no or not known, depending on whether the recorded information was available. In another aspect of the invention the record function can be configured to automatically record certain functions, like image recognition software which could activate the recording of taking medicine, convert that to data base information, and be able to play back the correct information to the user. The GFH could also become Bluetooth enabled when in the proximity of other devices, like a pulse oximeter or blood pressure cuff, and automatically record this information and store it in the data base to be replayed, recorded for later use, or sent to a third party, which might be a caretaker or health care provider or store for recall by the user.

In another aspect of the invention other meaningful information can be displayed along with either the real-world information or non-real-world information (such as TV or a movie) where a user can be altered or amended by text information or sound to conduct a certain time-based task, like, for instance, an alert to take medicine, check on a pet, or answer a phone call or email. In this instance the GFH would permit the user to use the D-Pad, Fiducial Marker, or other controller to switch from a real world or non-real-world experience on the display to a task-based experience, such as an email or phone call or video phone call. These examples are but a few of the many tasks that would need the user to switch the input of the display, and all examples used herein are by way of illustration and not limitation, in this specific case, the main idea being that the GFH would be akin to a wearable computer, and permit a change in the user's environment and display to correspond with the task or undertaking necessary at the time, whether to see the real world, to see the non-real world, or use the GFH as a wearable computer, online device, Wi-Fi device, RFID device, Near Field Communication device, or other communication device, learning device, or a smart device, like one that would clock elapsed time.

In another aspect of the invention, the GFH acting as a wearable computing device could process a credit card payment or undertake some other task that the physical limitations of the user would otherwise prohibit or would enhance.

In another aspect of the invention, the GFH does not provide specific correction for eye diseases like macular degeneration which requires repositioning pixels or vectored images but does contain all these Subsystems which exist to inform the user and show a user how to reach a certain waypoint, or prioritize travel, all displayed on the lens display of the GFH. And in another aspect of the invention, the pixel manipulation is used, but not to correct for eye defects like macular degeneration, but to reposition a display onto a certain portion of the lenses, so that a user can see both the display and the real time world at the same time.

Thus, the GFH can contain other wearables technology to monitor, report, and track or direct the user. This can be done by audio, or within the display or as a separate display, where, for instance, the real-world environment is displayed, and a text is also shown of directions, or alerts or any kind of useful information to the user. Alerts could also be signaled by vibrations from the GFH. The GFH can also signal messages to people external to the GFH, and, for instance, to alert third parties that an impaired sighted person is passing. Or alert third parties that the person has some sort of authority, like a siren, or flashing light, in the case of police officers or emergency personnel.

The GFH also contains the Image Projection and Lenses (IPL) System which is the combination of the projector and lenses upon which the image or corrected image is to be displayed, along with their connectors and integration with the other Systems and Subsystems.

The GFH also contains connectors for a patient diagnostics programming, and computer interface, for wearable computing functions and other Subsystems, explained herein. The examples above are designated herein as "subsystems" or "Subsystems" of the invention which also is understood to include all powering, connectivity, computing, display, and integration of the Subsystems. The computing and patient diagnostic programming can be resident in the system or external through a connector. Thus, for instance, the patient diagnostics programming can be in the circuitry and intelligence of the system, the GFH or accessed externally through wire or wireless connections to a device like a tablet, laptop, computer, or mainframe. The GFH may all be worn on the head, or be like a helmet, or be dispersed on other parts of the body as auxiliary wearables.

The second major System is the Camera Input System (CIS), which typically includes one or more cameras and their lenses, connectors, and operating systems. As mentioned above the cameras can be of a typical video or still camera or can be of a specialized nature like night vision, infrared, 360 cameras, thermal imaging, magnification, color, black and white, or 3D cameras with each their own distinctive displays. One or more of each of these different type cameras can be incorporated into the CIS System.

In a typical medical correction configuration the GFH would contain one or more camera and camera systems for capturing the real word visuals that the user would ordinarily see; and also can contain one or more cameras which monitor eye movement so that corrective software can receive this eye positioning information and approximate the epipolar geometry of the eyes (eyes moving inwards or outwards, left or right, transversely) and calculate for the same as well as the offset of the line of sight of the cameras versus the actual eye position so that the display shows nearly what the user's eye would ordinarily see.

In another embodiment of the invention, the CIS may be partially or completely embedded on smart contact lenses, where the cameras, in the instance of macular degeneration, are positioned on the smart contact lens (SCL) in the exact location where no sight exists, being typically in the most central 15% of the eye. In the instance of the SCL it may contain is own battery, sensors, communication, and charging apparatus including communicating via methods such as backscatter, Interscatter, Bluetooth, Wi-Fi, ZigBee, RFID, and other antenna transmissions. In these instances, the GFH provides the energy to be harvested by the SCL and the communication network and protocols, for wireless communication, all of which are a Subsystem of the GFH. Thus, if SCL were worn by themselves they would need another device to harvest energy and communication reference from, here the GFH System provides the necessary energy and communication link and are synced together.

In another embodiment of the invention, one or more cameras per eye are used to create monocular or binocular vision. In this instance the GFH System would also have a method to monitor the movement of at least one eye, like a camera in the GFH facing back towards one or more eye to monitor the eye movement, for line of sight augmentations to the projected image, and for epipolar geometry corrections for the movement of the eyes focusing on far away versus close items. One Subsystem and method for monitoring the eye in another camera, one or more which is directed at least one eye. This camera would utilize eye tracking software to provide to the IMP the information necessary for an adjustment in the display so that the image displayed as nearly as possible represented the real-world images, thus, there would be correction for epipolar geometry and line of sight at least in the software.

In another embodiment of the invention one cameras is used, creating monocular vision to be displayed to one or both eyes. In this instance, the monocular vision can be corrected per eye, so that the "cut outs" are different for each eye, such that the correction best suits each eye differently.

In another embodiment there are one or two or more cameras per eye, receiving real world input. In the instance of using two cameras per eye, it is recommended that they would be offset towards each other, so that each camera's FOV intersects the other. This is because when capturing a wide Field of Vision, the cameras themselves interject a certain amount of distortion. A typical camera lens, which does not introduce a great degree of distortion is only up to about 75 degrees FOV. Thus, to capture more than 75 degrees FOV, which is often necessary under this patent's teaching, two cameras are recommended to avoid wide-angle lenses, which introduce distortion, and avoid the most distortion from camera lenses that attempt wide FOV. However, by using the joint image from two cameras, and then "stitching" the image together as one in software, less distortion is introduced into the actual image to be manipulated and a higher degree of pixel accuracy is maintained from the camera input to the Image Manipulation Program(s) (IMP).

The third major System is the Microcontroller Control Circuits. This group of chips, parts, circuits and circuit boards include one or more microprocessors, its circuit board and parts, and typically a specialized Application Specific Integrated Circuit (ASIC) which may be a separate chip or housed in one of the other chips in the microprocessor circuit board. The MCC does the main functions of the invention and receives the input from the CIS and sensors, runs the routines and programs for collecting sensor data and visual images, and then corrects for the macular defect of the user and controls the display. Portions of the MCC System are controllable by the user, especially related to the Macular Degeneration Diagnostic Program (MDDP) Subsystem. This MDDP Subsystem contains the software and firmware for the patient application defect mapping program which establishes the boundaries, one or more, per eye, of the defect area, as well as the boundaries of the area of projection. The MCC also houses the Video Manipulation Programs (VMP) which collects the camera input and repositions the image and pixels, for corrected vision display. The MCC also houses the Application Program Interfaces as well as the Graphic User Interfaces (GUI) and routines. The MCC also houses the controllers for all of the sensors, inputs and outputs and user control.

As stated above the VMP may be any number of kinds as described previously, or could be a Pixel Manipulation Scheme or Vector math like taking the image from the real world such as the Pixel Interpolation and Simulation, Image Stretching, or other software video distorting application.

In one embodiment, the flat picture as sent to the buffer by the camera and is turned in to a "fisheye" or "barrel" distortion where the middle is larger and then the image is squeezed at the edge. In this instance, the central image, which is as near as possible to the deficit of the person's disease, is removed and the image is stretched and displayed. In the instance of the goggles, the edge is not critical, and may simply be "cropped" to permit the central portion of the video to be displayed without the edges, which have been pushed out by cutting the central portion out. In another embodiment of the invention the edges are important, like in the case of the Mixed Reality macular degeneration glasses where Phase Two distorted images must be remerged into Phase Three video images.

Thus, this invention teaches that one camera can be used for monoscopic image capture and display. In addition, this invention teaches that you can use two cameras to simulate on the goggle/glasses display true stereoscopic vision, wherein the IMD model includes factor correction for epipolar curves, guided by the epipolar geometry so that stereo vision, generated by two or more cameras, can be employed and be displayed, and seen, as one PRI image.

The invention uses computer aided video images which are skewed and stretched in a matrix distortion or other similar fashion to put the most or the entirety of the image onto the peripheral vision of the patent by opening up the center of the image and manipulating it to the peripheral cones of the eyes, as seen by the patent in the projected image, in order to project the video captured images on the peripheries of the cones in the eyes where vision is still active. One of the benefits of this invention is that no invasive procedures are necessary and as the patient's macular degeneration changes the software can be adjusted so that the image is now correctly skewed.

In the fashion taught by this invention, the viewed experience may make it nearly impossible for the user to distinguish between what is actually seen and the image that is created by the PRI.

Thus, the spreading and/or multi-lateral skewing of the image reflects the corrected image onto 3D or High Definition goggles and/or glasses worn by the patient. The image is skewed via the IMD module to avoid projection to the area of the eye which involves the macula, but still has all the image information. To imagine this process, think of a picture which is printed onto a stretchable and compactable substance. A hole is cut into the middle of the image and stretched open. The image compress into the sides of the picture. Thus, all of the information of the picture is still there, it is just rearranged where a hole is in the middle and the image is moved each way to the side, top, and bottom. This "hole-cutting" is done via algorithms and computer software/firmware technology, for instance, using a technology like Matrix Distortion as above mentioned.

Matrix Distortion of a camera and Matrix Calibration, which is the correction of the distortion are commonly known areas of camera calibration and have been used for a long time. Often times cameras display significant distortion. However, the distortion is constant like on a matrix, and with a calibration and some remapping the distortion can be corrected. Typical distortion correction takes into account the radial and tangential factors. For the radial factor one uses the following formula:

$$x_{corrected} = x(1 + k_1 r^2 + k_2 r^4 + k_3 r^6)$$

$$y_{corrected} = y(1 + k_1 r^2 + k_2 r^4 + k_3 r^6)$$

So for an old pixel point at (x,y) coordinates in the input image, its position on the corrected output image will be (x_{corrected} y_{corrected}). This corrects for the presence of the radial distortion which manifests in form of the "barrel" or "fish-eye" effect.

Tangential distortion occurs because the image taking lenses are not perfectly parallel to the imaging plane. It can be corrected via the formulas:

$$x_{corrected} = x + [2p_1 xy + p_2(r^2 + 2x^2)]$$

$$y_{corrected} = y + [p_1(r^2 + 2y^2) + 2p_2 xy]$$

However, for this invention a type of reverse methodology is employed, that would not normally be thought of. Thus, once typical distortions in the camera have been fixed, then, it is the teaching of this invention that an intentional distortion is introduced. In one embodiment the IMD model stretches a center pixel to the points at which an individual cannot see, and compresses everything else to fit in the remaining peripheral portion of the goggles. In this fashion a "hole" is artificially cut into the image by computer and software/firmware aided manipulation such that a pixel which was formerly in the center of an image is squeezed to the outside so that the entire image in projected around the "hole" in the center which is artificially created. Only the matrix distortion portion of the model is shown here, as the other pieces are not directly related to the IMD model. There are other substantive parts of this program for projecting the image once the IMD model is applied. As shown the IMD distortion model is shows as a value to the "webGL"1, a program which can be used with "renderingContext"2.

There are other substantive parts of this program for projecting the image once the IMD model is applied. As shown the IMD distortion model is shown as a value to the "webGL"1, a program which can be used with "renderingContext"2.

The fourth major System is the Image Projection and Lenses System. The IPL projector and lenses may employ such technologies for display such as wave guides, mirrors, prisms or other technologies, such as transparent rear projection film, to correctly display the image on the glasses (lenses) or on a portion of the lenses. Alternatively, a "heads-up" type display may be used, such as a transparent shield or facemask. In practice, the lenses may be one of any of a number of types of see-through displays, like Augmented Reality or Mixed Reality glasses, or can be immersive, and not transparent like Virtual Reality goggles. Some examples of organic light emitting diodes (OLED) which can be employed are Passive-matrix OLED, Active-matrix OLED, Transparent OLED, Top-emitting OLED, Foldable OLED, Lucius Prism OLED, White OLED, Quantum dot light emitting diode (QLED), ultra LED (ULED) and Ultra HD 3840×2160 pixel resolution, also called 4K, which is twice the resolution of Full HD and has 4 times the number of pixels. A recommended combination is transparent Active Matrix OLED (AMOLED) with the evolution of technology as it is now because AMOLED's are thin, have fast refresh rates, are less complex from an electronics standpoint, offer a lot of control over individual pixels, and consume low amounts of energy, especially sense they produce their own light; and they have high resolution and produce sharp colors, which is needed for the invention to work at its optimum. In another configuration, lenses, such as Corning's transparent display technology and features Corning® Gorilla® Glass could be used. The application of a special functional film on the thin, durable Gorilla Glass surface creates a transparent display that is acceptable for displaying real time augmented video onto the GFH lenses. In addition, the application of technologies such as LG Display's N Pixel technology can assist the invention by making the pixels clearer from any viewing by the eyes. Further, technologies such as retinal projection can be used, and would be housed in the GFH.

The fifth major System is the Diagnostics Impairment Mapping (DIM) System and tools, which include virtual simulations and tools, a user manipulated method of viewing a grid and using hand gesture sensors or tools like fiducial markers, or a connected mouse to identify the area and boundaries where no vision exists, so that this mapping can be obtained from the real "analog" world and transferred into digital coordinates for correction by the Video Manipulation Program. In this instance the user would select "Diagnostics" setting, and an Amsler grid would appear on the lenses one at a time, while one lens was being evaluated, the other lens would be opaque to not let the user be distracted by "see through." The user would trace where the edges of the border of the sight is which is then transposed by the MCC to specific mathematical coordinates which create a border where the image is to be removed and replaced elsewhere. The Diagnostic Test could be employed as often as the user desires to refine and re-correct for the advance of the disease.

In another embodiment of the invention, the display screen on the GFH is curved slightly, so as to reduce the reflections of ambient light from the display, thus improving image contrast, and focusing more of the image on the eye peripheries. The slight curvature also reduces the optical distortion (keystone) in the screen image geometry, especially farther away from the central portion of the display, were no or little image is displayed in the case of macular degeneration.

In another embodiment of the invention, normal corrective glasses/lenses are used and a film, like 3M translucent rear projection film is used and simply affixed to the corrective lenses, or the corrective glasses are affixed to the OLED material so that the patient has both his correction and the pixel manipulation in the same set of lenses.

In another embodiment of the invention, the correction for typical non-retinal problems of the eye like astigmatisms, myopia, hyperopia, or presbyopia is done in the MCC. Pixel corrections can be combined with the pixel manipulation techniques so that that the displayed video image corrects and compensates for that person's native other visual impairments, by using algorithms that adjust for the myopia or hyperopia through techniques like increased focus, increased contrast and enlargement of the video with known techniques like fixed parallax barriers, lenticular lenses, pre-filtered light display, switchable liquid crystal barrier or display, multilayer display, diopter adjustment with independent eye focus, or pre-filtered light field display and the deployment of self-illuminating pixel technologies in the display and specialized lenses on the camera to correct for the non-macular problems of the eye astigmatisms, myopia, hyperopia, or presbyopia. In this way the invention replaces corrective optics to correct vision, with computations within the software and other aids. In another embodiment, the camera lenses have the correction needed or that works with the computed correction in software.

If the camera lenses are not corrective, then the image correction is made in the software, firmware, or hardware, so that the device corrects for both the loss of sight, like in macular degeneration, and also for problems like myopia. In this fashion, a person wearing the GFH system would obtain two types of correction in the same display, (i) one for the macular degeneration, and (ii) another for the nearsightedness or farsightedness. In this situation, the invention teaches that by pre-filtering, the video on the display computes a pre-filtered light field, or uses other similar technologies, which results in a desired projection of the displayed image on the retina of a user or patient which corrects for their exact eye problem. By eradicating the rays which do not directly hit the retina at the precise angle necessary for the best correction, a user's eye prescription can be obtained without the need for corrective glasses. In other words, the correction which is computed into the video, can be adjusted on the fly, or in real time by the user via a fiducial marker, D Pad, or Control Pad ("focus controller"). An adjustment on the control pad would automatically correspond with a change in the filtering so that a more precise image is displayed on the lens and on the retina of the patient's eye. This correction can be done for each eye, so that the display on one eye is different than the display on the other eye and each eye display can be adjusted independently by the focus controller. Also, the problem of scanning or eye-tracking is solved by having the cameras needed for the correction on the smart contact lenses, which then permits the cameras input and displayed images to match that of the movement of the eyes.

In another embodiment, the augmented video may be displayed on the lenses and include the central 10 to 60 degrees FOV, for example, or any other desired FOV. This displayed video would encompass Phases One and Two. Then the stitching techniques would be employed on the "edges" of Phase Two the augmented video, here, in this example, beginning at 60 degrees FOV and using, there would be projected/displayed, for example, on another 20 degrees FOV to re-interpolated and phase back into real-world, non-adjusted video. Pixel mapping techniques can help retain image edge features better and produce higher accuracy of integration of a real-world image projection. Thus, a user would have his or her central most vision augmented via the projected video, while the video further from the central vision is reintegrated into the real world non-adjusted video, and then there is no video on the outermost peripheral areas where actual vision is used.

In one aspect of the present invention, the data comprising the visual model may be filtered or transformed to eliminate noise or other undesirable effects within the data prior to the boundary (or boundaries) being established. This process may be performed automatically using a set of predefined operations, or may be performed under the control of an operator of the model controller 14. For instance, the data may be filtered using one or more morphological transformations. Possible morphological transformations or operations may include, but are not limited to: erosion, dilation, opening, morphological gradient, top hat, and/or black hat. An initial boundary may be established using pre-filtered data and a secondary boundary may be established after the data has been filtered or transformed. The initial and secondary boundary may be compared automatically or by the operator to optimize the boundary used. Alternatively, Boolean operations may be used to filter the visual model and/or combining boundaries.

In another aspect of the invention the pre-filtering can also include the pixel manipulation which by using a parallax filter or other filter permits only the pixels which are rays that are at such an angle to miss the area of defect are utilized to be projected.

In one aspect of the present invention, the threshold is adjustable, either at the model controller 14 or at the display controller 16. If performed at the model controller 14, this would provide control to the operator. In adjusting the threshold, the operator could optimize the boundary. If performed at the display controller 16, control would be provided to the patient. This would allow the patient to adjust the boundary to optimize the boundary for current conditions.

Figure 22:
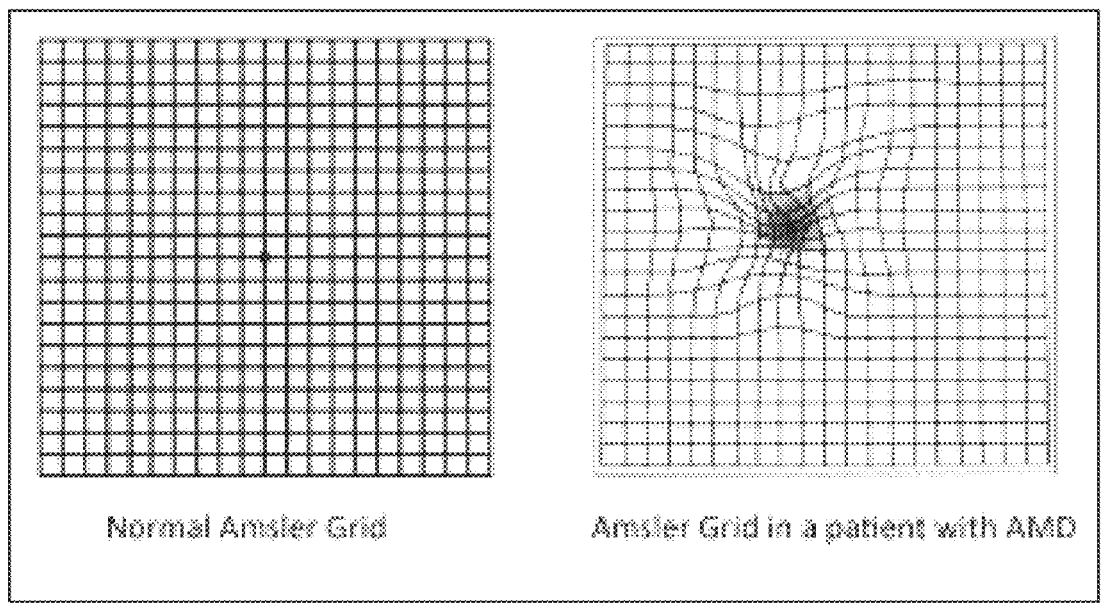
FIG. 22 is a graphical illustration of an Amsler map of a patient with normal vision and an Amsler map of a patient with AMD.

One method for making sure that the digital pixel manipulation exactly replicates that of the analog eye, a fiducial marker is connected to the diagnostic system resident in the GFH. A fiducial marker is an object placed in the field of view of an imaging system which appears in the image produced, for use as a point of reference or a measure merging the analog world with the digital world. Its applications are often seen in commercial products like virtual games. It may be either something placed into or on the imaging subject, or a mark or set of marks, as is preferable in this instance, in the reticle of an optical instrument, which is the measured camera and display. This diagnostic system is combined with the pixel manipulation system such that the input of the diagnostic system causes the pixels identified by the user as non-sighted or defective to me moved to a different location as is more fully explained below. In the diagnostic state, Amsler Grid has been included in the software to be projected onto the lenses. A sample Amsler grid of a person with normal vision and a sample Amsler grid of a person with AMD are shown in FIG. 22.

The fiducial marker, or mouse or other similar device is connected to the software so that a location on the visual grid the user sees corresponds to the virtual grid resident in the software. The user then looks through the glasses at the grid and utilizes the fiducial marker to identify the exact edges of the non-sighted space, which is then converted or identified by the fiducial marker software or firmware as the space from which pixels and images must be moved and manipulated. In another embodiment, the output of a wearable FOV test is used. For example, the embodiment may use an automated program embedded in the wearable HMD/HUD display device 50, 60. An initial start-up and mapping routine would be performed by observation, such as looking at an Amsler grid or moving objects to check the UFOV, or both, utilizing an existing FOV map to modify and optimize. Eye tracking technology may be used to ensure more accurate FOV mapping, and validating fixation. Since eye movements can be as fast as 600 deg/s. and the smallest time constant for saccades is around 50 ms; and the smallest saccades could be completed in 60 milliseconds, thus, it is possible for the "reverse cameras" which are a part of the CIS System looking at the eyes to sample eye movements at a rate of 1 kHz which will allow sufficient precision of tracking of the eyes to let the system know how to modify the output in near real time for epipolar geometry and line of sight offsets. This result is immediately usable directly as the digital input for the UFOV for the Matrix Mapping Technology.

Figure 6:
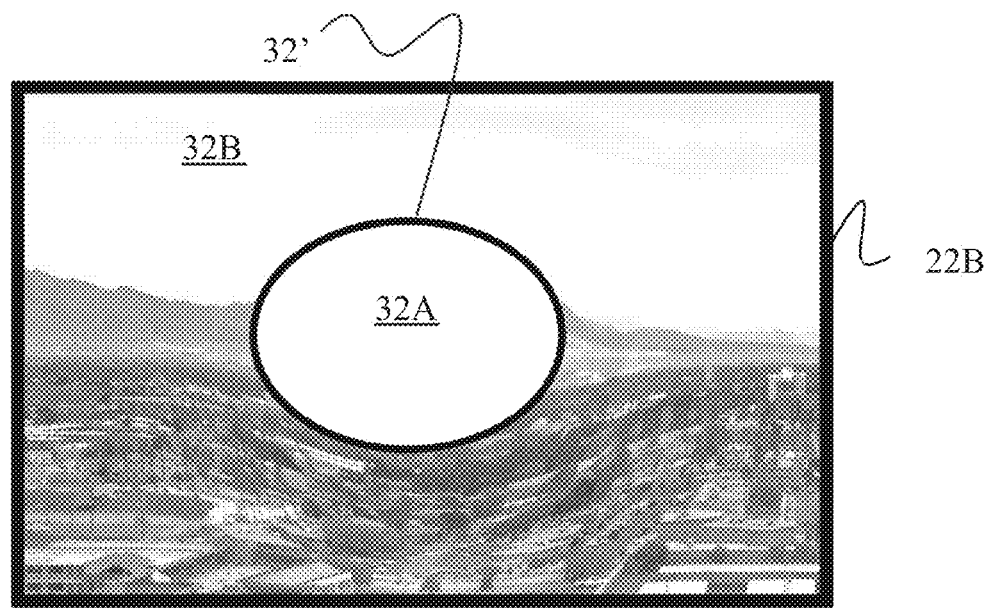
FIG. 6 is an illustration of a simple boundary comprised from one of a plurality of predefined shapes.

In another embodiment of the present invention, the boundary 32 may be adjusted or replaced with a simpler form (boundary 32', see FIG. 6). For instance, the boundary 32 may be replaced with a boundary established as a function of one or more predesigned shapes and the visual model. The model controller 14 may utilize a set of predefined set of shapes, for example, rectangles, triangles, ovals that are sized to include the affected area. The model controller 14 may select one or more shapes automatically, or the process may be performed by, or with the assistance of, the operator.

Figure 7:
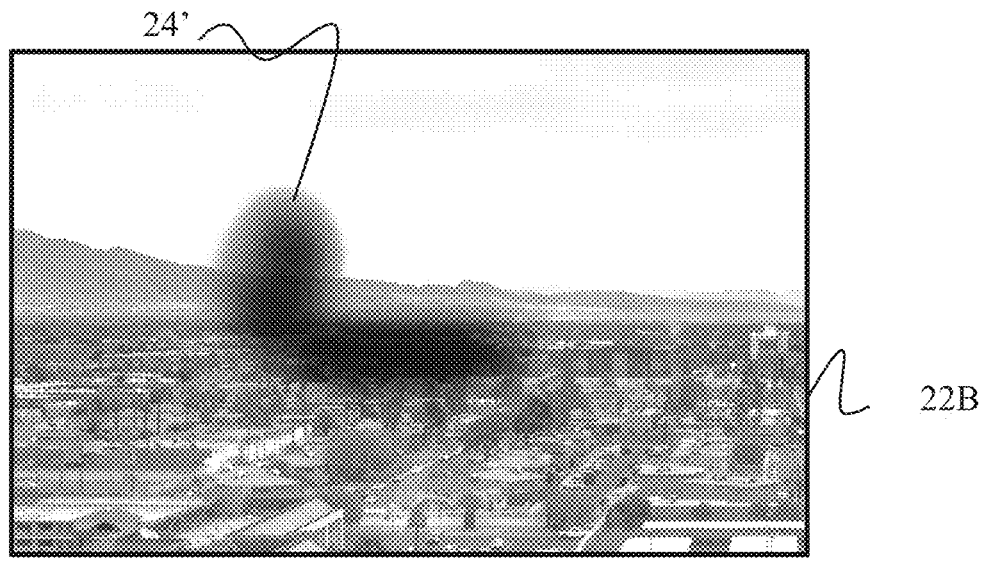
FIG. 7 is an illustration of a patient's vision with a more complex defect.
Figure 8:
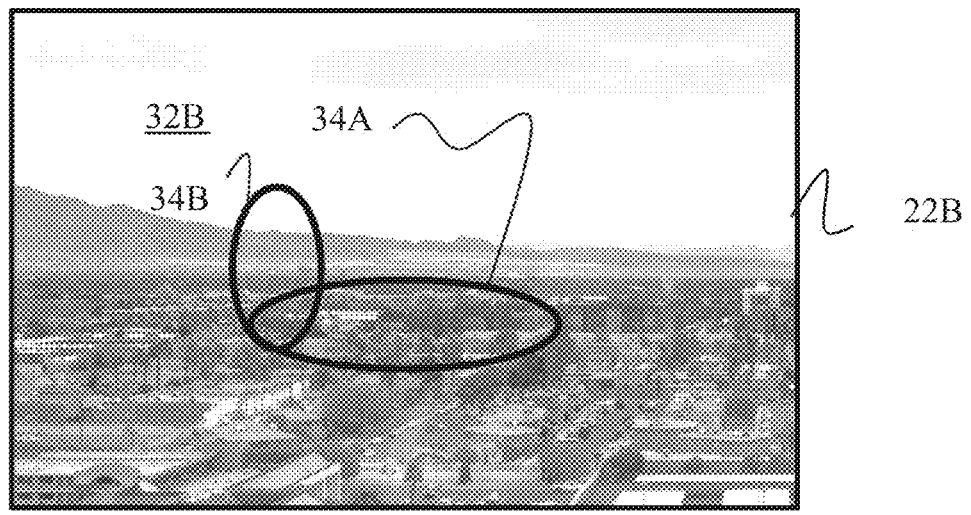
FIG. 8 is an illustration of a boundary associated with the illustration of FIG. 7.

With reference to FIG. 7, the shape of the defect or damaged area 24' may be more complex. A complex boundary may be established using the threshold process identified above, or by some other method. Alternatively, the initial boundary may be replaced automatically, or with operator input using one or more of the predefined shapes, sized to cover the defect or with the results of the user using the fiducial marker. In the example of FIG. 8, two shapes 34A, 34B are used. The boundary may be formed by the outer edge of the joined shapes.

Figure 9:
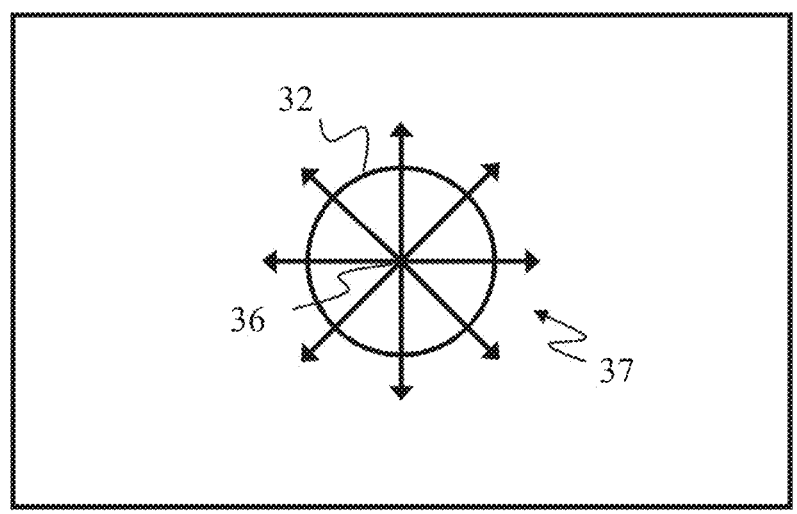
FIG. 9 is a diagrammatic illustration used in establishing a retinal map, according to an embodiment of the present invention.
Figure 10:
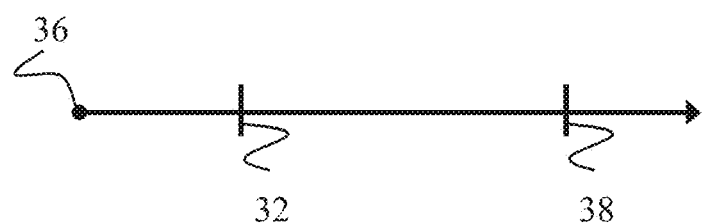
FIG. 10 is a diagrammatic illustration used in establishing a retinal map, according to an embodiment of the present invention.

With reference to FIGS. 9 and 10, in one aspect of the present invention, the image data inside the boundary 32 is shifted outside of the boundary 32. In the example shown in FIG. 9, first a center point 36 is established. The center point 36 may be an actual center of the boundary if the shape of the boundary is regular, or it may be defined by finding or estimating the center of the shape defined by the boundary or the center point is ignored and the other items as described above are used to determine how a pixel is moved. In one embodiment, image data along a plurality of rays 37 starting at the center point and extending outward is shifted outside of the boundary. It should be noted that in the above examples, the areas inside the boundary or boundaries are defective. However, in some situations, for example, where peripheral vision is affected, the area inside a boundary may be associated with good vision and the areas outside of a boundary may be associated with poor vision.

In one embodiment, the retinal map includes a series of data points which overlay the digital model. The data points are laid out in a grid in a regular pattern approximating the Amsler Grid. Each data point is defined by a set of X, Y coordinates relative to the image data. As explained in detail below, each data point is assigned a set of coordinate transformation values ($\Delta X$, $\Delta Y$), which is used to transform the image data. Each data point lies on a single ray and one or more pixels which extends outward from the center point 36. For each data point, the associated ray is found and a set of coordinate transformation values ($\Delta X$, $\Delta Y$) are established based on a set of predetermined rules. The coordinate transformation values ($\Delta X$, $\Delta Y$) are used as coefficient values in the transformation equations below.

In one embodiment, visual information in the image from the camera is radially shifted from a central point. For instance, in one embodiment the image data from the center point 36 to the edge of the image 38 is compressed (in the corrected image) from the boundary 32 to the edge of the image 38. Thus, the coordinate transformation values ($\Delta X$, $\Delta Y$) for any data point lying on the ray may be calculated based on the length of the distance from the center point 36 to the boundary 32, and the length from the center point 36 to the respective edge of the image 38. This works better in an immersive environment where the concern for the moved "edges" is non-existent.

Figure 11:
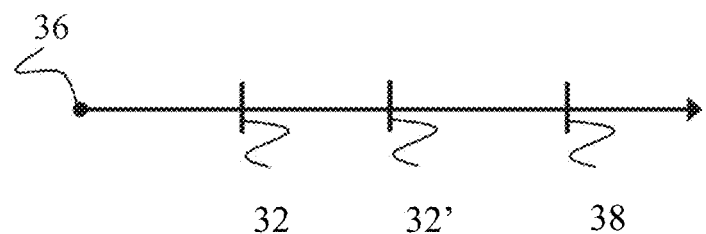
FIG. 11 is a diagrammatic illustration used in establishing a retinal map, according to another embodiment of the present invention.

In an alternative embodiment, the coordinate transformation value ($\Delta X$, $\Delta Y$) is calculated such that the visual information is disproportionally shifted from the center point. For example, with respect to FIG. 11, visual information from the center point 36 to the boundary 32 may be shifted to a segment of the ray defined by the boundary 32 and a point 32'. The length between the boundary 32 and point 32' may be equal to or different than the length between the center point and the boundary 32. In this embodiment, the visual information between the boundary and the edge of the image 38 may be compressed between point 32' and the edge of the image 38. Not only can the visual information be shifted out towards the periphery, but can also be accomplished in reverse and the visual information can be shifted inward as well.

Once coordinate transformation values are established, the retinal map is stored in the database 12 and transferred to the display controller 16. In use, the retinal map is then used to transform the image(s) received from the camera and generate the corrected image(s). The corrected image(s) may then be displayed in real-time via the display unit 18.

In one aspect of the present invention, the visual information is transformed (or moved) at each data point. The visual information between the data points may be transformed using a spline function, e.g., a B spline function, to interpolate the visual information between the data points. In another aspect of the invention, the pixels relating to the data portion of the image which is moved are reduced to smaller pixels, such that the moved pixels and the pre-existing pixels occupy the same space on the display. Or, the removed and replaced pixels may be interlaced into a video frame consisting of two sub-fields taken in sequence, each sequentially scanned at odd then even lines of the image sensor. In another aspect of the invention, the pixels may be manipulated by fixed parallax barriers, pre-filtered light display, or switchable liquid crystal barrier or display. The parallax barrier will cancel out the pixels which have an undesirable angle and permit the ray bearing pixels which do have the correct angle of projection onto the retina to pass. Likewise, the other technologies will only let certain rays through to the retina, which can be used for the cut-out and repositioning of the pixels. In another embodiment of the invention the prescription for the use is included in each camera lenses so that the correction is done at the lens stage with lenticular lenses, progressive lenses, bifocal or trifocal lenses, and the like before or at the same time as the other modifications identified in this patent.

The display controller, in generating the corrected image, shifts visual information within the corrected image in a first area inside the boundary to a second area outside of the boundary as a function of the series of data points. The coordinate transformation values are used to shift image data that exists inside the boundary to an area outside of the boundary. In the above example, the second area is defined as any area in the image that is outside of the boundary.

Figure 4C:
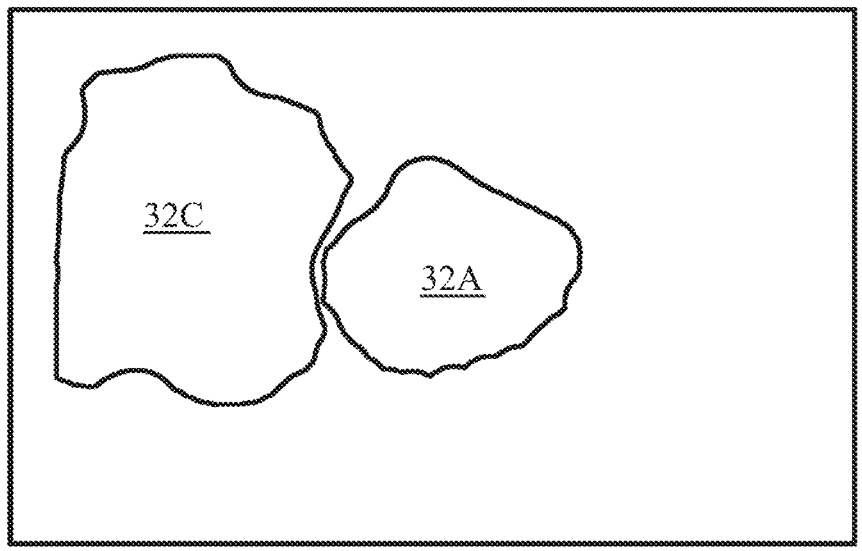
FIG. 4C is an illustration of first and second boundaries, according to an embodiment of the present invention.
Figure 4D:
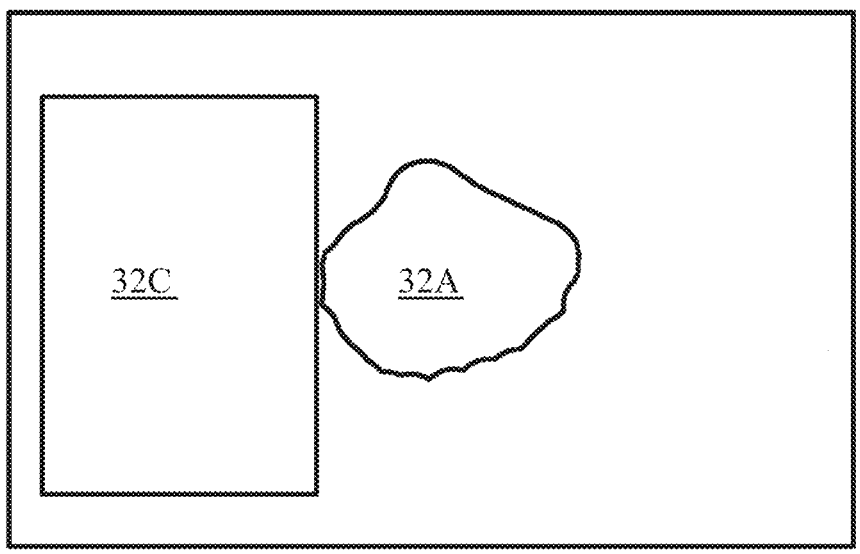
FIG. 4D is an illustration of first and second boundaries, according to another embodiment of the present invention.
Figure 5:
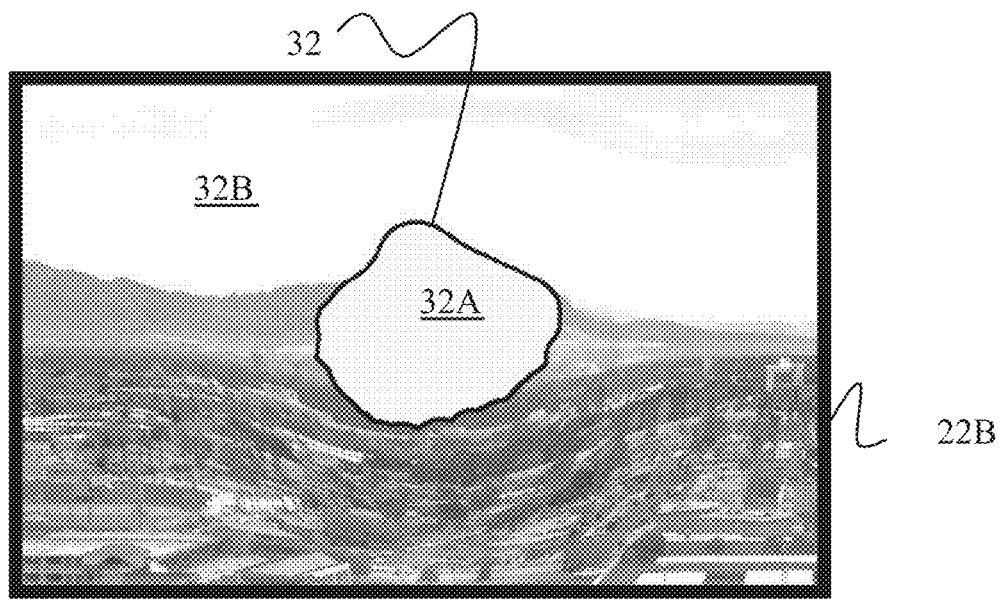
FIG. 5 is an illustration of a complex boundary, according to an embodiment of the present invention.

In another embodiment, the second area may be defined based on the data in the visual model. For example, a second boundary may be established as a function of the data in the visual model. In one example, the second boundary may be established based on the visual model that meets predefined criteria. For example, an area within the visual model may be established cells 28 in the grid 30 that have a value that meets predefined criteria. In the example above, for instance, the second boundary may encompass an area of the grid 30 in which the cells 28 have a value of 3 (or some other threshold) or less. In this embodiment, the information inside the first boundary 32 is shifted (proportionally or disproportionally) into the area defined by the second boundary. Examples of an area defined by a first area 32A and an area defined by a second area 32C are shown in FIGS. 4C and 4D. In both examples, visual information in one of the areas 32A or 32C may be shifted towards or into the other one of the areas 32A, 32C. In the illustrated examples, the second boundary in FIG. 4C has been replaced with a simpler shape/form in FIG. 4D.

In one aspect of the present invention, the display controller 16 and the display unit 18 may be implemented in a suitable user wearable device, such as smart glasses or head mounted displays (HMDs). In all cases, these hardware wearable platforms all contain wearable glasses that contain one or two forward mounted cameras, and onboard microprocessor, display technologies for viewing by the eye. Furthermore, these are usually battery powered, as well as able to plug into a PC in order to upload information via a USB cable etc. and/or for charging. This may also include HUD (Heads Up Displays), for example, the offering from Meta can be worn over a patient's existing glasses with prescription lenses 62 in order to facilitate moving between the two modes of normal vision and the augmented IDM (Image Distortion Map) vision. Alternatively, a virtual retina display maybe used to project photons directly onto the retina, or a "smart" contact lens can project the image that is worn on the eye. Any suitable method or device to present the correction image or images to or onto the eye(s) may be used. Alternatively, the image or images presented to the patient may be otherwise opaque such that the outside world is not visible.

Figure 12:
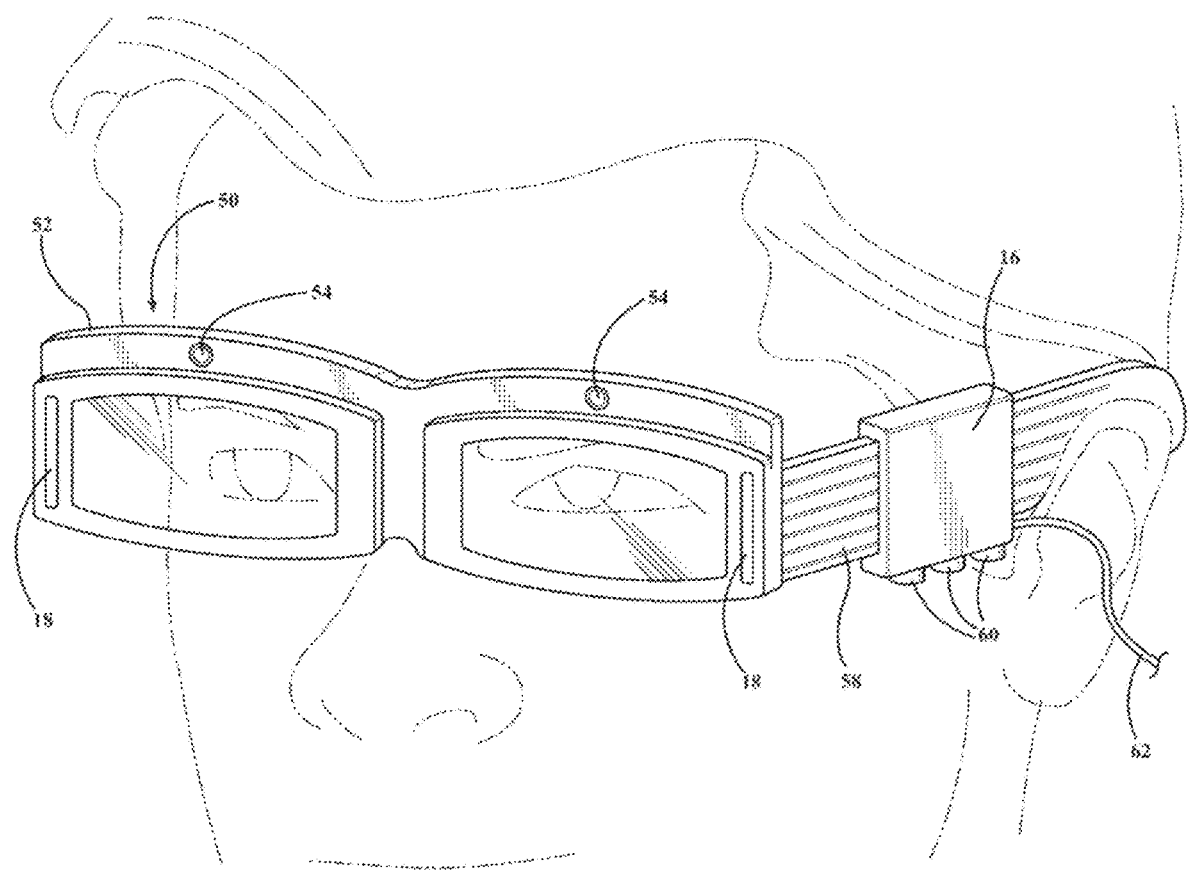
FIG. 12 is a diagrammatic illustration of a head mounted display unit, according to an embodiment of the present invention.
Figure 13:
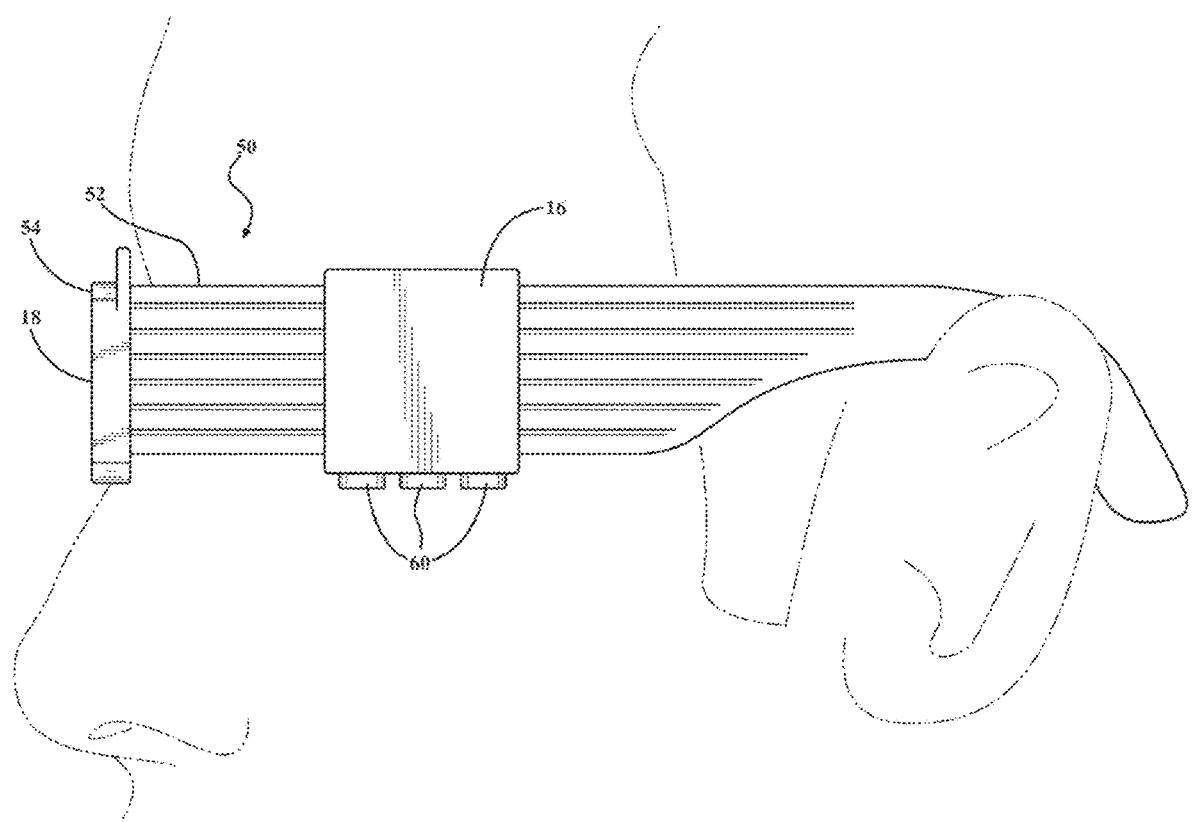
FIG. 13 is a second diagrammatic illustration of the head mounted display unit of FIG. 12.

With reference to FIGS. 12 and 13, in one embodiment, the display controller 16 and the display unit 18 are embodied in an exemplary head mountable display (HMD) device 50 that is worn by the patient. In the illustrated embodiment, the HMD device 50 includes a set of wearable glasses 52 that contains one or two forward mounted cameras 54. The display controller 16 may be mounted to an HMD frame 58 and include an onboard microprocessor. The display unit 18 includes a suitable display technology for viewing by the eye. One or more input or control buttons may be provided that work in conjunction with suitable menus, and software controls display on the display unit 18 to allow the patient/user to change options. The HMD device 50 may be battery powered and may include a USB cable or suitable port 62 to connect to, e.g., a computer to transfer data and software and/or for charging the battery.

Figure 14:
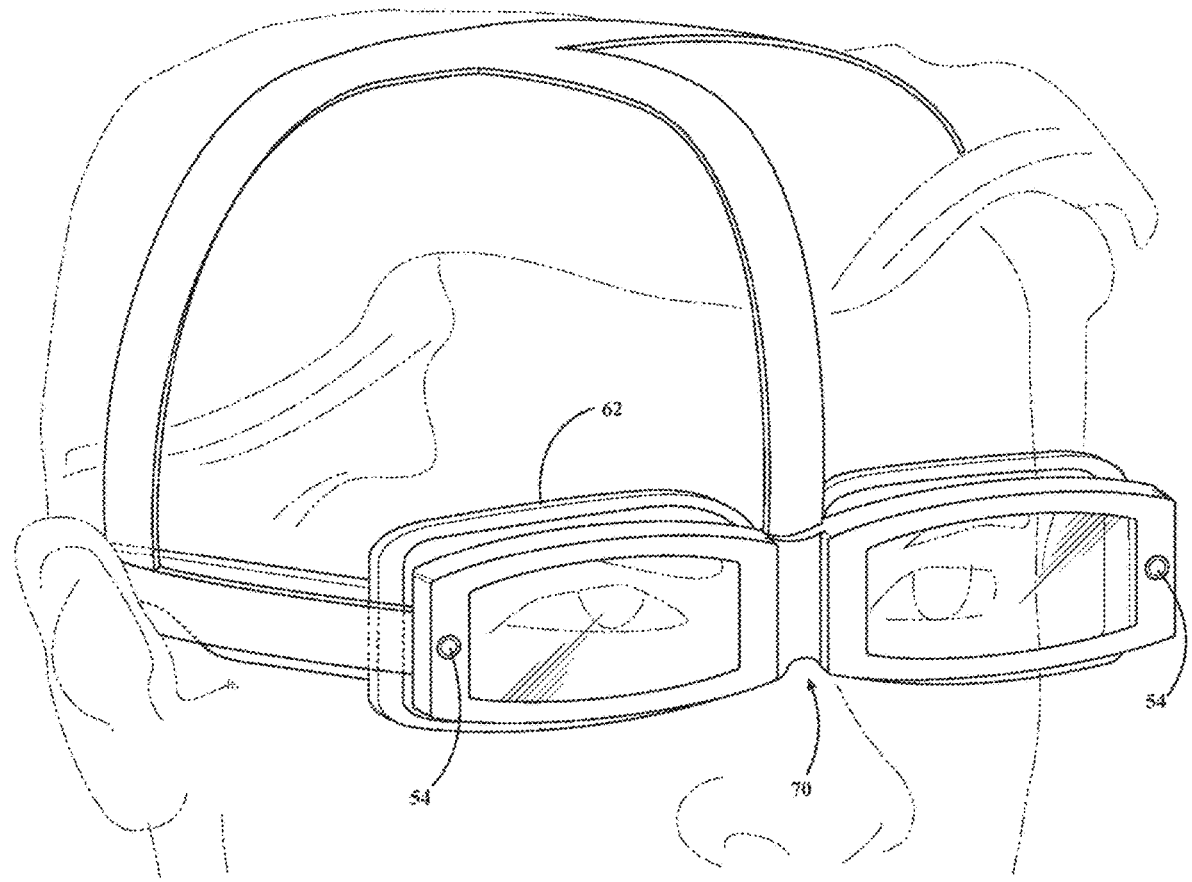
FIG. 14 is a diagrammatic illustration of a heads up display unit, according to an embodiment of the present invention.

With reference to FIG. 14, the display controller 16 and the display unit 18 may also be embodied in a Heads Up Displays (HUD) display device 60, for example, the offering from Meta Vision, that can be worn over a patient's existing glasses with prescription lenses in order to facilitate moving between the two modes of normal vision and augmented IMD vision. The HUD display device 60 are head mountable and may include different display technology such as separate LCD or LED type of display. The HUD display device 60 may embed a display on the actual lenses of the glasses themselves that overlay the image to view the augmented display in conjunction with the outside world.

Figure 15:
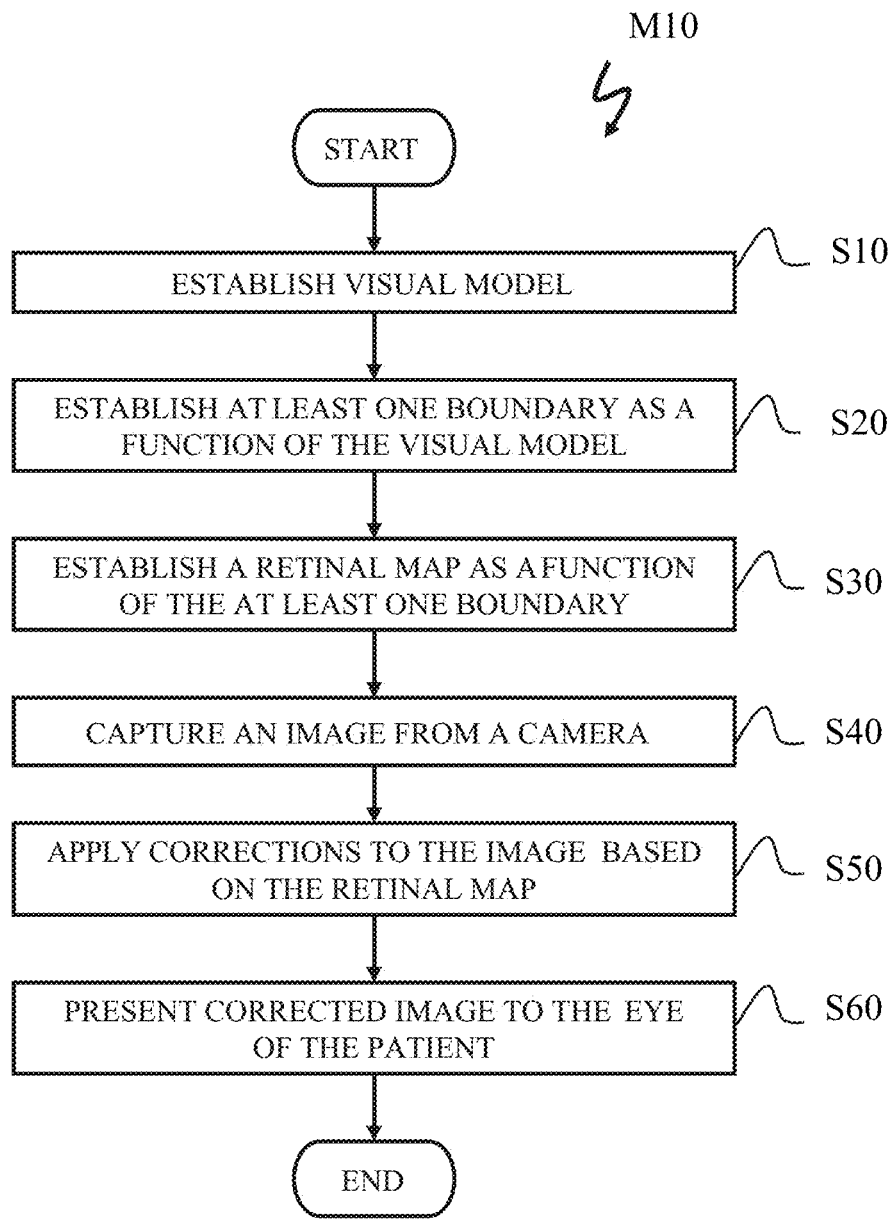
FIG. 15 is a flow diagram of a method for augmenting the vision of a patient, according to an embodiment of the present invention.
Figure 16:
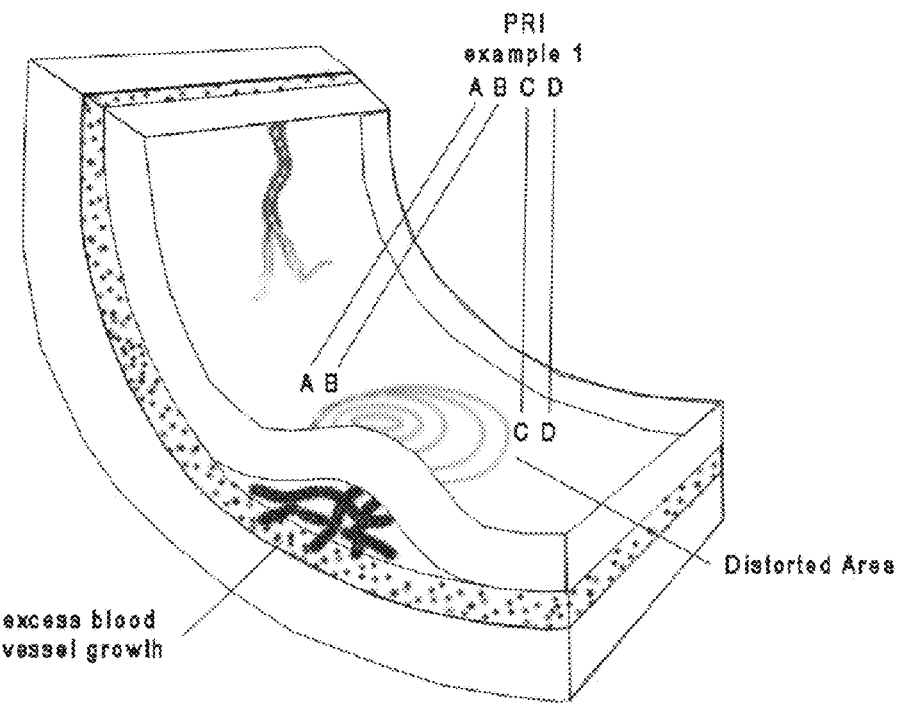
FIG. 16 is a graphical illustration of a first example of a manipulation of prescribed retinal interface, according to an embodiment of the present invention.
Figure 17:
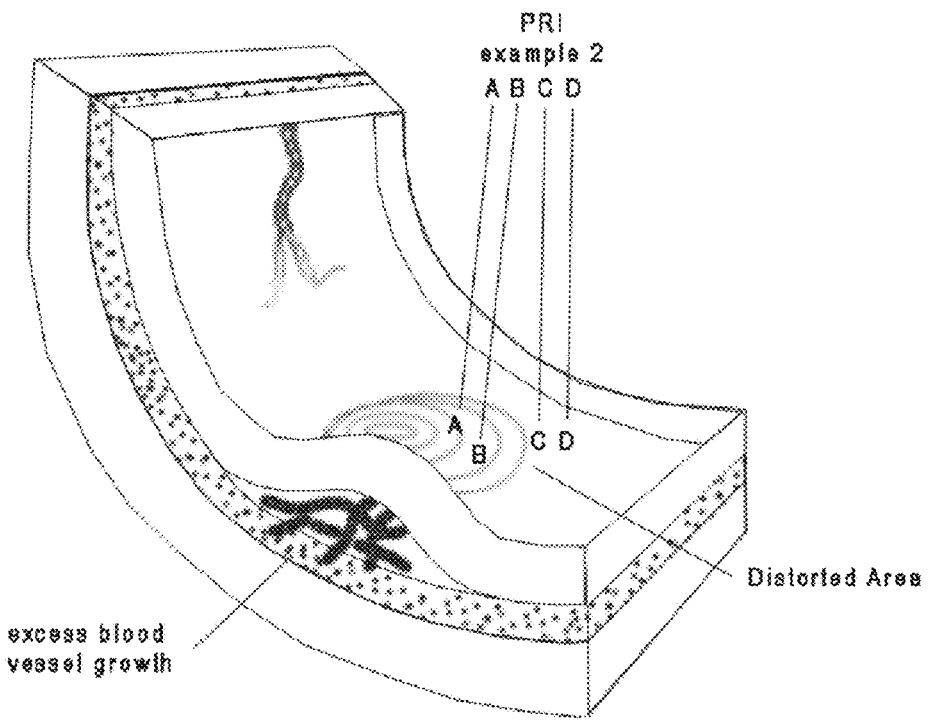
FIG. 17 is a graphical illustration of a second example of a manipulation of prescribed retinal interface, according to an embodiment of the present invention.

With reference to FIG. 15, in another aspect of the present invention, a method M10 according to one embodiment of the present invention is provided. In a first step S10, a visual model associated with a patient is established, by the model controller 14 and stored in the database 12. The visual model includes data related to a quality of the patient's vision. In a second step S20, at least one boundary is established, by the model controller 14, as a function of data associated with the visual model. At least one boundary is indicative of an area to be corrected within the patient's vision. In a third step S30, the model controller 14 establishes a retinal map as a function of the boundary and stores the retinal map in the database 12. The database may be incorporated into a semiconductor chip, which may also be existing space in a camera chip.

In a fourth step S40, an image from one or more cameras associated with the patient is received by a display controller 16. Corrections to the image based on the retinal map are applied to the image and a corrected image is generated in a fifth step S50. In a sixth step S60, the corrected image is received at the display unit 18 and presented to the eye of the patient.

The system 10 and method M10, in general, remap portions of the image(s) captured by the camera(s) which would be viewed by the effected portions of the patient's eye(s) to the periphery or unaffected portions of the patient's vision, or alternatively to another portion of the patient's retina. With this mapping correctly, executed the patient's brain adapts quickly and effective central (or periphery) vision is mimicked. This is accomplished with the forward-looking cameras as the sensor that captures the real world image. The system 10 and method M10 of the present invention shift the pixels to form a corrected image or series of images which are displayed on the micro-displays on a head mounted device, such as readily available augmented reality and virtual reality glasses. This process is all non-invasive and depends only on the processor in the glasses, the remapping software, and the patient's brain processing power through direct observation of the micro-display. The display device utilized may be implemented in head mounted devices, suitable examples of which are these offered by companies such as Sony, Epson, Facebook, Google, etc., utilize a variety of display technologies, such as LED, LCD, OLED, Photon Retinal Display, Virtual Retinal Displays, and Heads Up Displays.

Field of Vision Mapping

In order to correctly enable the pixel remapping technology of the present invention for enhancement of central vision (for the macular degeneration case) and other blindness conditions, the initial mapping of the UFOV (Usable Field of Vision) must be digitally generated. It should be noted that the present invention is not limited to mapping from a center area to a peripheral area. In some cases, peripheral vision is affected and the mapping may be from the peripheral area to the center. There are a multitude of methods to accomplish this task. In all cases the initial examination, mapping and calibration must be converted to a digital file. This digital file is then used to construct the boundaries of the UFOV. The UFOV is treated as a sharp outline where peripheral or useable vision is clear, and not degraded. However, this boundary may be a result of evaluation and determination of the gradation of the partial vision, then interpreted to construct the UFOV boundary. This UFOV border is then utilized as the baseline for the IMA (Image Mapping Algorithm) to determine the area where the effective central vision can be mapped into, along with the existing effective peripheral vision. There are numerous ways to construct the initial UFOV boundary conditions, both through direct digital means and by manual approaches that can be then converted to a digital file. In some of these cases, the FOV test may be administered by a trained medical professional such as an optometrist or ophthalmologist in the doctor's office. In other cases, an automated FOV test may be self-administered with the proper digital technology. In the third case, a trained professional can manually administer an FOV mapping test to generate the UFOV. Any, and all, of these cases can be utilized to generate the UFOV as outlined.

Figure 18:
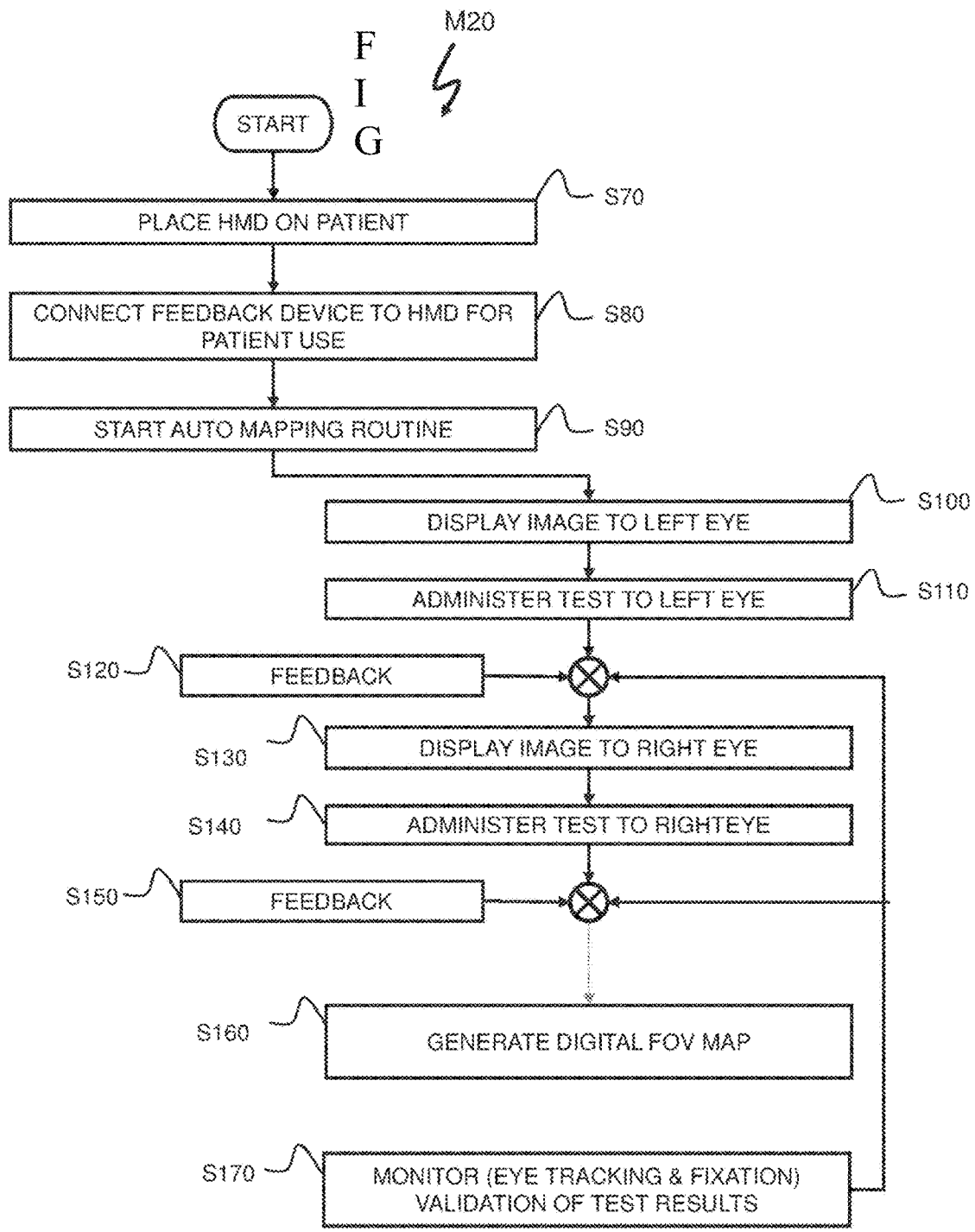
FIG. 18 is a flow diagram of a process for establishing a digital field of vision map, according to an embodiment of the present invention.

With respect to FIG. 18, the general process is embodied in a method M20. The general process is as follows:
1. The wearable GFH is placed on the patient's head and would be put into "Diagnostic" mode for FOV mapping. (Step S70)
2. The wearable GFH is connected (via external cable or wireless communication mode) to a patient feedback device, such as a PC with a mouse, tablet, and mobile phone. (Step S80) or voice recognition technology where the patient gives verbal feedback to the system, which recognized commands, clues and instructions, and accomplishes the FOV mapping automatically.
3. The auto mapping routine is initialized. (Step S90)
4. Eye tracking and fixation are monitored throughout the FOV mapping process in order to determine valid results. Given that macular degeneration attacks the central vision, it is important that the fixation and focal point test is administered through markers or objects in the peripheral vision, as well. The valid results can be driven with a secondary feedback loop by constantly monitoring fixation and using only valid visual data points for the mapping of the UFOV, and retesting as necessary to develop the entire UFOV map. (Step S170)

Figure 19:
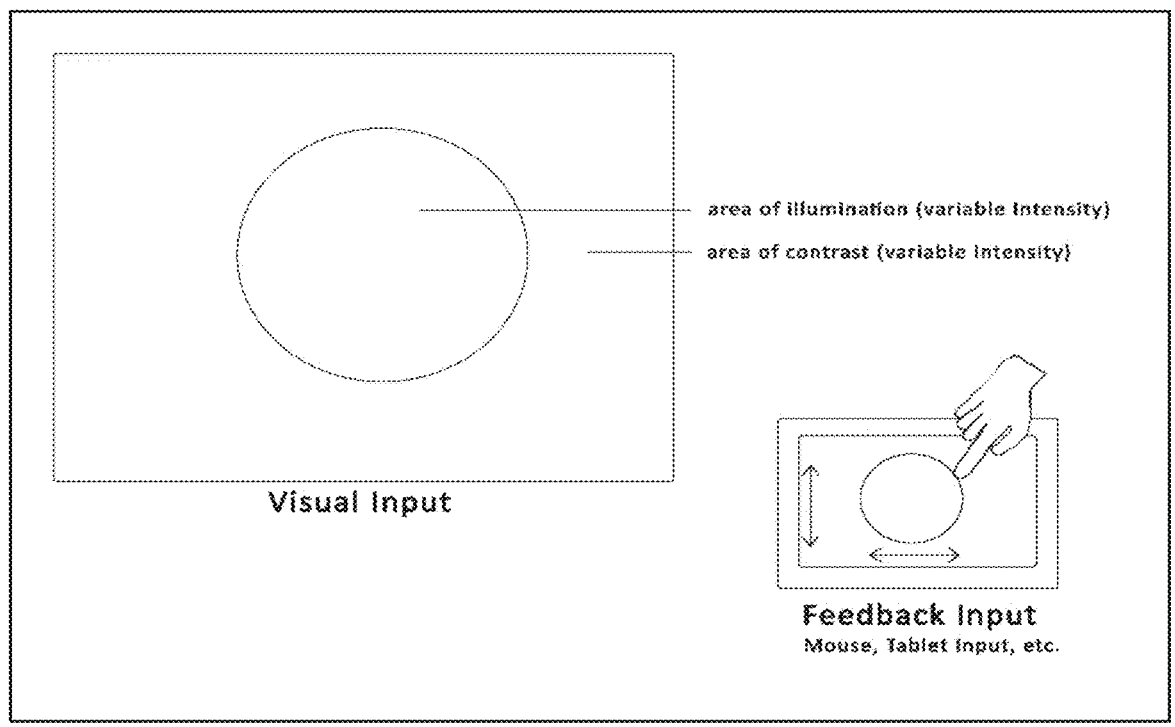
FIG. 19 is a graphical illustration of a first portion of the process of FIG. 18.
Figure 20:
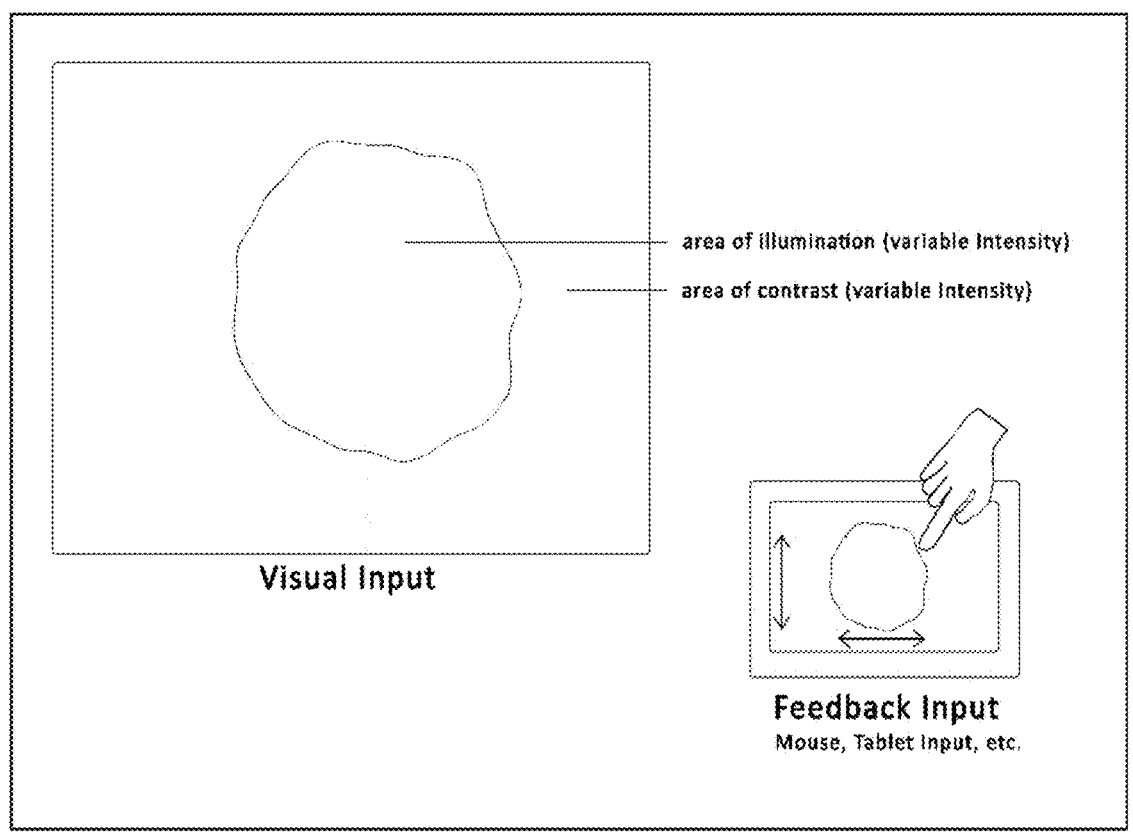
FIG. 20 is a graphical illustration of a second portion of the process of FIG. 18.
Figure 21:
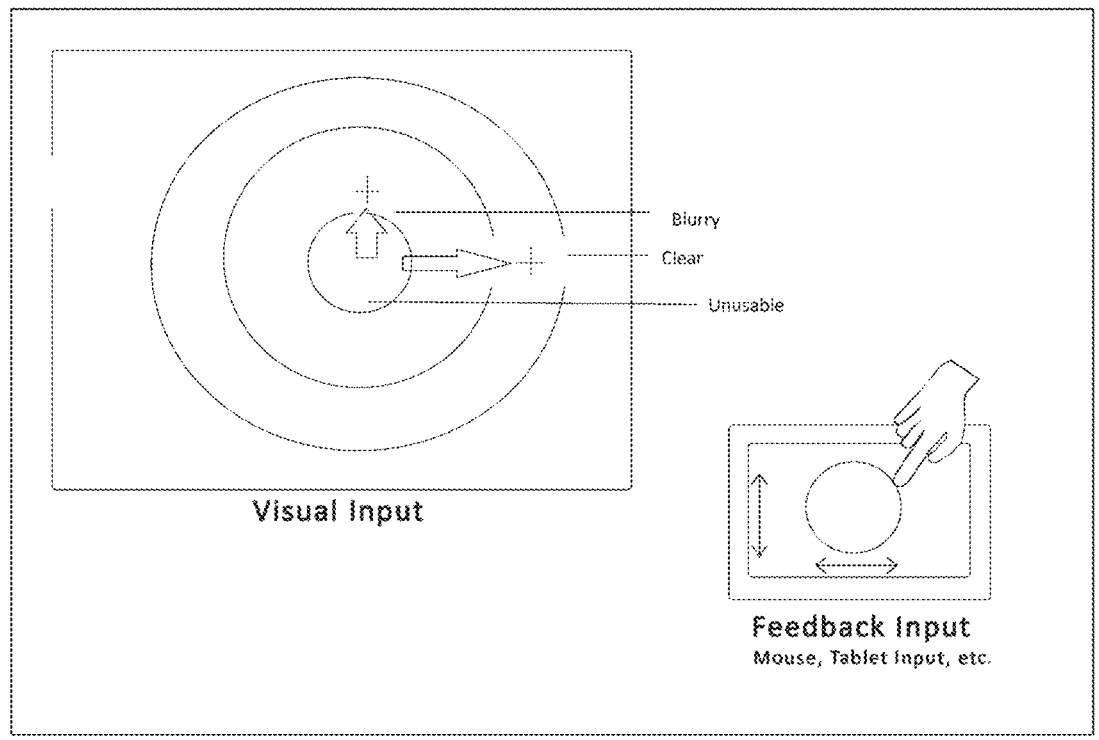
FIG. 21 is a graphical illustration of a third portion of the process of FIG. 18.

5. The FOV mapping test is administered first for the left eye (or right eye) through use of visually moving along an Amsler grid to see where images are warped or straight. (Steps S100 and S110). Alternatively, a flashing object is generated to show at different points in the patient's vision in order to determine visual acuity through the feedback device. This is performed at different level intensities to verify level of degradation of vision. See FIGS. 19 and 20. Alternatively, an object is moved through a series of sequences and with feedback, determined when the object becomes clear from blurry to unviewable, effectively creating gradations of the sight map. See FIG. 21. Alternatively, a constantly expanding sphere is displayed until the edges become clearly visible to the patient. The edges are manipulated through the feedback device until the edge of the UFOV is determined. The latter two cases offer the advantage of a faster approach to FOV mapping for utilization with the wearable later. With a quicker mapping procedure, the system is less likely to cause fixation errors due to lack of concentration from the patient. This also offers quicker calibration for more frequent tweaks to the UFOV map to optimize the performance. The further advantage that can be realized with the patient's ability to manipulate the FOV edge is to better personalize the calibration to their particular affliction (Step S120).

6. The same test is then administered for the other eye (Steps S130, S140, S150).

7. The results are validated or invalidated based on verifying eye tracking and fixation, which is done concurrently while administering the eye tests (Step 170).

8. The Digital FOV map is then generated (Step 160). The auto-mapping and Digital FOV map can be created using voice recognition technology where the patient gives verbal feedback to the system, which recognized commands, clues and instructions, and accomplishes the FOV mapping automatically.

This invention teaches the use of one or more cameras to capture the approximate line of sight of the user and display a corrected pixel manipulated version of the real world onto see through glasses or lenses though which the user looks. When the line of sight is not exact, then software is used to realign the picture or video so that it most closely approximates the actual line of sight of the eyes. Alternatively, Smart Contact Lenses are worn with the cameras place in the center of the lenses.

Further, software is used for correction for the epipolar geometry correction, so that the image is corrected for when the eye is looking at long distances versus looking at something close. In these instances, a camera looking at the eyes or one eye tracks the position of the eye and sends information to the control subsystem.

Figure 23:
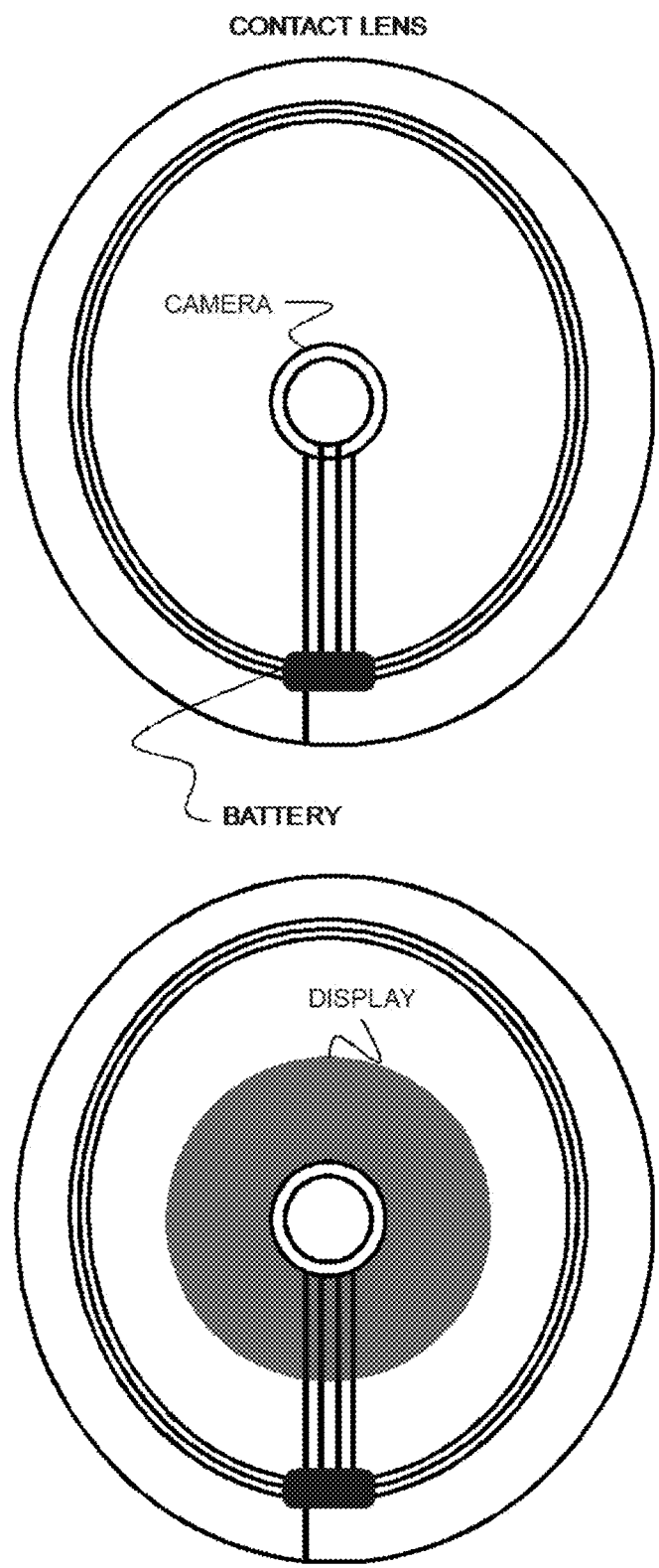
FIG. 23 is an illustration of a smart contact lens.

In one embodiment of the invention, smart contact lenses are used in connection with glasses. The smart contact lenses (FIG. 23, 26) have the camera placed in the area where the vision has been impaired or is non-existent. In this fashion, the image which is to be displayed on the lenses has the same or near similar aspect as the rest of the normal vision because the cameras move with each eyeball and, when projected with a corrected image, can approximate the real-world vision.

In another aspect of the invention, more than two cameras may be used. The two or more cameras may be used to create stereoscopic vision or to simply project the same corrected image to both eyes. The reason that more than one camera per eye may be used is because each camera institutes its own distortion, and the larger the FOV that the camera captures, the more distortion. Thus, less distortion may be introduced in the example of one corrected image displayed for both eyes, captured by two cameras to create the entire FOV of over from less than 100% FOV to over 200% FOV. This is because it is easier to use simple existing programs for "blending" or "seaming" the images from two cameras together than to use one camera that must originally capture an image which is up to 220% FOV and then correct for the lens distortion. This method may also be employed with the method described below for the employment of smart contact lenses, where the smart contact lenses may use one camera for a corrected display to both eyes, or may utilize one camera for each eye for a dual corrected display, or more than one camera for each eye/contact lens for a display to each eye or to both eyes. In addition to the positioning of the cameras, one or more, the invention teaches that software/firmware can be used to correct the projected image for eye view aspect ratio, meaning to make the projected image look as though it was captured in the line of sight of the eyes. The use of smart contact lenses with camera(s) placed in the central vision non-sighted portion of the patient's vision (the Central Vision or Macular Vision, see FIG. 23), also corrects the displayed image for triangulation and Epipolar Geometry so that a mono or stereoscopic image can be accurately displayed on the glasses/lenses or directly into the retina and be in aspect with the patient's own vision.

Irrespective of where the camera or cameras are located, either on smart contact lenses, or on the person or on the glasses or glasses frame, the image of the real world is captured, then modified in accordance with the corrective modification software/hardware which is then displayed on the glasses or a portion of the Field of Vision of the glasses. This can be done on one lens or on both lenses. In this fashion, the user is looking at the real-world vision through the glasses while simultaneously an augmented manipulated and corrected (for that patient/user) version is also displayed onto a portion of the glasses or lenses, where only the portion of the Field of View which needs to be adjusted is modified. The goal of the new inventions in this patent is to ensure that there remains some peripheral vision where real world images are reintroduced to the patients FOV, which is unmodified looking through the glasses and around the glasses/lenses so a person can use this peripheral vision to avoid hazards, ensure near navigation and be able to manage steps or other obstacles or see hazards.

The corrected display onto the glasses, lenses or retina can be accomplished with glasses or lenses using such technology as transparent OLED material, or such as Apple's Retina® HiDPI mode display, where the user interface image is doubled in width and height to compensate for the smaller pixels. In this invention where the word pixels are used it also means a subpart of an image and light emitted rays of information which is to be broadcast to the eye and retina.

Figure 24:
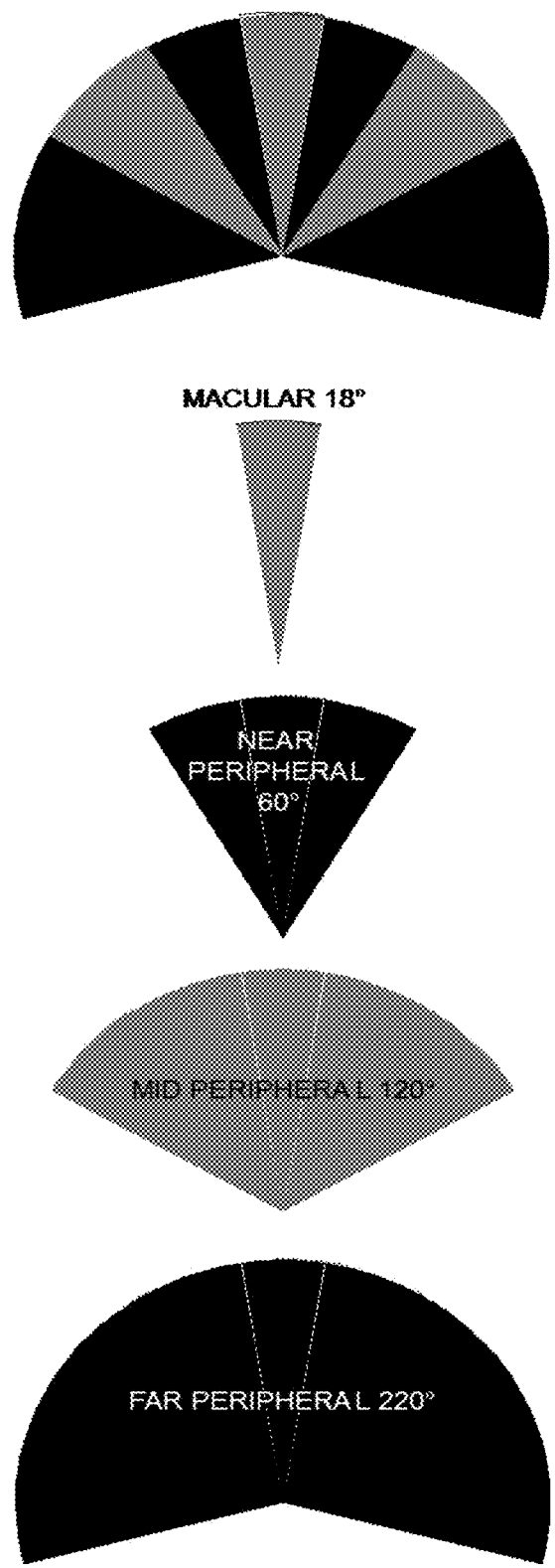
FIG. 24 is an illustration of the patient's macula.

In addition, see-through technologies which project opaque images via the use of wave guided images upon lenses, or the use of mirrors to project an image upon clear lenses, or technology such as clear rear projection film affixed to a person's prescription lenses are also suitable. In addition, technologies which project images directly into the retina can also be employed. The goal of all of this is to remove the image from the non-sighted portion of the patient's vision within the damaged macula, as shown on FIG. 24, which comprises about 18'% of the central FOV and move those images to the near peripheral which comprises about the next 60% of the FOV (minus the 18% macular vision), and then reintroduce non-manipulated images into the Mid-peripheral vision, which comprises about 120% FOV, and leave no project on the Far-peripheral, which comprises the outermost 220% FOV, all of which combine in the mind to create one homogeneous image.

In this fashion only the 30% to 60% FOV which needs to be manipulated is augmented with pixel manipulated video, superimposed over the see-through lenses, leaving the actual real-world images for the patient's Mid and Far Peripheral vision to see, so that a patient can see where to step, walk, move, and negotiate his or her real-world environment. While the estimate of 30% to 60% of the FOV being manipulated is stated here, in actuality anywhere from below 1% to over 100% of the FOV may need to be manipulated, depending on the patient's impaired or missing FOV vision, and the adjustments to the FOV which need to be made to correct for that defect. Likewise, the de-modification of the image can occur in the Near, Mid, or Far Peripheral vision of the patient, as necessary to get the best vision.

It is the teaching of this invention that merging the augmented and manipulated pixel video information is superimposed onto some type of see through lenses or directly onto the retina. This augmented video display which is attempted to be constrained into the Near-Peripheral Vision, as much as possible, contains more FOV visual information (pixelated or otherwise) than originally exists in the real world. This is augmented video display is then merged with non-manipulated real-world information, which is already available through the see-through lenses.

In the instance of merging, the augmented video, which is the video which has had the pixels manipulated to show more FOV information than would otherwise exist in the real world, is merged with real world visual information to create a "mixed reality" display, so that the patient sees augmented video with the manipulated images on the display of the glasses, lenses, or retina, which is then slowly merged back into a real world video matched as closely as possible with the real world unmodified vision of the patient, all of which combine in the mind to create one homogeneous corrected image.

In another aspect of this invention, the glasses or lenses are not used and the image is displayed upon smart contact lenses which receive the video from a remote source which has received the video, manipulated the image and re-projected the modified image onto the smart contact lenses for the patient to see.

In another aspect of this invention, the lenses, such as Wave Guide projected lenses, Mirror projected lenses, transparent OLED lenses, or film applied to lenses, such as 3M reverse projection transparent film, upon which the video or images are to be displayed may be glued or similarly affixed to the patient's corrective lenses, such that the patient sees both the prescription corrected real world images along with the video projected augmented images, all of which combine in the mind to create one homogeneous image.

In another aspect of the invention, pixel algorithms are used to use the outer boundary of the projected FOV to intersperse augmented visual information which by skipping some, but not all pixels, to permit real world information to be viewed through the see-through glasses or lenses, a merging effect "mixed reality" is created which merges the real-world images to the eye with the augmented video.

In another aspect of this invention, the prescriptive corrective lenses may be worn together with the "mixed reality" see-through lenses, without the same being glued or directly affixed. In this case they corrective lenses would have a mechanism to "snap in" or otherwise hold the corrective lenses within a close proximity to the augmented "mixed reality" lenses.

In another aspect of the invention, contact lenses, upon which augmented images can be viewed can be used together with the patient's own prescription glasses and/or lenses.

In another embodiment of the invention, this manipulated video of the real world would be displayed on see through glasses, and improvement over the enclosed goggles which previously existed, in order to merge manipulated video information with real world visuals.

The model controller is further configured to establish a border somewhere in the FOV as a function of data associated with the augmented visual model. The boundary is indicative of an area to be corrected within the patient's vision, wherein the area to be corrected includes more visual information than would originally exist in that same FOV in the real world. In other words, to correct for the patient's limited FOV, the image or pixels from the area where the patent cannot see are included into the FOV where the patient can see.

In one embodiment of the invention, this occurs with reducing the overall size of the pixels to be able to include the manipulated pixels. In another aspect of the invention, the pixels are the same size but are manages pixel by pixel to include additional visual information.

In one embodiment of the invention, for instance in the case of correction and merging of augmented video with real world vision, a macular degeneration patient would use interlaced video rather than progressive video protocols, and the removed pixels reside in the alternate interlace.

The model controller is further configured to establish a retinal map as a function of the boundary and to store the retinal map in the database. The display controller is configured to receive and to store the retinal map. The display controller is further configured to receive an image from a camera or cameras from associated with the patient and to apply corrections to the image based on the retinal map and responsively generate a corrected image. The display unit is coupled to the display controller and is configured to receive the corrected image to present the corrected image to the eye of the patient.

In other embodiments, a method is provided. The method includes the steps of establishing, by a model controller, a visual model associated with a patient and storing the visual model in the database. The visual model includes data related to a quality of the patient's vision. The method further includes the step of establishing, by the model controller, a boundary as a function of data associated with the visual model, the boundary being indicative of an area to be corrected within the patient's vision into which corrected FOV where the additional pixels removed from the non-visual area of the patients FOV are added.

The method also includes the steps of establishing, by the model controller, a retinal map as a function of the boundary and storing the retinal map in the database, receiving, at a display controller, an image from a camera or cameras associated with the patient, applying corrections to the image based on the retinal map, and responsively generating a corrected image. Further, the method includes the steps of receiving, at a display unit, the corrected image and presenting the corrected image to the eye of the patient.

In still other embodiments, one or more non-transitory computer-readable storage media have computer-executable instructions embodied thereon. When executed by at least one processor, the computer-executable instructions cause the at least one processor to establish, by a model controller, a visual model associated with a patient and storing the visual model in the database. The visual model includes data related to a quality of the patient's vision. A boundary is established as a function of data associated with the visual model, the boundary being indicative of an area to be corrected within the patient's vision. A retinal map is established as a function of the boundary. An image from a camera or cameras associated with the patient is received at a display controller. Corrections are applied to the image based on the retinal map, and a corrected image is generated. The corrected image is presented to the eye of the patient.

INDUSTRIAL APPLICABILITY

With reference to the drawings and in operation, the present invention provides systems, and methods to stretch, skew, and manipulate the image being projected on the eye to avoid the vision impaired or unsighted portions of the macula, and be directed to the remaining central vision, sighted macular vision, and the near peripheral vision. The findings of the inventors being that the displaced pixels or images should be removed but replaced as near the original position as possible. In this instance, the Central Vision area typically is said to comprise the central 5 degrees FOV of the eye, with the Paracentral area being the most central 8 degrees of the eye's vision and the Macular Vision being the central 18 degrees of the eye's vision. Typically with an AMD patient, the eye defect lies within these areas. On the outside of the Macular Vision is what is called the Near Peripheral area of the eye which comprises the next 30 degrees of the FOV of the eye. If possible, since the receptors of the eye are the most similar to the central portion of the eye, the displacement of the pixels or image should be to the nearest possible Near Peripheral Field of Vision of the eye.

The whole foveal area including foveal pit, foveal slope, parafovea, and perifovea is considered the macula of the human eye. This is what is destroyed with macular degeneration. Familiar to ophthalmologists is a yellow pigmentation to the macular area known as the macula lutea. The macula lutea is thought to act as a short wavelength filter, additional to that provided by the lens. The fovea is the most essential part of the retina for human vision and contains short-wavelength receptors cells, medium-wavelength receptor cells, and long-wavelength receptor cells. Thus, the central approximate 10 degrees of the eye's FOV projects onto approximately the central 3 mm of retina, or a region within 1.5 mm radius of the fovea centralis positioned at 0° eccentricity. This is a slightly larger area than the region that contains the yellow macular pigments, which is 4-6° in diameter (macula lutea) or the Macula. The foveola approximately coincides with the area of peak cone density in the photoreceptor layer, and in general is centered within a small region devoid of retinal vessels—the 'foveal avascular zone' (FAZ). Thus, the repositioning of pixels or images must be concentrated onto the remaining non-defect areas of this region, as much as possible, as the cones in this region are so densely packed that they look almost like rods. Also, the relationship to the cellular structure and ganglia are on par with a more one-to-one basis than any other area in the eye, so that just making a "hole" bigger, if it ignores sighted portions of the foveolar centralis makes a far less crisp picture.

Figure 25:
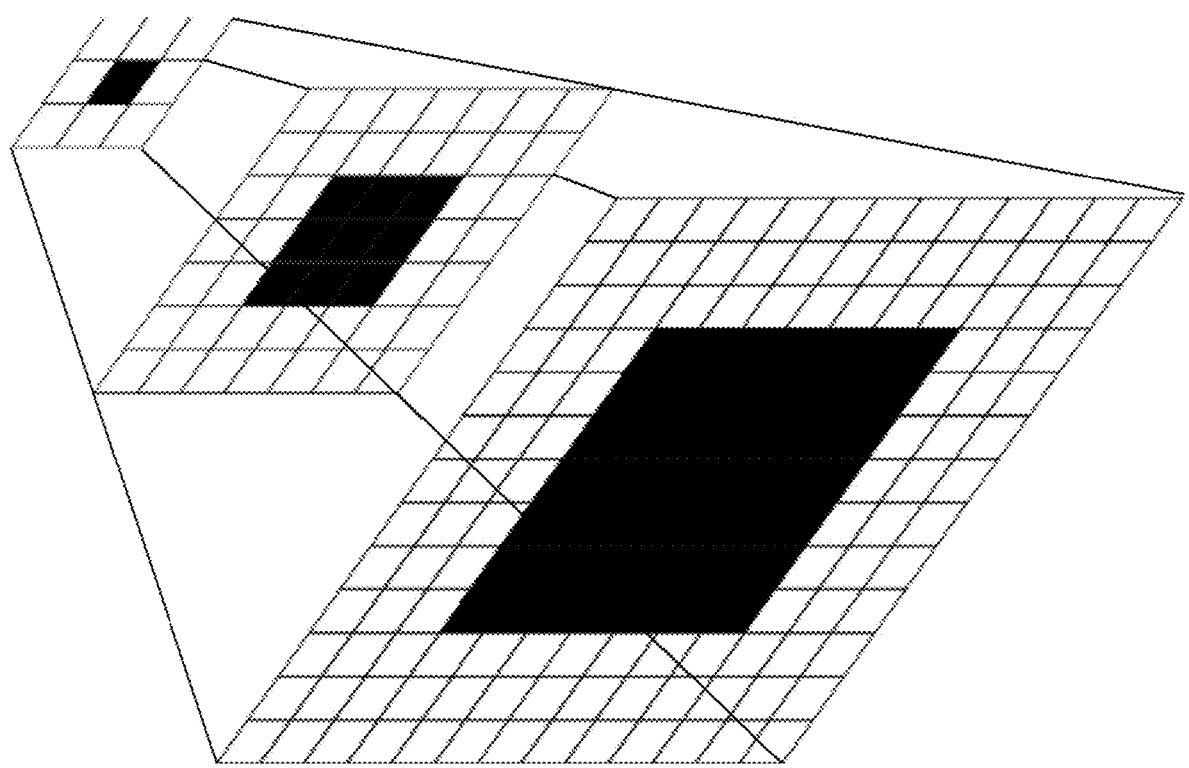
FIG. 25 is an illustration of subpixel mapping.
Figure 26:
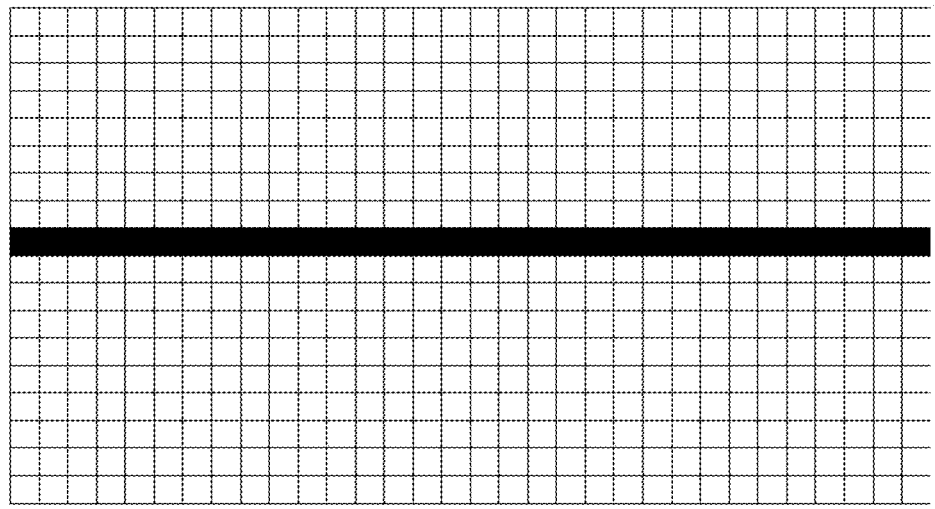
FIG. 26 is a graphical illustration of the corrected field of vision, showing the area of pixel manipulation.
Figure 26:
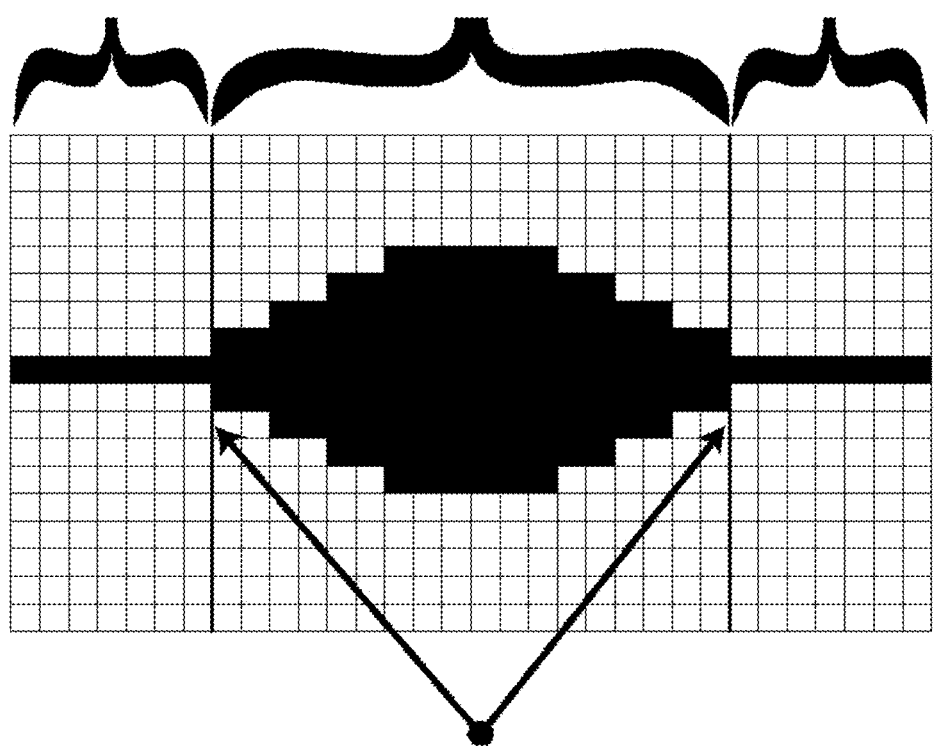
Figure 27:
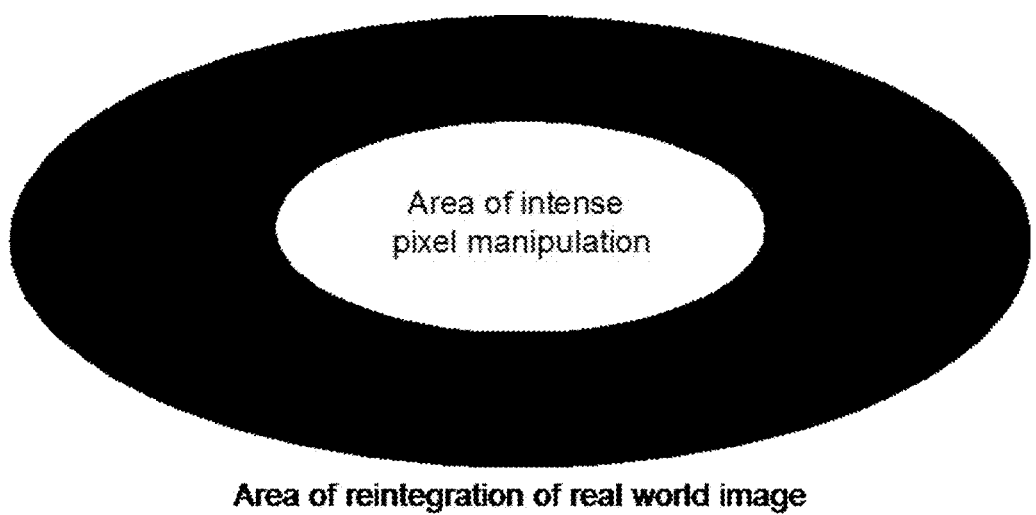
FIG. 27 is a further illustration of the corrected field of vision, showing the area of pixel manipulation.
Figure 28:
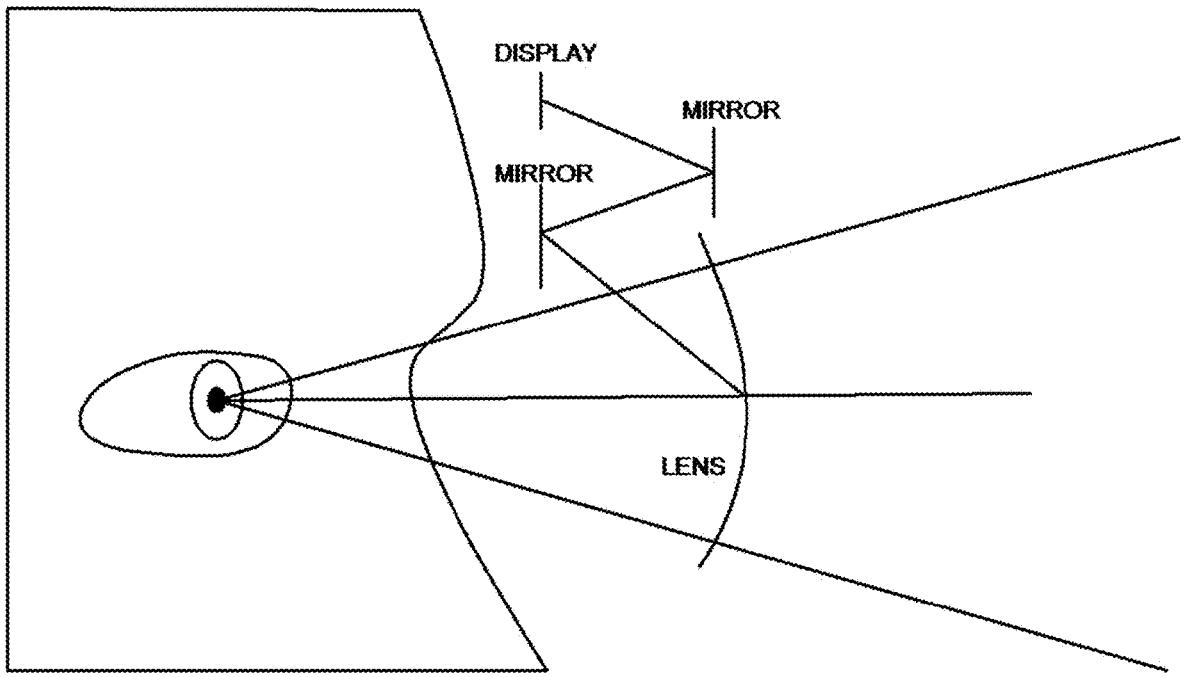
FIG. 28 is an illustration of the system with remote camera (top) and contact lens camera (bottom)
Figure 28:
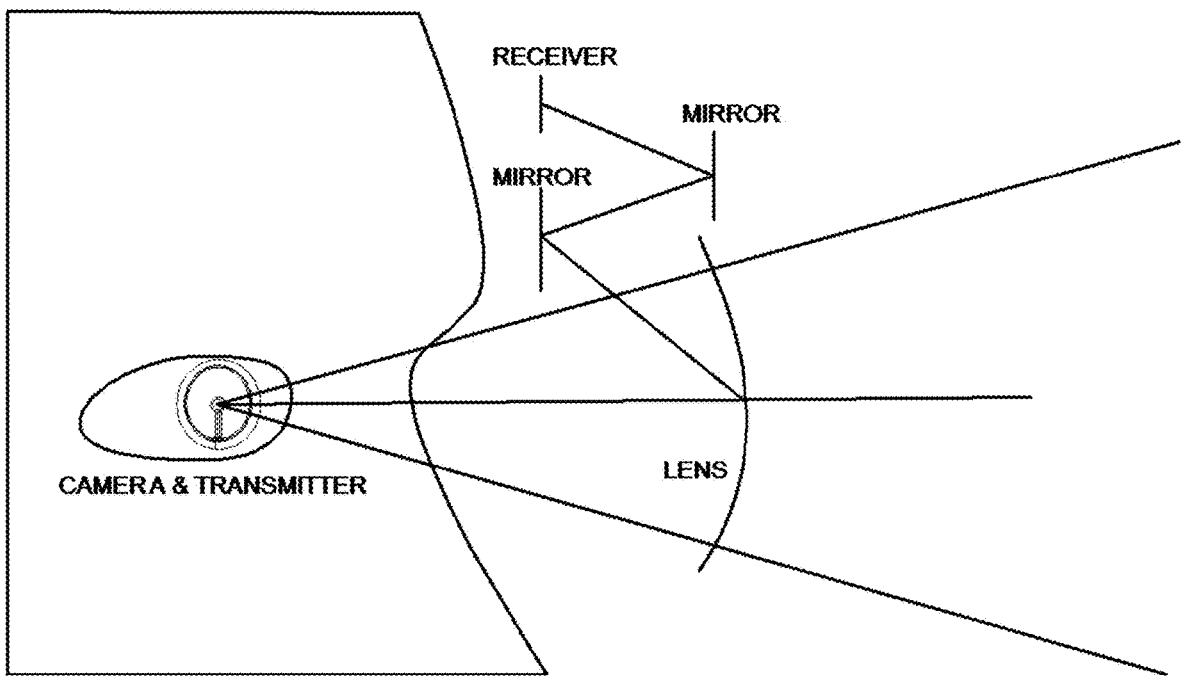
Figure 29:
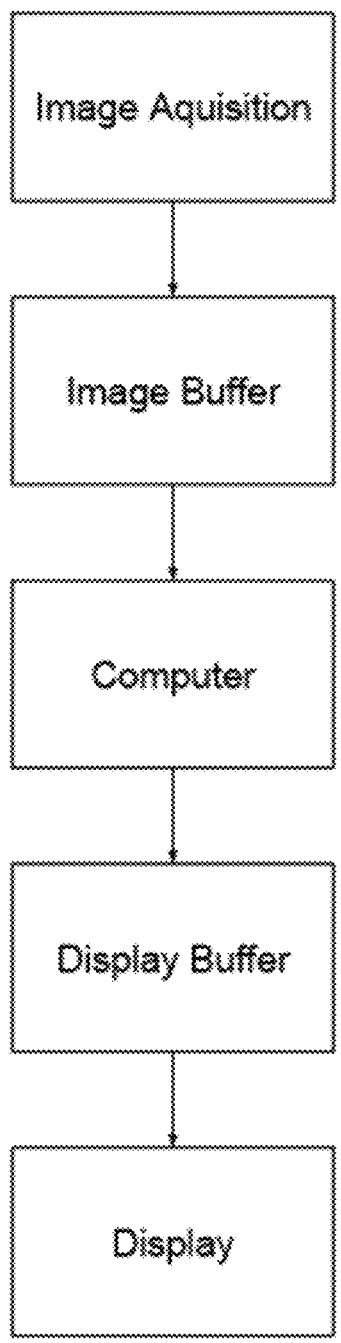
FIG. 29 is a flow chart of the process.

For this reason, the software must not just "cut a hole" as a homogeneous looking space, like an oval or a circle, but the software must as precisely as possible remove the pixels and images from the non-sighted areas and replace them in the next closest sighted areas, despite the highly irregular pattern this might demand. FIG. 25 depicts how this is to be accomplished. In this way the remaining sighted portions of the foveolar centralis and macula are used to project the modified image to make the best use of this specialized region of the eye.

If the disease has progressed, where there are no remaining sighted portions of the macula or foveolar centralis, then the image is to be displaced and projected on the closest nearest area with the highest concentration of cones which exists.

The distribution of rods and cones across the surface of the retina also has important consequences for correction for macular degeneration. Typically, the total number of rods in the human retina, approximately 91 million, which exceeds the number of cones at approximately 4.5 million. As a result, there is a higher density of rods throughout most of the retina, while the cones are more concentrated in the central vision portion of the eye. Since daytime vision and acuity is highly dependent on cone-mediated vision, transference of the modified picture and video is preferred to any remaining areas that contain the most cones for the best augmented acuity.

Since the relationship of cones and rods changes dramatically in the fovea (macula), a highly specialized region of the central retina that measures about 1.2 millimeters in diameter, this is the area of first focus for the repositioned augmented pixels and image. In the fovea, cone density increases almost 200-fold, reaching, at its center, the highest receptor packing density anywhere in the retina. The increased density of cones in the fovea is accompanied by a sharp decline in the density of rods. In fact, the central 300 µm of the fovea, called the foveola, is totally rod-free. Thus, an important aspect of this invention is to displace the pixels or image to as similar an area of the eye as possible, so that perception of the image by the eye is projected onto an area which is as close to the same as the damaged area, in terms of rods and cones, as possible.

To accommodate this specific displacement area, up to 15 degrees (typically a patient does not have the entire macular area defective, at least in the early stages, so 15 degrees is usually an outside range with 5 to 8 degrees being more typical) additional pixels and images must be placed within the closest 30 degrees FOV to the unsighted area.

Alternatively, if no area exists where there is a concentration of cones, then the image must be moved to the next best place which is the Near Periphery and the retina's peripheral receptors. Alternatively, the image can be skewed to immediately adjacent portions of the retina in an irregular fashion that best approximates the area of defect. In this way, the entire image is projected on the functioning retinal receptors, and any involvement of the macula is avoided. The systems and methods, according to embodiments of the present invention, create a distortion map of the entire image and project it onto the periphery of the eye, while avoiding the macula. This can be done by the use of computer aided 90-degree 3D or similar High Definition goggles or glasses, or by photon projection with a virtual retina display of the image directly onto the retina of the eye.

In some embodiments of the invention, the method and manner of the skewed projection relies on external lenses, with up to 2 million pixels, a resolution seen only otherwise on ultra-high-definition TVs and tablet computers, which provide the resolution needed to put the entire image on the peripheral retina receptors in sufficient detail to be analyzed by the optical nerve and brain.

Also, for the introduction of perspective, two cameras can to be used, and the modern goggles and glasses can accept more than one image interface and/or signal. Thus, the computed manipulated images are captured in real-time and displayed in real-time for the patient.

In addition, the goggles and/or glasses could be used to house a technology like virtual retina display, retina scan display projection, and/or a retinal projector technology which all use photon on retina projection, which in this case would be modulated by the IDM (Image Distortion Map) to the person's specific Retinal Map so that an intentionally distorted image would be projected onto the areas of the eye which have the best visual reception. In this fashion, you can project the image directly into the portion of the peripheral retina which is still active in a macular degeneration patient via photons, utilizing a technology such as a virtual retinal display (VRD), also known as a retinal scan display (RSD) or retinal projector (RP), is used. When combined with these technologies, the person's specific retinal map, modulated by the image distortion map, would be displayed by the technology which draws a raster display (like a television) directly onto the retina of the eye, and in this case on to the usable portions of the retina of the eye. With the VRD, RSD, or RP, the patient user sees what appears to be a conventional display floating in space in front of them, which is corrected for the loss of macula, but still provides the patient with the ability to see other peripheral obstacles, such as steps in front of the patient which the camera is not yet focused on. In addition, the goggles and/or glasses could be used to house a technology like virtual retina display, retina scan display projection, and/or a retinal projector technology which all use photon on retina projection, which in this case would being modulated by the pixel manipulation according to the person's specific loss of sight. In this fashion, you can scan the manipulated image directly into the portion of the peripheral retina which is still active in a macular degeneration patient via photons. These photons may be projected by cameras in the glasses or by Smart Contact Lenses, which may or may not receive its information, energy, and connection from the GFH.

Another advantage is that these types of wide field-of-vision goggles or glasses can be used in conjunction with one or more cameras, which are typically head mounted. Another advantage of these types of glasses is that they can be combined with proximity sensors, motion sensors, head and eye tracking, a feature which is advantageous for understanding a user's specific field of vision for adjustments, and to measure distance through triangulation. For instance, in human eyes there is a convergence of the image when it comes closer to the face, meaning that the image captured by each eye begins to overlap the other eye's image. In 3D camera applications, this convergence is not always taken into account, and the sensors can also be used to automatically change the field of view presented to the retina, i.e., a virtual zoom to determine facial features when in proximate distance of another person. When used in conjunction with a user interface, the zoom, skew or other manipulation features can be selected in a straightforward method chosen by the user to gain visual acuity in various environments. A differential adjustment may also be chosen with regard to each eye. Alternatively software derived proximity and motion sensing can be employed by utilizing comparative techniques on sequential camera images.

Thus, this invention teaches that, one camera can be used for monoscopic image capture and display. In addition, this invention teaches that you can use two cameras to simulate on the goggles/glasses display true stereoscopic vision, wherein the IDM (Image Distortion Map) model includes factor correction for epipolar curves, guided by the epipolar geometry so that stereoscopic vision, generated by two or more cameras, can be employed and be displayed, and seen.

The invention uses computer aided video images which are skewed and stretched in a matrix distortion or other similar fashion to put the most or the entirety of the image onto the peripheral vision of the patient by opening up the center of the image and manipulating it to the peripheral cones of the eyes, as seen by the patient in the projected image, in order to project the video captured images on the peripheries of the cones in the eyes where vision is still active. The benefits of this invention are that no invasive procedures are necessary and as the MD changes, the software can be adjusted so that the image is now correctly skewed. It is an additional advantage of this invention that live feedback can be provided.

In the fashion taught by this invention, the viewed experience makes it nearly impossible for the user to distinguish between what is actually seen and the image that is created by the distortion map.

Thus, the spreading and/or multi-lateral skewing of the image which reflects the corrected image onto 3D or High-Definition goggles and/or glasses worn by the patient. The image is skewed via the IDM (Image Distortion Map) module to avoid projection to the area of the eye which involves the macula, but still has all the image information. To imagine this process, think of a picture which is printed onto a stretchable and compactable substance. A hole is cut into the middle of the image and stretched open. This makes the image compress into the sides of the picture. Thus, all of the information of the picture is still there, it is just rearranged where a hole is in the middle and the image is moved each way to the side, top and bottom. This "hole-cutting" is done via algorithms and computer software/firmware technology, for instance, using a technology like Image Distortion Mapping as above mentioned.

In one embodiment, the process maps each pixel in the two dimensional image (or video) from the camera(s) and maps the pixel to a new pixel location on the display. In another embodiment, only the data points are remapped. The other image data is transformed using a predefined function that interpolates the data between the data points.

The IDM model takes vector values (numbers) that describe the lens center of the goggle device (per eye, on the oculus rift) (called "1Cr"), as well as field of view of the display, and returns the vector object that defines how to distort the image to make it more viewable by someone with macular degeneration. The key element is to define the mapping between image (pixel) coordinates and 3D rays in the camera(s) coordinates as a linear combination of non-linear functions of the image coordinates. This allows a linear algorithm to estimate nonlinear models, and creates a method to distort the image such that there is typically a (circular) "hole(s)" or a "cut-out(S)", or a geometrically distorted area in the center of the image accomplished by moving the pixel coordinates so that the entire image is distorted and mapped around the hole which is cut-out or to compensate for the geometric distortion caused by leaking vessels. How this image is exactly cut-out and the pixels rearranged is accomplished through testing with the subject so that it is attempted to use as many peripheral retina receptors as that subject has active. This Image Distortion Map ("IDM") model thus becomes that person's Prescribed Retinal Interface ("PRI").

This invention has great benefits in that it is non-invasive, can be worn or not worn, and is easier to adjust and keep fine-tuned because it is external, and image and algorithms which stretch and skew the image to the PRI can be adjusted in real-time based on MD Patient feedback in adjustments.

In another embodiment of the invention, the active retinal receptors are identified through evaluation with the system or by known prescription whereby the lowest number of receptors in the retina required to affect the desired mental and visual impression of the image are used to increase the apparent refresh rate, by actually increasing the refresh rate by displaying the image on less than all of the receptors.

In another aspect of the present invention, various FOV maps are stored and/or analyzed or tracked in a database. The database could be stored in the cloud. A knowledge base and decision tree based formula can be used to analyze the FOV maps, and one or more of the FOV maps could be used as a starting point for a patient. The selected FOV map could be fine-tuned using one or more of the methods described above. A FOV from the database may be chosen as a starting point based on patient visual models, common trends and outliers within the data. The FOVs models could be sorted and/or chosen based on identified common boundaries. The output of the different FOV maps, i.e., the resultant corrected images could be analyzed, with patient input, utilizing a process of comparison and elimination while viewing desired real world images, i.e., a face chart, text chart or the like.

A controller, computing device, server or computer, such as described herein, includes at least one or more processors or processing units and a system memory, which may be an embodiment in a personal computer, server, or other computing device. The controller typically also includes at least some form of computer-readable media. By way of example and not limitation, computer-readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer-readable instructions, data structures, program modules, or other data in a modulated data signal, such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer-readable media.

The order of execution or performance of the operations in the embodiments of the invention illustrated and described herein is not essential, unless otherwise specified. That is, the operations described herein may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In some embodiments, a processor or controller, as described herein, includes any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

Whereas, the devices and methods have been described in relation to the drawings and claims, it should be understood that other and further modifications, apart from those shown or suggested herein, may be made within the spirit and scope of this invention.

What is claimed is:

1. A wearable image manipulation system comprising:
a camera input system;
an image projection system, where the image projection system is capable of being worn by a user, where the image projection system comprises at least one contact lens with a display unit contained thereon or at least partially embedded therein;
a database capable of receiving, storing, and transmitting a retinal map; and
a processor in communication with the camera input system, the database, and the image projection system such that the processor is capable of receiving an image from the camera input system and modifying the image according to the retinal map to produce a modified image and displaying the modified image on the image projection system where by displaying the modified image comprises correcting eye defects of the user.

2. A wearable image manipulation system comprising:
a camera input system;
an image projection system, where the image projection system is capable of being worn by a user;
a database capable of receiving, storing, and transmitting a retinal map; and
a processor in communication with the camera input system, the database, and the image projection system such that the processor is capable of receiving an image from the camera input system and modifying the image according to the retinal map to produce a modified image and displaying the modified image on the image projection system where by displaying the modified image comprises correcting eye defects of the user,
further comprising one or more eye tracking cameras, where each eye tracking camera is pointed at a user's eye during use of the system and is capable of tracking movement of a user's eye and the system is capable of adjusting the camera input system such that the image received by the processor from the camera input system and displayed on the image projection system is based on the user's eye movement.

3. The system of claim 2 where each eye tracking camera, in conjunction with at least one infrared illuminator, is positioned such that it is pointed toward an eye of the user during use.

4. The system of claim 2 further comprising software utilized by the processor to adjust the displayed image and/or modified image according to eye gaze based on eye tracking data from the one or more eye tracking cameras.

5. The system of claim 2 where modifying the image comprises correcting for epipolar geometry and line of sight.

6. The system of claim 1 further comprising headgear, where the headgear houses the image projection system.

7. The system of claim 6 where the headgear houses one or more of the following sensors: motion sensors, degrees of freedom sensors, gesture recognition sensors, fiducial marker sensors, accelerometer sensors, infrared sensors, motion sensors, alert sensors, gyroscope technology and related sensors, positional tracking sensors, sound sensors, microphone sensors, optical sensors, magnetic sensors, acoustic sensors, and/or inertial sensors.

8. The system of claim 6 where the headgear houses one or more of the following subsystems: dynamic opacity; hologram projection; simultaneous localization and mapping; head and eye tracking; hand and arm tracking; body tracking; and/or environment mapping interfaces.

9. The system of claim 6 where the headgear houses the processor.

10. The system of claim 6 where the headgear houses the camera input system.

11. The system of claim 6 where the headgear is capable of being worn on the head of the user and positioned over the user's eyes and nose like glasses.

12. The system of claim 6 where the headgear is a helmet and the display is a face shield.

13. The system of claim 1 where the camera input system comprises one or more video cameras, one or more still cameras, one or more night-vision cameras, one or more infrared cameras, one or more thermal imaging cameras, one or more 3D cameras, or any combination thereof.

14. The system of claim 1 where the system is capable of recording images from the camera input system.

15. The system of claim 1 where the image projection system is capable of displaying at least part of the image and at least part of the modified image simultaneously.

16. The system of claim 1 where the image projection system is a reflected image micro display system comprising:
  at least one image source; and
  a reflective lens;
where the image source is capable of projecting the image and/or modified image onto the reflective lens, which is capable of reflecting the image and/or modified image to an eye of the user.

17. The system of claim 16 where the reflected image micro display system further comprises a correction module located between the image source and the reflective lens, such that the image and/or modified image passes through the correction module prior to reaching the reflective lens.

18. The system of claim 17 where the correction module comprises:
  a first corrective lens;
  a polarization layer; and
  a second corrective lens,
where the polarization layer is sandwiched between the first corrective lens and the second corrective lens.

19. The system of claim 18 where the polarization layer is capable of retarding light that would otherwise be reflected back to the image source and focusing the image and/or modified image onto a specific part of the reflective lens.

20. The system of claim 17 where the correction module is adjustable based on the location of the user's eye.

21. The system of claim 17 where the reflective lens is a spherical lens corresponding to one or more corrective lenses of the micro display correction module.

22. The system of claim 16 where the reflective lens is coated with a semi-reflective or reflective surface.

23. The system of claim 16 where the reflective lens is a corrective lens for better focus.

24. The system of claim 16 where the image source and the reflective lens are adjustable based on the location of the user's eye.

25. The system of claim 24 further comprising an eye tracking camera, where the eye tracking camera is capable of tracking movement of the user's eye and the system is capable of adjusting the image source and the reflective lens based on the movement of the user's eye.

26. The system of claim 25 where the eye tracking camera is part of an eye tracking subsystem capable of determining an interpupillary distance (IPD) of the user's eyes and capable of adjusting for the differences in IPD of the specific user.

27. The system of claim 16 where the image source has an ultra-short throw.

28. The system of claim 1 where the system is capable of running one or more apps and displaying images from the apps on the image projection system.

29. The system of claim 1 where the system is in communication with an external device running one or more apps such that the system is capable of displaying images from the apps on the image projection system.

30. The system of claim 29 where the external device is a cell phone, tablet, smart watch, or computer.

31. The system of claim 29 where the system is paired with the external device.

32. The system of claim 29 where the system is in communication with the external device via cellular, Bluetooth, Bluetooth Low Energy, or WIFI or other radio frequencies or wireline or wireless frequencies.

33. The system of claim 1 comprising multiple sets of camera input systems, image projection system, and processors, where the processors of the multiple sets are networked.

34. A wearable image manipulation system comprising:
  a camera input system comprising at least one forward-facing camera where the camera input system is partially or completely embedded on one or more smart contact lenses;
  an image projection system, where the image projection system is capable of being worn by a user;
  a database capable of receiving, storing, and transmitting a retinal map; and
  a processor in communication with the camera input system, the database, and the image projection system such that the processor is capable of receiving an image from the camera input system and modifying the image according to the retinal map to produce a modified image and displaying the modified image on the image projection system.

35. The system of claim 34 where each smart contact lens comprises:
  battery;
  charging apparatus;
  one or more sensors; and
  one or more communication devices.

36. The system of claim 35 where the communication devices are capable of communicating via backscatter, interscatter, Bluetooth, Wi-Fi, ZigBee, RFID, and/or other antenna transmissions.

37. The system of claim 34 where each smart contact lens comprises one or more cameras.

38. The system of claim 37 where the system is capable of monitoring the user's eye movement, where each smart contact lens comprises more than one camera, and where one or more of the more than one cameras is backward facing toward the user's eye.

39. The system of claim 38 where the processor is capable of using information obtained from monitoring the user's eye movement to adjust the display of the modified image according to eye gaze.

40. The system of claim 1 where the image projection system is a heads-up display.

41. The system of claim 40 further comprising an eye-tracking subsystem, where the heads-up display is capable of displaying the image and/or the modified image positioned according to the user's eye gaze based on information obtained from the eye-tracking subsystem.

42. The system of claim 40 where the heads-up display comprises a reflective lens capable of dynamic opacity such that the display has an opacity capable of manual or automatic modification in a range from transparent to opaque.

43. The system of claim 1 where the camera input system comprises one or more cameras.

44. The system of claim 12 where the display is a reflective display.

* * * * *